(12) United States Patent
Scheinberg et al.

(10) Patent No.: US 10,406,236 B2
(45) Date of Patent: *Sep. 10, 2019

(54) SINGLE WALL NANOTUBE CONSTRUCTS AND USES THEREOF

(71) Applicants: David A. Scheinberg, New York, NY (US); Michael R. McDevitt, New York, NY (US); Christophe Antczak, Arlington, MA (US); Debjit Chattopadhyay, Pennington, NJ (US); Rena May, Baltimore, MD (US); Jon Njardarson, Tucson, AZ (US); Mark Reid Phillips, New York, NY (US)

(72) Inventors: David A. Scheinberg, New York, NY (US); Michael R. McDevitt, New York, NY (US); Christophe Antczak, Arlington, MA (US); Debjit Chattopadhyay, Pennington, NJ (US); Rena May, Baltimore, MD (US); Jon Njardarson, Tucson, AZ (US); Mark Reid Phillips, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/494,974

(22) Filed: Apr. 24, 2017

(65) Prior Publication Data

US 2017/0297912 A1    Oct. 19, 2017

Related U.S. Application Data

(60) Division of application No. 14/034,503, filed on Sep. 23, 2013, now Pat. No. 9,629,927, which is a continuation-in-part of application No. 11/989,672, filed as application No. PCT/US2006/029692 on Jul. 31, 2006, now Pat. No. 8,540,965.

(60) Provisional application No. 60/797,273, filed on May 3, 2006, provisional application No. 60/703,194, filed on Jul. 29, 2005.

(51) Int. Cl.

| | |
|---|---|
| A61K 47/52 | (2017.01) |
| A61K 39/385 | (2006.01) |
| A61K 47/64 | (2017.01) |
| A61K 47/65 | (2017.01) |
| A61K 51/12 | (2006.01) |
| B82Y 30/00 | (2011.01) |
| B82Y 40/00 | (2011.01) |
| C01B 32/174 | (2017.01) |
| C01B 32/176 | (2017.01) |
| A61K 47/69 | (2017.01) |
| B82Y 5/00 | (2011.01) |

(52) U.S. Cl.
CPC .......... *A61K 47/52* (2017.08); *A61K 39/385* (2013.01); *A61K 47/64* (2017.08); *A61K 47/65* (2017.08); *A61K 47/6925* (2017.08); *A61K 51/1248* (2013.01); *A61K 51/1275* (2013.01); *B82Y 30/00* (2013.01); *B82Y 40/00* (2013.01); *C01B 32/174* (2017.08); *C01B 32/176* (2017.08); *B82Y 5/00* (2013.01); *C01B 2202/02* (2013.01); *C01B 2202/28* (2013.01); *C01B 2202/34* (2013.01); *C01B 2202/36* (2013.01)

(58) Field of Classification Search
None
See application file for complete search history.

(56) References Cited

U.S. PATENT DOCUMENTS

2004/0076681 A1*  4/2004  Dennis ................ A61K 9/0092
                                                        424/489

OTHER PUBLICATIONS

Deshpande et al., Yttrium-90-Labeled Monoclonal Antibody for Therapy: Labeling by a New Macrocyclic Bifunctional Chelating Agent; Journal of Nuclear Medicine, vol. 31, No. 4, pp. 473-479, 1990.*
Bos et al., In Vitro Evaluation of DNA-DNA Hybridization as a Two-Step Approach in Radioimmunotherapy of Cancer; Cancer Research, vol. 54, pp. 3479-3486, 1994.*
Wiseman et al., Radiation Dosimetry Results and Safety Correlations from 90Y-Ibritumomab Tiuxetan Radioimmunotherapy for Relapsed or Refractory Non-Hodgkin's Lymphoma: Combined Data from 4 Clinical Trials; J Nucl Med, vol. 44, pp. 465-474, 2003.*
Buchholz et al., PET imaging with yttrium-86: comparison of phantom measurements acquired with different PET scanners before and after applying background subtraction; Eur J Nucl Med Mol Imaging, vol. 30, pp. 716-720, 2003.*

* cited by examiner

*Primary Examiner* — Addison D Ault
(74) *Attorney, Agent, or Firm* — Benjamin Aaron Adler

(57) ABSTRACT

The present invention provides soluble single wall nanotube (SWNT) constructs functionalized with a plurality of a targeting moiety and a plurality of one or more payload molecules attached thereto. The targeting moiety and the payload molecules may be attached to the soluble SWNT via a DNA or other oligomer platform attached to the SWNT. These soluble SWNT constructs may comprise a radionuclide or contrast agent and as such are effective as diagnostic and therapeutic agents. Methods provided herein are to diagnosing or locating a cancer, treating a cancer, eliciting an immune response against a cancer or delivering an anticancer drug in situ via an enzymatic nanofactory using the soluble SWNT constructs.

5 Claims, 14 Drawing Sheets

Specification includes a Sequence Listing.

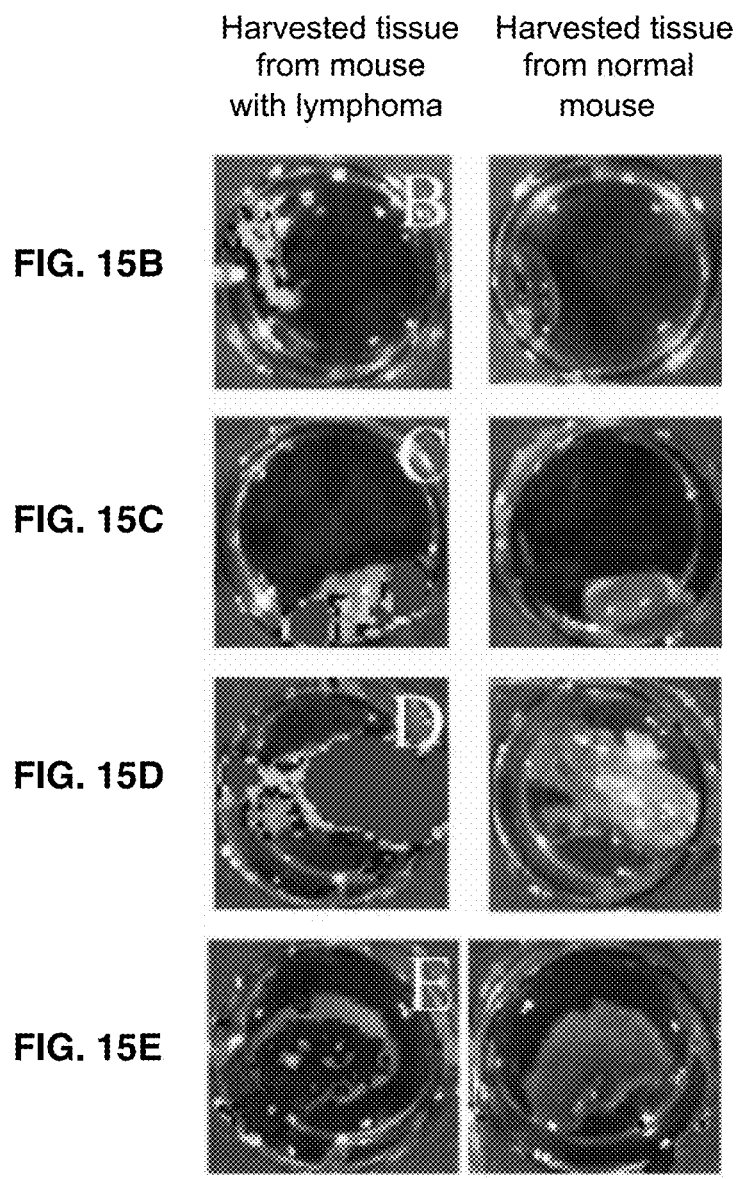

① ⟷ cleavage by carboxypeptidase A
② ⟷ cleavage by β-glucuronidase

SINGLE WALL NANOTUBE CONSTRUCTS AND USES THEREOF

CROSS-REFERENCE TO RELATED APPLICATIONS

This application is divisional under 35 U.S.C. § 120 of pending application U.S. Ser. No. 14/034,503, filed Sep. 23, 2013, which is a continuation-in-part under 35 U.S.C. § 120 of application U.S. Ser. No. 11/989,672, filed Apr. 28, 2009, now U.S. Pat. No. 8,540,965, which is a national stage application under 35 U.S.C. § 371 of international application PCT/US2006/029692, filed Jul. 31, 2006, now abandoned, which claims benefit of priority under 35 U.S.C. § 119(e) of provisional application U.S. Ser. No. 60/797,273, filed May 3, 2006, and of provisional application U.S. Ser. No. 60/703,194, filed Jul. 29, 2005, the entirety of all of which is hereby incorporated by reference.

GOVERNMENT SUPPORT CLAUSE

This invention was made with government support under grant number CA092629 awarded by the National Institutes of Health. The government has certain rights in the invention.

BACKGROUND OF THE INVENTION

Field of the Invention

The present invention relates generally to the fields of carbon nanotube chemistry, radioimmunotherapy and other targeted therapies. More specifically, the present invention relates to functionalized single wall nanotube therapeutic compositions, the construction thereof and uses therefor.

Description of the Related Art

Single wall carbon nanotubes (SWNT) offer both unusual opportunities as well as challenges. SWNTs are scalable, while retaining their key properties thus allowing design of a platform suitable for different applications in vivo. In addition, toxicity and clearance are size- and composition-dependent, allowing flexibility of design to reduce possible adverse effects. SWNTs have enormous aspect ratio, which allows huge amplification of effecter function and altered kinetics of conjugated agents. Additionally, all the carbons atoms, i.e., ~8000 per 100 nm, are on the surface and therefore available for functionalization allowing attachments of multiple functionalities, in large numbers, simultaneously. This allows simultaneous applications as needed, e.g., for signaling molecules or for therapeutic agents. SWNT have a regular and identically repeating structure which should allow construction of regular and repeating functionalization, as well as patterns of functions. Biological processes interacting with the modified SWNT are likely to recognize the multivalency and repetition as they do for other biological recognition systems.

SWNT are inert, stable, flexible, and non-immunogenic. Most larger molecules introduced into living organisms can be recognized by the immune system, and thereafter quickly neutralized upon re-injection, recognized by metabolic systems, and therefore rapidly degraded, or are unstable and denatured within the reducing, warm and physiological environment of the body and tumors. SWNT have important electronic properties. The development of biologic sensors, telemetry or crude decision-making devices that could function ex vivo or in vivo may be possible with modified SWNT.

While there are many potential advantages to the use of SWNT as a base nanomaterial, there are also possible hurdles and disadvantages. The chemistry necessary to efficiently solubilize SWNT is beginning to be described but the effects of these identifications on the chemical and electronic properties of the SWNT are not known.

Although, parent single walled carbon nanotubes, unmodified and in some instances unpurified, have been reported to be toxic, there has been no thorough study concerning the in vivo biological properties of solubilized SWNTs. For example parent SWNTs have been reported to be cytotoxic to human keratinocytes and were also shown to inhibit growth of embryonic rat-brain neuron cells (1). It has been demonstrated separately that parent SWNTs induced the formation of mouse-lung granulomas (2). It has also been reported that SWNTs inhibit the proliferation of human HEK293 cells, induce cell apoptosis and decrease adhesive ability of cells (3). However, for therapeutic and diagnostic applications SWNTs soluble in aqueous media possessing free pendent functionalities for subsequent attachment of drugs or imaging agents are more appropriate. To this effect derivatized SWNTs with pendent peptides or CpG motifs have been shown to cross cell membranes (3). However, at SWNT concentrations greater than 10 μM cell death was dramatic and no clear mechanism was cited (4). On the other hand, the uptake of solubilized SWNTs (0.05 mg/mL) by endocytosis into a range of cell lines, e.g., HI60, Jurkat, CHO and 3T3 fibroblasts, has been reported and it has been demonstrated that the nanotubes are localized in the endosomes and were non-toxic (5).

SWNT are unique among solid-state materials in that every atom is on the surface and hence surface chemistry could therefore be critical to the physical properties of SWNTs and their applications. SWNTs with aspect ratio approaching $10^4$-$10^5$, form a unique class of one-dimensional quantum confined structures exhibiting either semi-conducting (sem-) or metallic (met-) behavior are of special interest. Based on their sem- and/or met-character, a number of devices such as field-effect transistors, single electron transistors and computational logic gates have been demonstrated (6).

Moreover, SWNTs have the highest known specific conductivity per unit mass providing the ability to facilitate direct electron-transfer with biomolecules, acting as molecular-scale electrical conduits, and generating unique designing nano-scale biosensors. Similarities between the size scales of enzymes and chemically shortened SWNTs may promote the likelihood of SWNTs to come within electron tunneling distance of enzyme redox sites, improving sensitivity for enzyme labels that generate signals by direct electron exchange and communicate with external data capture devices. Bridging nanotubes with biological systems, however, is a relatively unexplored area, with the exception of a few reports on nanotube probe tips for biological imaging, nonspecific binding (NSB) of proteins, functionalization chemistry for bioimmobilization on nanotube sidewalls, internalization and transport through cell membrane of solubilized SWNTs in in vitro cell cultures and peptide SWNT constructs for vaccines.

SWNTs as platforms for investigating surface-protein and protein-protein binding and its subsequent use in cancer immunotherapy has remained completely unexplored. Hence methodologies aimed at the functionalization of nanotubes with specific antibodies and tagging SWNTs with alpha-emitting elements followed by the evaluation of both their biodistribution and specificity in vivo are needed and would have significant therapeutic implications. Early biofunctionalization approaches have relied heavily on modifications of the sidewalls of SWNTs via noncovalent chemistry so as to preserve the sp2 nanotube structure and thus their electronic characteristics (7). The 1,3-dipolar cycloaddition of azomethine ylides with SWNTs results in amine functionalized SWNTs and confers both aqueous solubility and chemical functionalization. These amine functionalized SWNTs are compatible with a myriad of established bioconjugation techniques (8).

There is a significant need in the art for therapeutic methods utilizing functionalized and soluble SWNTs comprising targeting and therapeutic moieties. Specifically, the prior art is deficient in methods of radioimmunotherapy or other immunotherapy or chemotherapy to treat or to prevent a cancer utilizing SWNTs which are functional to target and deliver a therapeutic molecule in vivo. The present invention fulfills this long-standing need and desire in the art.

SUMMARY OF THE INVENTION

The present invention is directed to a method of treating a pathophysiological state in a subject. The method comprises administering a soluble SWNT functionalized with a plurality of a targeting moiety and a plurality of one or more payload molecules attached thereto and targeting cells associated with the pathophysiological state with the targeting peptide. The payload is delivered to the associated cells where the payload has a therapeutic effect against the cells or elicits a therapeutic effect from the cells thereby treating the pathophysiological state in the subject.

The present invention also is directed to a method of eliciting an immune response against a cancer in a subject. A soluble SWNT construct having a plurality of one or more cancer-specific peptides comprising native or heteroclitic epitope sequences linked thereto are administered to the subject. T cells are activated against cells comprising the cancer via presentation of the epitopes by antigen-presenting cells thereby eliciting the immune response.

The present invention is directed further to a method of delivering an anticancer drug in situ to a cancer in a subject. A first component of a soluble SWNT construct having the structure SWNT-(peptide)$_x$-(DNA$_1$)$_x$-(DNA$_2$)$_x$ is administered such that the peptide targets cells comprising the cancer. A second construct component having the structure (cDNA$_1$-E$_1$)$_m$ and a third construct component having the structure (cDNA$_2$-E$_2$)$_n$ are administered subsequently. The soluble SWNT construct self assembles in situ via hybridization of the second and third construct components to the first construct component. An anticancer preprodrug is administered to the subject whereupon the sequential action of the enzymes activates the drug such that it is delivered in situ to the cancer. The self-assembled SWNT construct has the structure SWNT-(peptide)$_x$-(DNA$_{1,2}$-(cDNA$_1$-E$_1$)$_m$-(cDNA$_2$-E$_2$)$_n$)$_x$, where x is 1 to 300, m and n are independently 1 to 300, cDNA$_1$ and cDNA$_2$ are non-identical 18 mer oligonucleotides, DNA$_1$ and DNA$_2$ are 18 mer oligonucleotides with sequences complementary to cDNA$_1$ and cDNA$_2$, and E$_1$ and E$_2$ are enzymes.

The present invention is directed further still to a soluble SWNT construct having the structure SWNT-((peptide)$_m$-(M*DOTA)$_n$)$_x$, where x is 1 to 300, m and n are independently 1 to 300 and M* is a radionuclide or a contrast agent. The present invention is directed to a related invention where the SWNT construct further comprises DNA, RNA, PNA, or PSDNA oligomers linked independently to the SWNT, the peptide and DOTA. Particularly, the SWNT construct may have the structure SWNT-(DNA$_{1,2}$-(cDNA$_1$-peptide)$_m$-(cDNA$_2$-M*DOTA)$_n$)$_x$, where cDNA$_1$ and cDNA$_2$ independently are non-identical oligomers and DNA$_{1,2}$ is an oligomer with a sequence complementary to cDNA$_1$ and cDNA$_2$.

The present invention also is directed further still to a method of locating or diagnosing a cancer in a subject using the soluble SWNT constructs described herein. A soluble SWNT construct having the structure described supra, where the peptide is a targeting antibody or fragment thereof or other targeting peptide ligand and M* is a diagnostic radionuclide or a contrast agent, is administered to the subject. Cells comprising the cancer are targeted with the peptide and localization of the radionuclide or contrast agent is detected in the subject.

The present invention is directed further still to a method of treating a cancer in a subject using the soluble SWNT constructs described herein. A soluble SWNT construct having the structure described supra, where the peptide is a targeting antibody or fragment thereof or other targeting peptide ligand and M* is a therapeutic radionuclide, is administered to the subject. Cells associated with the cancer are targeted with the peptide and the therapeutic radionuclide is delivered to the cancer-associated cells such that the radionuclide has an anticancer effect against the cells. The present invention is directed to a related method where the soluble SWNT further comprises oligonucleotides linked independently to the SWNT, the peptide and DOTA. The soluble SWNT construct has the structure SWNT-(DNA$_{1,2}$-(cDNA$_1$-peptide)$_m$-(cDNA$_2$-M*DOTA)$_n$)$_x$, where cDNA$_1$ and cDNA$_2$ independently are non-identical oligonucleotides and DNA$_{1,2}$ is an oligonucleotide with a sequence complementary to cDNA$_1$ and cDNA$_2$. The present invention is directed to another related method where the targeting antibody is a therapeutic antibody.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 8A is a pilot of the 2-dimensional ROI data for all group I and II animals at 3 and 24 hours. Three regions per tissue per animal were collected and the average % ID/g and standard deviation determined. The average % ID/g tissue per animal was then used to determine an average % ID/g per tissue per group and the standard deviation within the group values was also calculated. FIG. 8B is a plot of the 24 hour biodistribution data obtained from tissue harvest, weighing and counting of organs from group I, II, and III mice.

FIGS. 15A-15E demonstrate, using bioluminescence imaging, the presence of luciferase positive Daudi cells in the bones of tumor-bearing SCID mice (FIG. 15A) and, using harvested tissue from bearing and non-tumoring bearing SCID mice, in the spleen (FIG. 15B), kidney (FIG. 15C), the spine (FIG. 15D), and the liver (FIG. 15E).

DETAILED DESCRIPTION OF THE INVENTION

Figure 1:
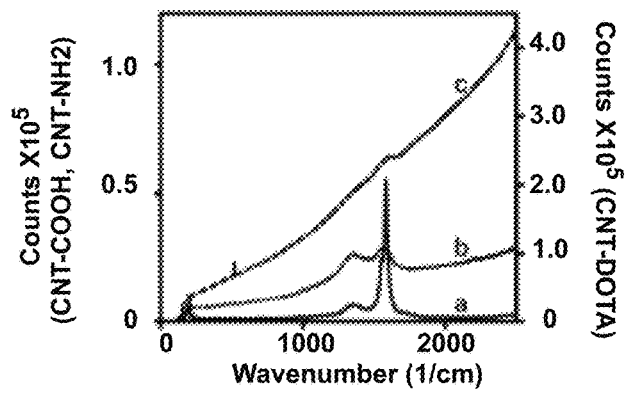
FIG. 1 depicts a Raman spectra measured with a 488 nm laser. Line a is the spectrum of the acid oxidized and purified SWNTs. Line b is the spectrum for the sidewall amine-functionalized SWNT-NH$_2$, compound 5. Line c is the spectrum of the DOTA-functionalized SWNT-NH2-DOTA, compound 6. The line spectra a and b are plotted on the left axis (0-120,000), and line spectrum c on the right axis (0-450,000).

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "functional SWNT" refers to a single wall nanotube (SWNT) that has a functional pendant moiety or handle, such as a sidewall amine or aldehyde carbonyl, suitable for bioconjugation. Functional sidewall moieties may be added via nitrone cycloaddition reactions.

As used herein, "M*" refers to a chelatable radiometal or other radionuclide or a chelatable contrast agent such as a nonradioactive nuclide useful as therapeutics for or diagnostics of a pathophysiological condition.

As used herein, "SWNT-M*DOTA" refers to a solubilized, functionalized SWNT construct comprising a functionalized group or handle to which the bifunctional chelator DOTA, and thereby the chelated radionuclide or contrast agent, M*, is directly linked. Similarly, SWNT-peptide or SWNT-IgG refers to a construct to which a peptide or antibody is appended to a maleimide linker. Thus, SWNT-peptide-M*DOTA or SWNT-IgG-M*DOTA is a functionalized SWNT with stoichiometric amounts of both peptide or antibody and M*DOTA appended via the maleimide linker and functionalized group or handle, respectively.

As used herein, "SWNT-(DNA$_{1,2}$-(cDNA$_1$-peptide)$_m$-(cDNA$_2$-M*DOTA)$_n$)$_x$" refers to a solubilized, functionalized SWNT construct comprising an x number of DNA$_{1,2}$ platforms linked to a functional handle on an SWNT. An m number of targeting moieties (cDNA$_1$-peptide) and an n number of therapeutic moieties or payloads (cDNA1-M*DOTA) are linked to their respective complementary regions on DNA$_{1,2}$. DNA$_{1,2}$ refers to an oligodeoxynucleotide with a sequence complementary to cDNA$_1$ which is linked by a PEG molecule or other linker to another oligodeoxynucleotide with a sequence complementary to cDNA$_2$. It is to be noted that reference to these compositions or components thereof may use a shorthand, such as, SWNT-(DNA-(Peptide)$_m$-(M*DOTA)$_n$)), however the construction of the SWNT composition still requires linking the peptide and the M*DOTA to oligodeoxynucleotides complementary to the DNA.

In one embodiment of the present invention there is provided a method of treating a pathophysiological state in a subject, comprising administering a soluble SWNT functionalized with a plurality of a targeting moiety and a plurality of one or more payload molecules attached thereto; targeting cells associated with the pathophysiological state with the targeting moiety; and delivering the payload to the associated cells, where the payload has a therapeutic effect against the cells or elicits a therapeutic effect from the cells thereby treating the pathophysiological state in the subject.

In one aspect of this embodiment the soluble SWNT has the structure SWNT-((peptide)$_m$-(M*DOTA)$_n$)$_x$, where x is 1 to 300; m and n are independently 1 to 300; and M* is a therapeutic radionuclide. Further to this aspect the soluble SWNT comprises oligomers linked independently to the SWNT, the peptide and DOTA. Examples of oligomers are DNA, RNA, PNA, or PSDNA. The structure of the soluble SWNT may be SWNT-(DNA$_{1,2}$-(cDNA$_1$-peptide)$_m$-(cDNA$_2$-M*DOTA)$_n$)$_x$, where cDNA$_1$ and cDNA$_2$ independently are non-identical oligomers and DNA$_{1,2}$ is an oligomer with a sequence complementary to cDNA$_1$ and cDNA$_2$. In this further aspect the cDNA$_1$ and cDNA$_2$ may have about 8 to about 100 oligonucleotides and DNA$_{1,2}$ may have about 16 to about 200 oligonucleotides. Also in this further aspect DNA$_{1,2}$ may have the sequence shown in SEQ ID NO: 1, cDNA$_1$ may have the sequence shown in SEQ ID NO: 2 and cDNA$_2$ may have the sequence shown in SEQ ID NO: 3.

In another aspect of this embodiment the targeting moiety is the payload. In this aspect the payload may be a peptide and the soluble SWNT construct may have the structure SWNT-peptide. Also, in this aspect the payload peptide elicits a peptide-specific or heteroclitic immune response against cancer cells. The payload peptide may be a native or a heteroclitic WT1 specific peptide epitope. A native epitope may have the sequence shown in SEQ ID NO: 15, 17, 19, 21, 23, 25, 27, 29, 31, or 33. A heteroclitic epitope may have the sequence shown in SEQ ID NO: 16, 18, 20, 22, 24, 26, 28, 30, 32, or 34.

In yet another aspect of this embodiment the payload molecules are one or more enzymes effective to activate a prodrug, a preprodrug or a combination thereof whereby the soluble SWNT construct is self-assembling in situ proximate to the cancer-associated cells upon delivery of components comprising said SWNT construct thereto. Further to this aspect the method comprises administering a prodrug or a preprodrug to the subject. An example of a preprodrug is doxorubicin.

In these two aspects the targeting moiety may be a peptide such that the construct components are SWNT-(peptide)-(DNA$_1$)$_x$-(DNA$_2$)$_x$, and (cDNA$_1$-E$_1$)$_m$ or (cDNA$_1$-E$_1$)$_m$ and (cDNA$_2$-E$_2$)$_n$, and the self-assembled SWNT construct having the structure SWNT-(peptide)$_x$-(DNA$_{1,2}$-(cDNA$_1$-E$_1$)$_m$-(cDNA$_2$-E$_2$)$_n$)$_x$, where x is 1 to 300, m and n are independently 1 to 300, cDNA$_1$ and cDNA$_2$ are non-identical oligonucleotides, DNA$_1$ and DNA$_2$ are oligonucleotides with sequences complementary to cDNA$_1$ and cDNA$_2$, and E1 and E2 are enzymes. The self-assembled SWNT construct comprises an enzymatic nanofactory. Also in these aspects the cDNA$_1$ and cDNA$_2$ may have about 8 to about 100 oligonucleotides and DNA$_{1,2}$ may have about 16 to about 200 oligonucleotides. As examples cDNA$_1$ has the sequence shown in SEQ ID NO: 2 and cDNA$_2$ has the sequence shown in SEQ ID NO: 3. Furthermore, E$_1$ is carboxypeptidase A and E$_2$ is β-glucuronidase.

In yet another aspect of this embodiment the targeting peptide is a targeting therapeutic antibody and the payload is a diagnostic radionuclide such that the method further comprises imaging a location of said targeting therapeutic antibody after administering the soluble SWNT. In this aspect the therapeutic targeting antibody is rituximab and the diagnostic radionuclide is yttrium-86.

In all aspects of this embodiment targeting peptide is an antibody or fragment thereof or other peptide ligand. An example of an antibody is rituximab, trastuzumab, or antinucleolin. An example of a peptide ligand is cyclic RGD or an NGR peptide. Also, in all aspects the payload may be a radionuclide, one or more peptides or one or more enzymes. An example of a radionuclide is actinium-225, astatine-211, indium-111, technetium-99, lutetium-177, gallium-68, holmium-166, bismuth-212, bismuth-213, yttrium-86, yttrium-90, copper-64, copper-67, samarium-117, samarium-153, iodine-123, iodine-124, iodine-125, or iodine-131. Furthermore, the cells associated with the pathophysiological state may be cancer cells, vascular endothelial cells or activated T cells. An example of a pathophysiological state is a cancer.

In another embodiment of the present invention there is provided a method of eliciting an immune response against a cancer in a subject, comprising administering a soluble SWNT construct having a plurality of one or more cancer-specific peptides comprising native or heteroclitic epitope sequences linked thereto to the subject; and activating T cells against cells comprising the cancer via presentation of said epitopes by antigen-presenting cells thereby eliciting the immune response against the cancer in the subject. In this embodiment the epitope may be the native or a heteroclitic WT1 specific peptide epitopes described supra. The sequences of the native or heteroclitic epitopes are as described supra.

In yet another embodiment of the present invention there is provided a method of delivering an anticancer drug in situ to a cancer in a subject, comprising administering a first component of a soluble SWNT construct having the structure SWNT-(peptide)$_x$-(DNA$_1$)$_x$-(DNA$_2$)$_x$, such that the peptide targets cells comprising the cancer; administering a second construct component having the structure cDNA$_1$-E$_1$)$_m$ and a third construct component having the structure (cDNA$_2$-E$_2$)$_n$, self-assembling the soluble SWNT construct in situ via hybridization of the second and third construct components to the first construct component, where self-assembled SWNT construct having the structure SWNT-(peptide)$_x$-(DNA$_{1,2}$-(cDNA$_1$-E$_1$)$_m$-(cDNA$_2$-E$_2$)$_n$)$_x$, where x is 1 to 300; m and n are independently 1 to 300; cDNA$_1$ and cDNA$_2$ are non-identical oligonucleotides; DNA$_1$ and DNA$_2$ are oligonucleotides with sequences complementary to cDNA$_1$ and cDNA$_2$; and E$_1$ and E$_2$ are enzymes; administering an anticancer preprodrug to the subject; and activating the drug via sequential action of the enzymes on the preprodrug thereby delivering the anticancer drug in situ to the cancer in the subject. In this embodiment the self-assembled SWNT construct comprises an enzymatic nanofactory. Also, The DNA$_1$, DNA$_2$, DNA$_{1,2}$, cDNA$_1$, and cDNA$_2$ may be as described supra. Furthermore, in this embodiment E$_1$ may be carboxypeptidase A and E$_2$ may be β-glucuronidase. An example of a preprodrug is preprodoxirubicin.

In yet another embodiment the present invention there is provided a soluble SWNT construct having the structure SWNT-((peptide)$_m$-(M*DOTA)$_n$)$_x$, where x is 1 to 300; m and n are independently 1 to 300; and M* is a radionuclide or a contrast agent. Further to this embodiment the soluble SWNT construct may have oligomers comprising DNA, RNA, PNA, or PSDNA linked independently to the SWNT, the peptide and DOTA. The soluble SWNT construct may have the structure SWNT-(DNA$_{1,2}$-(cDNA$_1$-peptide)$_m$-(cDNA$_2$-M*DOTA)$_n$)$_x$, where cDNA$_1$ and cDNA$_2$ independently are non-identical oligomers and DNA$_{1,2}$ is an oligomer with a sequence complementary to cDNA$_1$ and cDNA$_2$. In this further embodiment cDNA$_1$ and cDNA$_2$ may have about 8 to about 100 oligonucleotides and DNA$_{1,2}$ may have about 16 to about 200 oligonucleotides. Also, DNA$_{1,2}$ may have the sequence shown in SEQ ID NO: 1, cDNA$_1$ may have the sequence shown in SEQ ID NO: 2 and cDNA$_2$ may have the sequence shown in SEQ ID NO: 3. In these embodiments the radionuclide and contrast agent may be as described supra. Also, the peptide may be those antibodies or fragments thereof or other peptide ligands as described supra. In a related embodiment there is provided a soluble SWNT construct having the structure SWNT-((rituximab)$_m$-($^{86}$Y*DOTA)$_n$)$_x$, wherein x is 1 to 300 and m and n are independently 1 to 300.

In yet another embodiment of the present invention there is provided a method of locating or diagnosing a cancer in a subject, comprising administering the soluble SWNT construct as described supra where the peptide is a targeting antibody or fragment thereof or other targeting peptide ligand and M* is a diagnostic radionuclide or contrast agent; targeting cells comprising the cancer with the peptide of the SWNT construct; and detecting localization of the diagnostic radionuclide or contrast agent in the subject thereby locating or diagnosing the cancer. In this embodiment the diagnostic radionuclide may be indium-111 or yttrium-86 and the contrast agent may be gadolinium as described for the soluble SWNT construct. Also in this embodiment the peptide may be those antibodies or fragment thereof or other peptide ligands as described supra.

In yet another embodiment of the present invention there is provided a method of treating a cancer in a subject, comprising administering the soluble SWNT construct as described supra where the peptide is a targeting antibody or fragment thereof or other targeting peptide ligand and M* is a therapeutic radionuclide; targeting cells associated with the cancer with the peptide of the SWNT construct; and delivering the therapeutic radionuclide to the cancer-associated cells such that the radionuclide has an anticancer effect against the cells thereby treating the cancer in the subject.

In this embodiment the soluble SWNT further may comprise oligonucleotides linked independently to the SWNT, the peptide and DOTA and having the structure SWNT-(DNA$_{1,2}$-(cDNA$_1$-peptide)$_m$-(cDNA$_2$-M*DOTA)$_n$)$_x$, where cDNA$_1$ and cDNA$_2$ independently are non-identical oligonucleotides and DNA$_{1,2}$ is an oligonucleotide with a sequence complementary to cDNA$_1$ and cDNA$_2$ as described supra for the SWNT construct where the DNA$_1$, DNA$_2$, DNA$_{1,2}$, cDNA$_1$, and cDNA$_2$ also may be as described supra. Also in this embodiment the peptide may be those antibodies or fragment thereof or peptide ligands as described supra. Furthermore, the radionuclide may be as described supra. The cancer-associated cells may be cancer cells or endothelial cells of the vasculature associated with the cancer.

Provided herein are soluble and functionalized single wall nanotube compositions that are effective as a diagnostic or tracer, an immunogenic or radioimmunogenic, radiotherapeutic, chemotherapeutic, anti-angiogenic or other therapeutic agent. Soluble and functionalized SWNTs per se are scalable, while retaining key properties. They are inert, stable, flexible, non-immunogenic and non-toxic. Thus, they can be used as platforms upon which to construct a diagnostic or therapeutic vehicle. The soluble SWNTs of the present invention are therefore useful in locating, diagnosing and/or treating a pathophysiological state in a subject, preferably in a mammal, more preferably in a human.

The soluble SWNTs of the present invention may have a length of about 2000 nm or less, preferably about 1000 nm or less, more preferably about 250 nm or less. The SWNTs comprise cycloadducts with long polar tails as functional handles, such as PEG hydroxylamines, PEG aldehydes or PEG dialdehydes, to which various functional groups, such as, but not limited to, antibodies, peptides, fluorescent moieties, tracer labeled ligands or chelated radionuclides or non-radioactive nuclides, may be attached. A stoichiometric combination of functional groups, such as an antibody, antibody fragment or other peptide and a chelated radionuclide, contrast agent or fluorescent moiety, may also be used. A preferred soluble and functionalized SWNT construct may have the general structure SWNT-((peptide)$_m$-(M*DOTA)$_n$)$_x$.

Alternatively, an oligomer, for example, a DNA, a RNA, a peptide nucleic acid (PNA), a phosphorothioate DNA (PSDNA), or other nucleic acid, may be linked to the handle which provides a platform upon which to attach one or more of the functional groups. The oligomer may comprise two shorter oligomers of different sequences linked by one or more PEG molecules. For example, an oligomeric platform (DNA$_{1,2}$) comprises first (DNA$_1$) and second (DNA$_2$) oligonucleotides linked by PEG to the SWNT handle (SWNT-DNA$_{1,2}$). Or DNA$_1$ and DNA$_2$ are linked separately to the SWNT.

This construct provides a platform upon which to link different functional groups, e.g., a targeting moiety and a therapeutic moiety or payload. For example, with a platform comprising DNA, the functional groups are linked independently to cDNAs with a sequence complementary to either DNA$_1$ or DNA$_2$ which, upon hybridization thereto with suitable stoichiometry, forms the functionalized SWNT. The cDNAs may comprise about 8 to about 100 nucleotides and the DNA platform would therefore comprise about 16 to about 200 nucleotides.

It also is contemplated that an SWNT construct may comprise a targeting moiety, such as a peptide, linked directly thereto. This soluble construct would have the structure SWNT-peptide. Alternatively, a soluble SWNT construct may comprise a targeting moiety and one or more therapeutic moieties attached with suitable stoichiometry via one or more oligomeric platforms. The targeting moiety may be, but not limited to, an antibody, antibody fragment or other peptide. Alternatively, the targeting moiety may be the payload, e.g., a peptide effective to target a cell and elicit an immune response. A preferred SWNT construct is SWNT-(DNA$_{12}$-(cDNA$_1$-peptide)$_m$-(cDNA$_2$-M*DOTA)$_n$)$_x$ where x, m, and n indicate the stoichiometric amounts of each component of the construct. In preferred stoichiometries x, m and n are independently about 1 to about 300. The targeting moiety may be any molecule or construct effective to selectively target cells of interest.

The SWNT construct may comprise an enzymatic nanofactory and be assembled sequentially in situ at or near a site of interest, e.g., a tumor. Nanofactories are suitable to activate prodrugs or preprodrugs at the site of interest thereby reducing or eliminating toxicity from systemic administration. A component construct of general structure SWNT-antibody-DNA$_1$-DNA$_2$ is administered and targeted to the site of interest. Pre-pro-(E$_1$) and pro-drug (E$_2$) enzymes are linked individually to other component constructs cDNA$_1$ (cDNA$_1$-E$_1$) and cDNA$_2$ (cDNA$_2$-E$_2$) and delivered to the site of interest where, upon colocalization with the SWNT-antibody-DNA$_1$-DNA$_2$ construct, self-assembly with DNA$_1$ and DNA$_2$ occurs.

A self-assembled SWNT construct useful as an enzymatic nanofactory may have the structure SWNT-(peptide)$_x$-(DNA$_1$-(cDNA$_1$-E$_1$)$_m$-(cDNA$_2$-E$_2$)$_n$)$_x$. The cDNA$_1$ and cDNA$_2$ may have the respective sequences shown in SEQ ID NOS: 1 and 2. DNA1 and DNA2 have sequences complementary to cDNA$_1$ and cDNA$_2$. In the presence of the pre-pro-drug, the enzymes act sequentially to activate the drug. It is contemplated that assembly with a single enzyme would be effective for prodrug activation.

As such, the present invention also provides methods of delivering an anticancer drug in situ to a cancer utilizing a targeted prodrug approach. Use of the enzymatic nanofactory described herein is effective for delivering an anticancer drug without the concomitant toxic effects that may occur with systemic administration. The enzymatic nanofactory provides a means of assembling a soluble SWNT construct which, if fully assembled prior to administration, would be too big for and therefore ineffective as a chemotherapeutic. Once self-assembled in situ a prodrug or preprodrug, such as, but not limited to, preprodoxirubicin, which is not toxic per se, is administered. The action of the enzymes comprising the nanofactory activate the doxorubicin in situ at the site of the cancer.

A soluble SWNT construct of structure SWNT-((peptide)$_m$-(M*DOTA)$_n$)$_x$ may be useful in locating a potential cancer or tumor or an existing cancer and thus serve as a diagnostic tool. M* may be a diagnostic or tracer radionuclide, such as indium-111 or yttrium-86, or may be a contrast agent, such as gadolinium. It is contemplated that any radionuclide or contrast agent suitable to form the construct may be used. The peptide may be a targeting peptide such as an antibody or fragment thereof or other targeting peptide ligand specific for the particular cancer. Localization of the diagnostic or tracer radionuclide or contrast agent within a specific tissue indicates presence of a cancer. Alternatively, a fluorescent moiety may be substituted for the M*DOTA or may be linked to the SWNT in combination therewith.

As such, the soluble SWNT constructs of the present invention also are effective as therapeutics in methods for treating a pathophysiological state, such as a cancer. Therapeutic radionuclides may be delivered to cancer cells using the SWNT-((peptide)$_m$-(M*DOTA)$_n$)$_x$ construct or the SWNT-(DNA$_{12}$-(cDNA$_1$-peptide)$_m$-(cDNA$_2$-M*DOTA)$_n$)$_x$ construct. DNA$_{1,2}$ may have the sequence shown in SEQ ID NO: 1 and cDNA1 and cDNA2 may have the sequences shown in SEQ ID NO: 1 and 2, respectively.

In these therapeutic constructs the radionuclide may be, but not limited to, actinium-225, astatine-211, indium-111, technetium-99, lutetium-177, gallium-68, holmium-166, bismuth-212, bismuth-213, yttrium-86, yttrium-90, copper-64, copper-67, samarium-117, samarium-153, iodine-123, iodine-124, iodine-125, or iodine-131. The peptide may be a targeting antibody or fragment thereof, such as, but not limited to, rituximab, trastuzumab, or antinucleolin. Alternatively, the peptide may be another targeting peptide ligand such as, but not limited to, a cyclic RGD or an NGR peptide that are effective to target endothelial vasculature associated with the cancer.

In addition a soluble SWNT construct may comprise one or more targeting peptides that are also payload or therapeutic peptides. The construct may have the structure SWNT-(peptide)$_x$ where the peptides are one or more cancer-specific peptides comprising native or heteroclitic epitope sequences. These sequences are effective to activate T cells against cancer via presentation of the epitopes by antigen-presenting cells. For example, these peptides may be native or heteroclitic WT1 specific peptide epitope. The native epitopes may have a sequence shown in SEQ ID NOS: 15, 17, 19, 21, 23, 25, 27, 29, 31, or 33. The heteroclitic epitopes may have a sequence shown in SEQ ID NOS: 16, 18, 20, 22, 24, 26, 28, 30, 32, or 34. Thus, the present invention provides a method of eliciting an immune response against a cancer.

Furthermore, soluble SWNT constructs may comprise both a targeting peptide with therapeutic efficacy, e.g., a therapeutic antibody such as, but not limited to, rituximab or trastuzumab, and a diagnostic radionuclide, such as but not limited to, yttrium-86 or indium-111. Preferably, for the general structure SWNT-((peptide)$_m$-(M*DOTA)$_n$)$_x$, the therapeutic antibody is rituximab and the diagnostic radionuclide is yttrium-86.

The following examples are given for the purpose of illustrating various embodiments of the invention and are not meant to limit the present invention in any fashion.

Example 1

Length Adjustment, Solubilization and Functionalization of SWNTs

Length Adjustment: Method I

Raw single walled carbon nanotubes (SWNT) about 1.4 nm in diameter were shortened to uniform length by oxidative acid digestion. Briefly, 60 mg of SWNT (Nanostructured & Amorphous Materials, Los Alamos, N. Mex.) were refluxed in concentrated 2M HNO$_3$ (60 mL) for 48 hours. This digestion yields SWNT molecules with carboxy-functionalized termini. Shortening SWNT lengths to 250 nm and below requires sonication in addition to the refluxing. Sonication for 0.5 h was performed at 70° C. with 100 watts with a Biologics model 300 V/T Ultrasonic Homogenizer using the ⅜-in-diameter stepped titanium tip. The SWNT were then refluxed for an additional 10 h in the concentrated 2M HNO$_3$. Acid reflux also removes residual metal catalyst from the tubes. It is generally believed that sonication-assisted shortening proceeds via the collapse of cavitation bubbles, generating local hot-spots, that create an array of defects along the SWNT side-walls, thus providing sites where oxidation-assisted tube-cleavage and shortening takes place. The Raman spectrum product is shown in FIG. 1, line a. The radial breathing mode (RBM) feature at 200 cm$^{-1}$ yields a SWNT diameter of 1.1 nm and further confirmation of the product identity is provided by the 1340 cm$^{-1}$ disorder band (D band) and the sharp 1556 and 1584 cm$^{-1}$ tangential mode (G band) resonances.

Length Adjustment: Method II

Alternatively, 20 mg of purified HiPCO SWNTs (Carbon Nanotechnologies, Houston Tex.) and SWNTs (Nanostructured & Amorphous Materials, Los Alamos, N. Mex.) were dispersed in 50 mL dimethylformamide (DMF, Aldrich) and sonicated (bath sonicator) at room temperature for 30 minutes. Samples of SWNT are analyzed using Atomic force microscopy to obtain images and ascertain the approximate lengths following an oxidative acid digestion process Functionalization & Solubilization with Sidewall Amino Groups: Method I An azomethine ylide cycloaddition reaction is utilized to functionalize the sidewalls of single wall carbon nanotubes (SWNT) (8). Commercially available 2,2'-(ethylenedioxy)-bis-[ethylamine] was asymmetrically modified using Boc-anhydride. The resulting monoprotected diamine 1 was alkylated with benzyl bromoacetate 2 and converted to a debenzylated glycine derivative 3. This was added to a suspension of SWNT in N,N-DMF and 120 mg of para-formaldehyde (Aldrich Chemical Co., Milwaukee, Wis.) and the mixture was heated to 130° C. Subsequently, 120 mg of the BOC protected amino acid, 120 mg dissolved in 12 mL DMF, was added in six additions (2 mL every 24 hours) and the reaction mixture refluxed for a total of 120 hours. The mixture was cooled to room temperature and the unreacted SWNT were removed by a combination of centrifugation (3000 rpm, 5 minutes) and filtration (10 m TEFLON, Aldrich Chemical Co.).

Figure 2A:
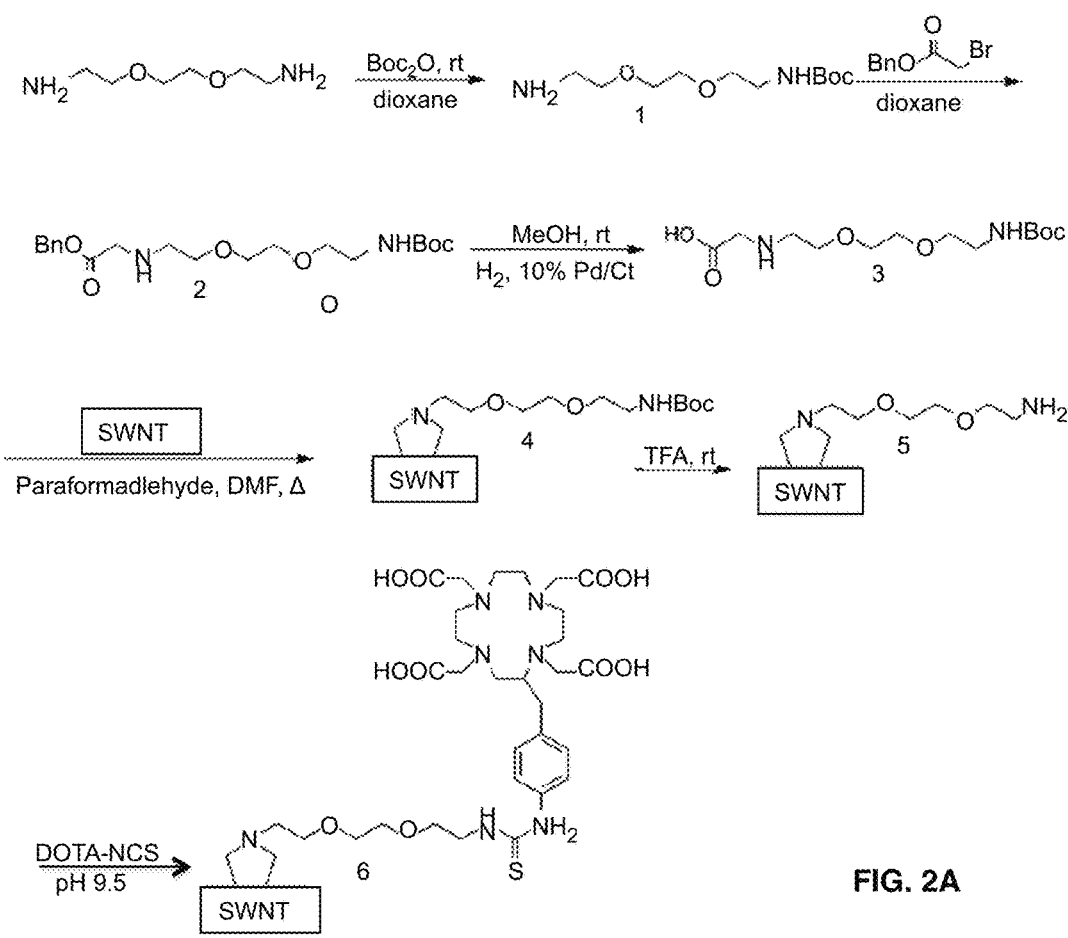
FIGS. 2A-2C depict synthetic schemes for functionalizing SWNTs.

The solvent was evaporated to dryness leaving behind a brownish oily residue, which was subsequently dissolved in chloroform and extracted repeatedly with metal free water to remove the unreacted amino acid and aldehyde. The product 4 was isolated in $CHCl_3$ and was dried over sodium sulfate and the solvent evaporated to dryness. The final work up was done by precipitating the amine functionalized SWNTs in diethylether followed by the BOC de-protection in 0.3 mL of trifluoroacetic acid (TFA) for 6 hours. The excess TFA was removed and the remaining brown solid was SWNT-$NH_2$ 5 and was found to be completely soluble in water and a number of polar organic solvents (FIG. 2A). The Raman spectrum of 5 (FIG. 1, line b) was characterized by the loss of the RBM feature and a rising baseline due to increasing luminescence resulting from the enhanced dispersion of this product in solution. The soluble 5 was examined by Atomic Force Microscopy (AFM) using a model MFP-3D microscope (Asylum Research), and the moles of amine per gram SWNT were quantified spectrophotometrically (56). A distribution of lengths, ranging from 200 to 1,000 nm, as well as some aggregated bundles with diameters not greater than 10 nm were observed. Individual SWNT had a diameter of 1.4 nm. The amine content of SWNT-$NH_2$ was determined to be 1.76 mmol amines per gram SWNT.

Functionalization & Solubilization with Sidewall Amino Groups: Method II

Figure 2B:
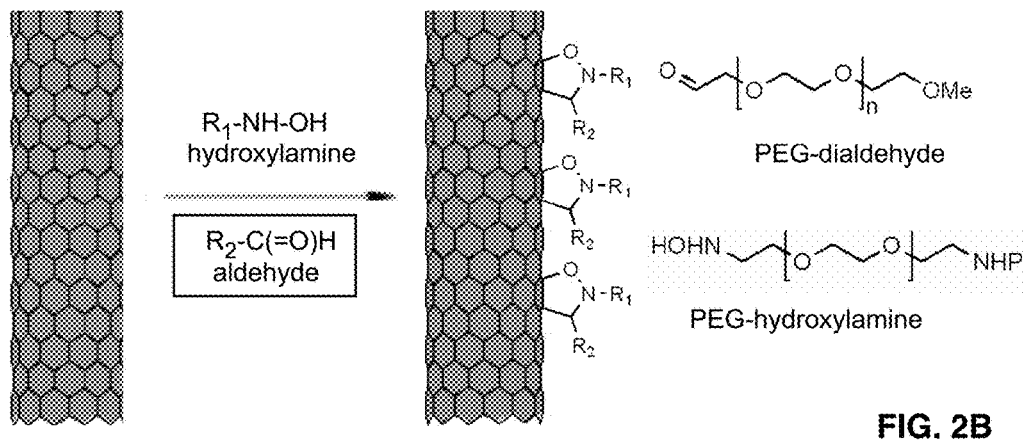

Nitrone cycloaddition reaction is utilized to functionalize the sidewalls of single wall carbon nanotubes (SWNT) (9). The nitrone cycloaddition reaction uses readily accessible starting materials, e.g., an aldehyde and a hydroxylamine (FIG. 2B). The reaction itself is very simple to execute and has proven to be quite robust. Each cycloaddition offers two sites of functionalization via the aldehyde and the hydroxylamine groups. A polyethylene glycol (PEG) may be used as a linker for the hydroxylamine moiety, with the other terminus of the PEG linker decorated as a protected amine. This amine serves as a handle for attachment of biomolecules. The aldehyde functional group ($R_2CHO$) also may serve as a handle. For example, a trifluoromethyl (—$CF_3$) or a polyfluoro functionalized aldehyde may be used. The fluorine group can be used as a spectroscopic (NMR) handle during characterization of the nanotubes (10).

Functionalization & Solubilization with Sidewall Amino Groups: Method III

Alternatively, an aldehyde with a functional handle that differs from the amino group, which may be orthogonally protected, while still being chemically orthogonal. These different handles allow selective functionalization of the two end groups with various functional groups, such as, but not limited to, antibodies, tracer labeled ligands or chelated radiometals. For example, the aldehyde end group first may be functionalized with a small radiopharmaceutical or a cytotoxic prodrug. This first selective functionalization is followed with antibody conjugation via the remaining free amino termini.

Figure 2C:
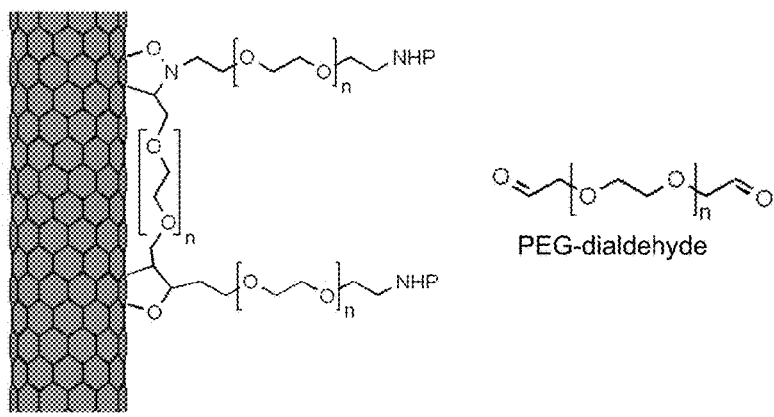

The aqueous solubility of these SWNTs may be improved further with PEG functionalized aldehydes. Various aldehydes with different number of PEG units may be used provided that the aqueous solubility of their representative cycloadducts is sufficient. Furthermore, two aldehydes linked by a PEG tether, that is, a PEG-dialdehyde, may be used. In this case, the first nitrone cycloaddition is followed by an intramolecular nitrone cycloaddition (FIG. 2C). The length of the PEG tether is optimized to yield the tandem sequence.

These SWNT constructs have long polar tails from each successful nanotube cycloaddition and a PEG coating between each pair. The extra PEG coating on the SWNT significantly increases the aqueous solubility of the functionalized nanotubes. This tethered approach enables access to different functional patterns on the surface of the SWNT compared to the intermolecular nitrone cycloaddition approach. The different functional patterns on carbon nanotubes of varying lengths may provide means for optimizing SWNT constructs. It is contemplated that using microwaves (11-12) improves the synthetic efficiency of cycloaddition nanotube sidewall functionalization.

Derivatization of SWNT-$NH_2$ with DOTA and/or Maleimide

Figure 3:
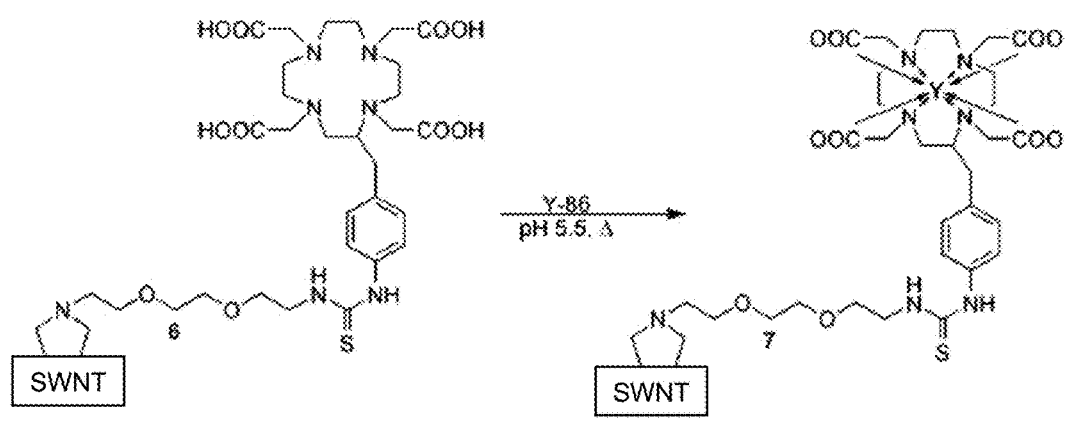
FIG. 3 depicts a synthetic scheme for chelating $^{86}$Yttrium to functionalized SWNTs using the SWNT construct 6 in FIG. 1A.

The SWNT-amine construct 5 in Example 1 was reacted with the bifunctional chelate 2-(p-isothiocyanatobenzyl)-1,4,7,10-tetraazacyclododecane-1,4,7,10-tetra acetic acid (DOTA-NCS, Macrocyclics, Inc., Dallas, Tex.) to yield a DOTA-SWNT construct. The DOTA-NCS was attached to the CNT via a thiourea linkage, which is quite stable under physiologic conditions in vivo and in vitro (57). Buffers, reagents, and chromatographic media were rendered metal free (58) to prepare CNT-($NH_2$)(DOTA). Briefly, 20 mg of SWNT-$NH_2$ (1.76 mmol amine per gram CNT) in metal-free water (MFW) were mixed with 0.05 mmol of DOTA-NCS at pH 9.5 in a 1 mM bicarbonate buffer for 30 min at room temperature (0.7 amine:1 DOTA-NCS). The product was purified using a 10DG column (BioRad) with MFW as the mobile phase. The SWNT-$NH_2$-DOTA product 6 (FIG. 3) was lyophilized to give a solid powder.

Raman characterization of SWNT-$NH_2$-DOTA 6 (FIG. 1, line c) confirmed the enhanced solubility (10 g/L) of this construct by the rising baseline, which partially masks the D and G bands. The DOTA content of 6 was determined using a lead arsenazo assay (59), which yielded a value of 0.30 mmol DOTA/g SWNT; in addition 3 still contained some unreacted amines assayed to be 0.27 mmol amine/g SWNT.

Addition of Maleimides: SWNT-DOTA-Mal Constructs

The pendant amine functionalities on SWNT-($NH_2$) 5 or remaining pendant amines after DOTA derivatization on the SWNT-($NH_2$)(DOTA) 6 are derivatized as maleimides by reaction with heterobifunctional crosslinker succiniminidyl-4-(maleimidomethyl) cyclohexane-1-carboxy-(6-amido-caproate) (LC-SMCC) or BMPS (N-[β-Maleimidopropyloxy] succinimide ester) (Pierce) in anhydrous DMF. Anhydrous DMF allows enhancement of the reaction yields by preventing the hydrolysis of the N-hydroxysuccinimide group on the chelator and also allows the reaction to be carried out in extremely small volumes (<100 μL), since both the chelator and the $NH_2$ terminated SWNTs are soluble in DMF. The SWNT construct is purified from the excess reagent by using a 10DG column with a 5 mM ethylenediaminetetracetic acid/phosphate-buffered saline (EDTA/PBS) buffer, pH 6.4 mobile phase or by dialysis using special regenerated cellulose membrane compatible with organic solvents (Membrane Filtration Products).

The extent of maleimide functionalization is determined by trace labeling with $^{35}$S-labeled cysteine. The malimide-functionalized SWNTs, SWNT-(Mal) or SWNT-(DOTA)(Mal), in aqueous solution (0.300 mg, 0.4 nmol) is mixed with cysteine (0.070 mg, 400 nmol) containing trace amounts of $^{35}$S-cysteine. The pH is adjusted to 7.0 using sodium carbonate, and after 30 minutes at room temperature, the excess cysteine is removed by size-exclusion chromatography. An aliquot of the cysteine labeled SWNTs product fraction is counted in a β-scintillation counter, and by comparison with an aliquot of the $^{35}$S-cysteine/cold cysteine solution, the total amount of cysteine bound to the Mal-SWNT is calculated. Using the Mal-SWNT concentration, the amount of maleimide residues per SWNT is determined. Typical numbers are between 200-300 maleimide/SWNT, the maximum achievable is ~600. The cysteine assay indicated that 0.09 mmol maleimide per gram SWNT had been incorporated onto SWNT-(DOTA)(Mal). It was determined that there were 5-7 thiols introduced per antibody. The maleimide functionalized SWNTs can be lyphilized and stored a −80° C. to prevent deactivation of maleimide groups.

Purification

For in vivo applications the products must be further purified from the deprotected BOC groups and any other small molecular weight byproducts. The product either is dialiyzed overnight in deionized water using a cellulose acetate membrane, 3000 MW cutoff or is purified through a centricon with a 3000 MW cutoff for 2 hours at 14000 rcf. The final purified product is lyophilized, weighed and resuspended in de-ionized water or other buffers. The amount of amine groups present on the surface of SWNT is quantified using the colormetric flourescamine assay which detects primary amines (13). On average, a concentration of 0.3-0.5×10$^{-3}$ mole NH$_2$/g SWNT is achieved.

Purification also may be accomplished by using the carboxy groups at the nanotube ends. The carboxy groups are linked via an ester bond, preferably, a benzyl ester, to a solid support. When the reaction is done, simple filtration removes all the unreacted reagents. The benzyl ester linkage is chosen to match the amine protection, benzyl carbamate (CBZ).

Analysis of the constructs is performed by size exclusion chromatography, using a Beckman Coulter System Gold Bioessential HPLC, equipped with a Tosoh Bioscience TSK-GEL G3000SWXL analytical column. The eluent is a buffer containing 0.15 M sodium chloride, 0.02 M sodium acetate, and 0.05% (w/v) sodium azide at pH 7.0. The column is equilibrated in the mobile phase. Each construct is diluted in the mobile phase and injected for a 40 min run at 1 mL/min at 4 degrees Celsius. Detection of the peaks is performed using a Beckman Coulter 168 diode array detector, allowing to extract chromatograms at any wavelength comprised between 190 nm and 590 nm. Detection of fluorescent compounds is performed simultaneously using a Jasco FP-2020 fluorescence detector. Data is analyzed using the 32 Karat software.

Upon hydrogenation with solid supported palladium, the functionalized nanotube is released cleanly from the support and also is relieved of its nitrogen protecting group. Simple filtration separates the solid support and the solid supported reagent from the desired soluble nanotube construct. The Boc protecting group may be replaced with a CBZ or a CBZ-like group. This allows hydrogen to be used for the deprotection of solid supported palladium. This purification only involves filtration to remove solid supported reagents and evaporation of CO2 and toluene. As the nanotubes produced are very water soluble, other organic impurities may be removed via the aqueous solubility.

Example 2

Derivatizing SWNT-DOTA-Mal with Antibodies and Fragments, DNA or PNA

Rituximab or Lintuximab (HuM195)

Controlled introduction of free sulfhydryl (—SH) groups into an antibody, e.g., rituximab (Genentech, Inc.) or lintuximab (HuM195; Protein Design laboratories), is accomplished by reaction of the antibody with 2-iminothiolane-HCl (Traut's reagent). Briefly the protein was dissolved in PBS containing 5 mM EDTA buffer. Depending on the level of thiolation desired, a 2 to 20 molar excess, preferably a 10 molar excess, of Traut's reagent was added. Briefly, a 10-fold molar excess of Traut's reagent (Pierce Biotechnology, Inc.) was added to 2 mg of antibody in 0.25 ml PBS/5 mM EDTA buffer and the pH was increased to 8-9 with 1M bicarbonate buffer. The reaction proceeds for 1 hour at ambient temperature. The thiolated antibody is purified from the excess Traut's reagent by a 10DG size exclusion column (Bio-Rad). The number of reactive thiol groups that were appended onto the antibody was determined by Ellman's assay (14).

Alternatively, synthetic peptides with an N or a C terminal cysteine residue is reduced using an immobilized disulfide reducing gel (TCEP, Pierce) to ensure the presence of free sulfhydryl (—SH) groups at the end of the peptides. All peptides are synthesized by Genemed Synthesis Inc. using fluorenylmethoxycarbonyl chemistry, solid phase synthesis and purified by HLPC. Peptides are sterile and >90% pure.

The thiolated-antibody (or peptide) is coupled with the maleimide functionalized SWNTs to generate the targeting hybrid construct. A 5-20 molar excess, typically a 10 molar excess, of thiolated antibody to SWNTs were used. Briefly, a ratio of 0.5 mmol of thiolated-antibody per gram of SWNT-DOTA-Mal (0.09 mmol maleimide per gram SWNT) is used for this reaction at ambient temperature at pH 7.5 for 2 h. After 2 h unreacted —SH groups on the protein were quenched by the addition of excess maleimidobutyric acid (Aldrich) to prevent cross-linking of the proteins amongst SWNTs. If desired, unreacted maleimide groups on the SWNTs may be quenched with cysteine. The same procedure is used to produce SWNT-HuM195-DOTA.

The SWNT-rituximab-DOTA product (and SWNT-HuM195-DOTA) was purified and characterized by high-performance liquid chromatography (HPLC) using a Beckman Coulter System Gold Bioessential 125/168 diode-array detection instrument (Beckman Coulter). A Superdex 200 stationary phase (Amersham Biosciences) and a 100 mM NaCl/40 mM Tris-HCl mobile phase at a flow rate of 0.5 mL/min were used to effect separation of the construct from any unreacted antibody and SWNT. SWNT-rituximab-DOTA also was analyzed using gel electrophoresis with a 7.5% acrylamide gel that was run under nonreducing and reducing conditions. The gels were developed with silver stain. Note that underivatized SWNT does not stain. The antibody-to-SWNT ratio was determined by a combination of (i) UV-Vis (ultraviolet-visible) spectroscopy (at 600 nm) to measure the SWNT concentration from the linear region of a standard curve of absorbance at 600 nm versus different concentrations of SWNT and (ii) the Lowry assay (determine the total protein concentration at 750 nm) to measure the antibody concentration.

SWNT-rituximab-DOTA typically eluted at 18 min, whereas the free antibody (28 min) and unreacted SWNT (42 min) eluted later. Diode-array detection of the chromatographed product fraction (18-min peak) yielded a composite spectral fingerprint of the SWNT portion of the construct (broad absorbance between 250 and 500 nm) and the antibody portion (absorbance at 280 nm). In a control experiment, the chromatographic retention times and spectral fingerprints of the individual components (Rituximab antibody and SWNT-$NH_2$) used to prepare SWNT-rituximab-DOTA were measured and confirmed these assignments.

SWNT-rituximab-DOTA (and SWNT-HuM195-DOTA) also was analyzed using gel electrophoresis run under both nonreducing and reducing conditions and yielded a pattern of several high-molecular-weight bands with protein components far larger than the molecular weight of only the reduced antibody. The gel shows a protein electrophoresis of 10×10-9 g of SWNT-anti-CD20-DOTA construct under reducing conditions in a 7.5% Tris-Hcl Bio-rad ready gel. The antibody-to-SWNT ratio was determined by a combination of UV-Vis spectroscopy to measure the SWNT concentration and Lowry assay to measure the antibody concentration. The constructs SWNT-rituximab-DOTA and SWNT-HuM195-DOTA contained 0.02 mmol antibody per gram SWNT which corresponds to six antibodies appended per 200-nm-long SWNT. These results confirmed the presence of a construct with multiple antibody molecules covalently linked to a SWNT.

These synthetic methods enables the attachment of a wide range of antibodies on the sidewalls of SWNTs with high specificity and efficiency. SWNT modified by antibodies, or tagged with heavy metals, gamma emitting tracer radiometals or fluorescent moieties, like green fluorescent proteins (GFP), can be subsequently characterized by transmission electron microscopy (TEM), gamma counting, or fluorescence microscopy, respectively, or, alternatively, with X-ray photoemission spectroscopy (XPS) and AFM to quantitate the resulting products and assay their activities in vitro and in vivo. It is contemplated that the half-life of the antibodies can be significantly increased by coupling the antibodies or antibody fragments to the SWNTs of appropriate length. Reaction schemes may have to be adapted such that the attachment sites on the antibody molecules are distant from the CDR regions and crucial sites for effector functions.

Adding DNA or PNA Oligonucleotides

The SWNTs are conjugated to the antibodies as described above, but instead of the reaction being allowed to reach completion, a 1000 molar excess SH-terminated 18-mer oligonucleotide is added to the system. This is based on the assumption that the SH-terminated oligonucleotide, which is a smaller linear moiety, would react much faster than the bulky protein molecule. Subsequent purification via 50,000 kD centricon eliminates both the unconjugated SWNT and the oligonucleotide. The retentate containing a mixture of SWNT-antibody-oligonucleotide construct and free protein is purified further to remove any free protein. The elimination of the free protein is achieved either with the QIAquick® Nucleotide Removal Kit, which involves binding the oligonucleotide complex to a silica gel protein at pH ≤7.5 and washing away the unbound protein impurities, or using analytical HPLC size exclusion chromatography. In case of the former the membrane bound SWNT-antibody-oligonucleotide construct is eluted pH 8.5 with 10 mM tris.Cl buffer. To attach both ligands, oligos are reacted first at low pH, i.e., <7.0, for 30 min and then purified.

Example 3

Derivatizing Functionalized SWNTs with Bifunctional Chelate Radiometals, Trace Labels and Markers SWNT-$^{86}$Y*DOTA Constructs $^{86}$Y was produced in the Memorial Sloan-Kettering Cancer Center cyclotron core facility via the (p,n) nuclear reaction (15-16) on an enriched strontium-86 target. 10.5 mCi of reactive $^{86}$Y in 0.05 M HCl was provided for labeling. Activity was assayed in a Squibb CRC-15R Radioisotope Calibrator (or equivalent model) (E.R. Squibb and Sons, Inc., Princeton, N.J.) set at 711 and dividing the displayed activity value by 2.

The $^{86}$Y-SWNT construct (7) was prepared by adding 8 mCi (206 Mbq) of acidic $^{86}$Y to 0.150 mg of SWNT-DOTA (10 mg/mL) in MFW and 0.050 mL of 3M ammonium acetate (Aldrich) to yield a pH 5.5 solution. The reaction mixture was heated to 60° C. for 30 min. and then purified by size exclusion chromatography using a P6 resin (BioRad) as the stationary phase and 1% human serum albumin (HSA, Swiss Red Cross, Bern, Switzerland) and 0.9% NaCl (Abbott Laboratories, North Chicago, Ill.) as the mobile phase.

The control construct was a mixture of $^{86}$Y-DOTA and SWNT-amine. This mixture was prepared by the adding 1 mCi (37 Mbq) of acidic $^{86}$Y to 0.5 mg (10 mg/mL in MFW) of 1,4,7,10-tetraazacyclododecane-1,4,7,10-tetraacetic acid (DOTA, Macrocyclics, Inc.) and 0.050 mL of 3M ammonium acetate to yield a pH 5.5 solution. The reaction mixture was heated to 60° C. for 30 min. and then purified by size exclusion chromatography as described above. 0.150 mg of SWNT-amine in MFW was added to the $^{86}$Y*DOTA solution and mixed.

A small aliquot of each final product was used to determine the radiochemical purity by ITLC-SG using silica gel impregnated paper (Gelman Science Inc., Ann Arbor, Mich.). The paper strips were developed using two different mobile phases. Mobile phase I was 10 mM EDTA and II was 9% NaCl/10 mM NaOH. The $R_f$ of the radiolabeled SWNT construct was 0 and both any unchelated $^{86}$Y species or unattached metal chelates were characterized by $R_f$ of 1.0 in mobile phase I. In mobile phase II, the radiolabeled SWNT construct and any free metal species were characterized by $R_f$ of 0 and the $R_f$ of any unattached metal chelate species was 1.0. The strips were spotted, developed, dried and counted intact using an Ambis 4000 gas ionization detection system (Ambis Inc., San Diego, Calif.).

Characterization of the SWNT construct was performed by reverse phase HPLC, using a Beckman Coulter System Gold Bioessential 125/168 diode array detection instrument equipped with an in-line IN/US detector for measure of radioactivity. A reverse phase C18 column was used to chromatograph these molecules.

The final $^{86}$Y-SWNT product (7) was 90% radiochemically pure and had a specific activity of 15 Ci/g, a SWNT construct concentration of 0.06 g/L, and a 86Y activity concentration of 0.90 Ci/L. Reverse phase HPLC analysis identified a sharp UV peak at 12.7 min that was attributed to the $^{86}$Y-SWNT product. This peak assignment was confirmed by the SWNT spectral signature (diode array detection) and the corresponding radioactivity trace which exhibited a sharp peak at 13.0 min. that contained 90% of the activity. There was a delay of 0.3 min that corresponded to the time to transit from the diode array detector to the downstream radiodetector. The control construct was a mixture of $^{86}$Y*DOTA+SWNT-amine product that was 95% radiochemically pure and had a specific activity of 1.4 Ci/g, a DOTA concentration of 0.12 g/L, a SWNT-amine concentration of 0.07 g/L and an activity concentration of 0.18 Ci/L.

SWNT-$^{111}$In*DOTA Constructs

The analogous nontargeting, radiolabeled construct SWNT-$^{111}$In*DOTA construct 8 was prepared by adding 111-185 MBq of acidic $^{111}$In chloride (Perkin Elmer) to 0.150 mg of SWNT-DOTA (10 g/L) in MFW and 0.050 mL of 3 M ammonium acetate (Aldrich) to yield a pH 5.5 solution. The reaction mixture was heated to 60 C for 30 min and then purified using a 10DG column with 1% human serum albumin (HSA; Swiss Red Cross) in 0.9% NaCl (Abbott Laboratories) as the mobile phase. Radioactivity was assayed in a Squibb CRC-17 Radioisotope Calibrator or equivalent (E.R. Squibb and Sons, Inc.). A small aliquot of SWNT-$^{111}$In*DOTA was used to determine the radiochemical purity by instant thin-layer chromatography silica gel (ITLC-SG) using silica gel-impregnated paper (Gelman Science Inc.) developed using 2 different mobile phases. Mobile phase I was 10 Mm EDTA and mobile phase II was 9% NaCl/10 mM NaOH. The strips were counted using an Ambis 4000 gas-ionization detection system (Ambis Inc.). Combined spectroscopic, radiographic, and chromatographic characterization of SWNT-$^{111}$In*DOTA was performed by C18 reversephase HPLC, using a Beckman Coulter System Gold Bioessential 125/168 diode-array detection instrument equipped with an in-line γ-RAM model 3 radioactivity detector (IN/US). There was a delay of 0.3 min. that corresponded to the time to transit from the diode array detector to the downstream radionuclide detector.

SWNT-$^{111}$In*DOTA had radiochemical purity of 90% as determined by ITLC-SG. The Rf of the radiolabeled SWNT construct was 0, and any unchelated $^{111}$In species and unattached metal chelates were characterized by an Rf of 1 in mobile phase I. In mobile phase II, SWNT-$^{111}$In*DOTA and unchelated $^{111}$In were characterized by an Rf of 0; the Rf of any unattached chelated metal species was 1. The specific activities of the constructs ranged from 18.5 to 1,110 GBq/g. HPLC analysis of SWNT-$^{111}$In*DOTA identified a sharp absorbance peak that was attributed to the construct 8 based on the characteristic SWNT spectral signature and a corresponding radioactivity trace. The corresponding radioactivity trace revealed a sharp peak at 13.0 minutes that contained 90% of the eluted radioactivity activity and after correction for the delay between detectors, was assigned to the $^{111}$In-SWNT product.

Example 4

Derivatizing Functionalized SWNTs with Trace Labels and Markers

Trace Labels and Markers

The SWNTs are prepared with maleimide exactly as described in Example 2. Next, unreacted maleimide groups on the SWNTs are reacted with a known amount of $^{35}$S-labeled cysteine. Free unbound cysteine is removed by size exclusion chromatography. FITC or other fluorescent markers can be purchased from several vendors for attachment to free amino groups on the SWNT prepared as described in Example 1.

Combination of Biologically Active and Tracer-Labeled Ligands

Complex molecules with multiple types of ligands can be constructed by labeling of SWNT simultaneously with antibodies and radiometal chelates and oligos by mixing 2 or more ligands at varying molar ratios to create different stoichiometry of final products. Other strategies may also be used such as 1) use of alternate initial biofunctionalized capture arms; for example, terminal amino groups and maleimide groups, to which different ligands (carrying thiocyanate or Nhydroxysuccimide vs free thiols) can be attached at maximum yield; 2) varying the order of additions to alter stoichiometry and 3) combinations of the strategies.

For small entities like DOTA and some of the fluorescent markers the moieties may be used directly as end groups on the PEG aldehydes in the cycloaddition sequence. Assuming that the conjugation reactions go to completion, the number of ligands on each nanotube can be determined reasonably accurately.

Example 5

Interactions of Functionalized SWNT with Live Cells

Tissue Culture

The CD20+, human Burkitt lymphoma cell line, Daudi, the CD33+ human leukemia cell line HL60, the PSMA+, human prostate cancer cell, LnCap are obtained from the American Type Culture Collection (Manasas, Va.). The cells were cultured with RPMI 1640 containing 10 mM HEPES, 1 mM sodium piruvate, 4.5 g/L glucose and 1.5 g/L bicarbonate (Life Technologies) supplemented with 10% of Fetal bovine serum (complete media) and maintained at 37° C. and 5% $CO_2$ in a Nuare Incubator with auto flow air regulation. These cells can control for each other or many other antigen positive or negative cell lines can be used as controls.

Flow Cytometry $5 \times 10^5$ fresh live cell lines are incubated in 0.1 ml final volume with the fluorescein, or fluorescein-derivative, conjugated SWNT antibody construct or control monoclonal antibodies for 30 minutes at 4° C. and then washed twice and fixed with 0.5% paraformaldehyde before analysis. For indirect immunofluorescence, after the primary antibody incubation for 30 minutes at 4° C., 50 µl of goat anti-human fluorescein conjugate is added for 30 minutes, followed by washing and fixing. Ten thousand cells are analyzed on a flow cytometer. Positive cells and mean peak fluorescence is derived.

Real-Time Tracking of Fluorescent SWNTs in Living Cells.

Adherent fibroblasts (NIH3T3, COS-1, CHO), epithelial cells (HeLa, HEK293, MDCK, LnCap), endothelial cells (PAE), and macrophages (THP1) are seeded and are grown in appropriate media in 35 mm MatTek dishes that incorporate a glass cover slip sealed 15 mm cutout for optimal epifluorescence imaging with an inverted microscope. Where indicated, the cells are transfected prior to imaging with fluorescent subcellular compartment markers or molecular regulators of vesicular trafficking using standard techniques, e.g. SuperFect (Qiagen) or Lipofectamine (Invitrogen). Non-adherent hematopoetic cells including Jurkat, HL60, Daudi and dendritic cells also are used by placing samples in growth media on the cover slip of the same MatTek dishes. The cells are imaged alive with an inverted Zeiss Axiovert 200 microscope (63X Plan Apochromat oil emersion objective NA=1.4) associated with a 510 laser scanning confocal system equipped with Meta spectral deconvolution and a metabolic chamber complete with plate and gas heating, humidifier and $CO_2$.

Various concentrations of fluorescent SWNTs of varying length are incubated with cells either for various times before imaging for static uptake images or, once imaging has begun, for dynamic, time-lapse imaging. For time lapse imaging a Z-stack is acquired at intervals ranging from seconds to many minutes to allow visualization of both short and long-term trafficking events. The SWNTs used are derivatized with amines to allow conjugation with various Alexa Four dyes (Molecular Probes) that permit two and three color imaging with a wide variety of fluorescent compartment markers. Compartment markers are CFP or YFP fusion proteins or vital dyes as indicated in Table 1.

The role of clathrin-mediated endocytosis in the internalization of SWNTs is elucidated by blocking the process via expression of dominant negative forms of epsin (17) or Eps15 or dynamin (dynK44A) (18). To the effects of endosomal recycling on the trafficking of SWNTs are elucidated by expressing a dominant negative form of Rab11 binding protein that inhibits this process. Temperatures are 37° C. for full trafficking, 20° C. for blocking trans-Golgi to plasma membrane trafficking and 16° C. for blocking all vesicular trafficking (17).

TABLE 1

| Compartment | CFP/YFP/RFP Fusion Protein Marker | Vital Dye Marker |
|---|---|---|
| Early Endosomes | EEA1; Rab5 | Texas Red Transferrin |
| Late Endosomes | Rab11 | Texas Red Transferrin |
| Phagosomes | Tandem FYVE Domains (17) | Opsinized, Alexa Fluor conjugated latex beads |
| Caveolae | Caveolin-1 | |
| Lipid-raft derived vesicles | | Alexa Fluor conjugated Cholera Toxin B |
| Pinosomes | | Alexa Fluor conjugated high molecular weight dextran |
| Lysosomes | | LysoTracker Green/Yellow/Red |
| Peroxisome | Peroxisome targeting signal 1 | |
| Golgi | Galactosyl transferase | Bodipy ceramide C6 |
| Endoplasmic Reticulum | M1 Protein (15); calreticulin | |
| Nucleus | Tandem SV40 NLS | Green/red-fluorescent SYTO dyes |
| Mitochondria | Bcl-XL (outer membrane); Cytochrome c oxidase VIII (matrix) | MitoTracker Green/Red |
| Actin Cytoskeleton | Actin | Alexa Fluor-phalloidin (fixed cells) |
| Microtubules | Tubulin | Oregon Green 488 paclitaxel |

Quantitative Endocytosis Assays

A variety of cell types including HeLa and MDCK are incubated at 4° C. with SWNTs of varying length derivatized with [$^{111}$In] and then raised to 37° C. for 1 to 90 min. [$^{125}$I]tranferrin is used as a positive control. Control cells are held at 4° C. The cells are washed multiple times with ice-cold Hanks' balanced salt solution and once with acetate buffer (150 mM NaCl, 1 mM CaCl2, and 20 mM sodium acetate buffer [pH 4.6]) to remove SWNTs that are not internalized. The cells are lysed with SDS buffer and the lysates subjected to g counting. Gamma counting of the input amount of [$^{111}$In] SWNTs or [$^{125}$I]tranferrin is performed where the amount of internalized SWNTs is expressed as a percent of this value. The kinetics of SWNT uptake are measured and the dependence on the length of the SWNTs is determined and compaired to that of tranferrin. Using these methods, the role of clathrin-mediated endocytosis in the uptake process is elucidated with or without prior expression by transfection of dominant negative epsin (19) or dynamin (dynK44A) (20).

For endocytic recycling (20) of SWNTs MDCK cells are loaded with [$^{111}$In]-SWNTs, as described above, for the time determined to reach a plateau of internalized material. [$^{125}$I]tranferrin is used as a positive control. The loaded cells are washed with ice-cold Hanks' balanced salt solution and once with acetate buffer, as described, to remove SWNTs that are not internalized. The cells are raised to 37° C. for 1 to 60 min. At the end of each incubation the cells are washed as described, lysed and internalized SWNTs that remain quantified by g counting. Form this analysis the rate of loss of SWNTs is determined. Using this method, the role of endosomal recycling on the loss of internalized SWNTs is elucidated with and without overexpression of a dominant negative form of Rab11 binding protein (21). To determine the role of exocytosis in this process the method is performed with and without addition of N-ethylmaleimide (21).

Transcytosis

Access of SWNTs to the interstitial space and to compartments such as the CNS in vivo can be determined in large part by their ability to traverse endothelium and epithelium in a process known as transcytosis. A well-established in vitro model of transcytosis is used to determine if SWNTs have the capacity to engage this pathway. MDCK cells are grown in MEM medium with 5% FBS on Transwell filters to allow polarization and complete cell-cell adhesion of the monolayer such that the electrical resistance is high. SWNTs of varying lengths derivatized with indium-111 are placed in the upper or lower chamber and are incubated for various lengths of time at 4° C. (control) or 37° C. The SWNTs that appear in the opposite chamber are measured by g counting counting. [$^{125}$I]labeled transferrin, albumin and tyrosine-conjugated high molecular weight dextrans are used as controls.

A line of Type II MDCK cells that stably express the human polymeric immunoglobulin receptor (pIgR) that mediates transcytosis of IgA (Dr. Keith Mostov, University of California at San Francisco) is a well-described monolayer model for facilitated, IgA mediated trancytosis (22) useful to examine therapeutic delivery of SWNTs across endothelial and epithelia barriers. SWNTs that are conjugated with [$^{125}$I]IgA are used. The Type II MDCK cells are grown on filters in Transwell plates, as described, and [$^{125}$I]IgA is applied to the basolateral surface by adding it to the lower chamber. [$^{125}$I]IgA that appears in the media of the upper chamber is measured by g counting.

Size-Dependent Internalization of SWNTs into COS-1 Cells

Figures 4A, 4B, 4C:
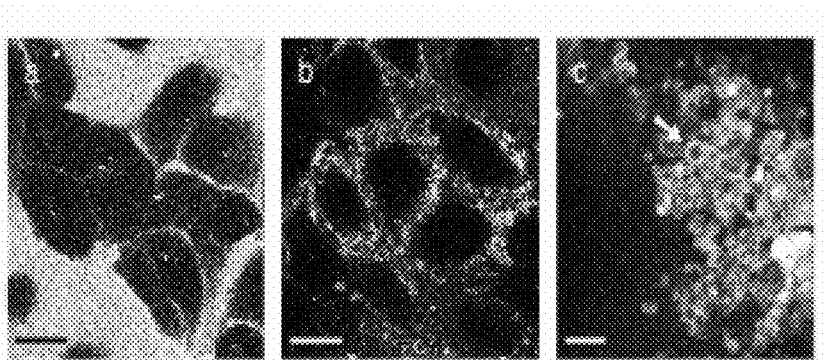
FIGS. 4A-4C demonstrate size-dependent internalization of SWNTs into COS-1 cells. COS-1 cells were incubated for 30 min at 37° C. with either long (1000-2000 nm) FITC-conjugated SWNTs (FIG. 4A) or short (50-200 nm) FITC-conjugated SWNTs (FIGS. 4B-4C) and then imaged alive with an inverted Zeiss 510 laser scanning confocal microscope. Bars represent 10 μm in FIGS. 4A-4B and 1 μm in FIG. 4C.

COS-1 cells were incubated for 30 min at 37° C. with either long (1000-2000 nm) FITC-conjugated SWNTs (FIG. 4A) or short (50-200 nm) FITC-conjugated SWNTs (FIGS. 4B-4C) and then imaged alive with an inverted Zeiss 510 laser scanning confocal microscope. Long SWNTs were not taken up by the cells such that they appear negatively imaged in a "sea" of fluorescence (FIG. 4A). In contrast, the media was cleared of the short SWNTs that were taken up by the COS-1 cells into vesicular structures consistent with endosomes (FIGS. 4B-4C). Interestingly, the fluorescent short SWNTs tended to decorate the limiting membranes of the endosomes revealing a lumen (arrow).

Specific and nonspecific ligand function, e.g., antibodies, on internalization and trafficking also is measured on individual constructs, as described, then simultaneously using constructs tagged with fluorescent tracers that are distinguishable, such as identified in Table 1. Specific and control constructs are evaluated on specific and control target cells.

Effects of SWNTs on Cell Growth and Proliferation

Commercially available cell lines are used to study toxicity of SWNT. Suspension (Daudi and HL-60), and adherent (WI-38 and Hek293) cell lines are grown in RPMI and EMEM media, respectively, supplemented with non-essential aminoacids, L-glutamine, 10% fetal bovine serum, and penicillin/streptomycin. Cells are maintained at 37° C. and 5% $CO_2$. All cells are grown to confluence ($1 \times 10^6$ cell/mL), and split to $1 \times 10^5$ cell/mL for treatment. $1 \times 10^4$ cells were aliquoted into round or flat bottom 96 well plates, depending on whether the cell line was a suspension or an adherent cell line, respectively. Wells are treated in triplicate with serial dilutions of SWNT spanning a broad final concentration range (200, 40, 8, 1.6, 0.3, and 0.06 µg/mL) or with sterile distilled water as control. Lyophilized SWNTs are reconstituted in sterile distilled water and heated at 100° C. for 5 min. A dilution series and diluted 50 fold with the appropriate cell growth media. An individual 96 well plate is prepared for each time point (2, 4, and 6 days for example in initial studies).

Figure 5:
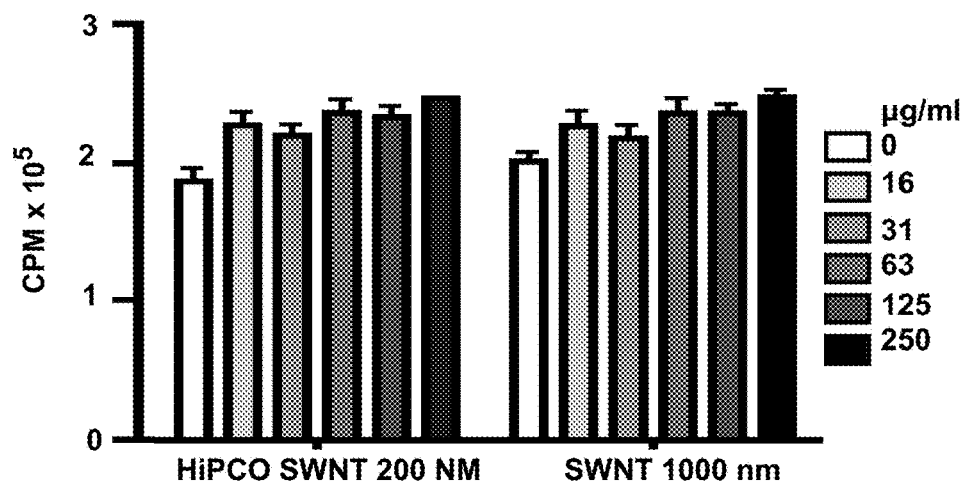
FIG. 5 depicts Daudi cell proliferation on day 6 post incubation with various concentrations of $NH_2$ functionalized 200 nm and 1000 nm SWNTs.

For the MTT assay cells were spun at 1000 g for 5 min, followed by removal of the supernatant and addition of 25 µL of a 2 mg/mL MTT solution. After incubation at 37° C. for 4 h, 150 µL of 0.04 N HCl in 2-propanol were added, and the absorbance of the dissolved crystals measured at 570 nm. The Trypan Blue exclusion assay was performed by mixing equal volumes of Trypan Blue solution and cell suspension, followed by determining live and dead cells on a hemocytometer. Cell proliferation is assessed by $^3$H-thymidine incorporation assay. 1 µCi of $^3$H-thymidine in cell culture media was added to each well. After incubation at 37° C. for 5 h, cells were stored at −80° C. Later, cells were thawed for harvest on a Skatron cell harvester and scintillation is measured in a Top Counter microplate scintillation and chemiluminescent counter. FIG. 5 illustrates that up to 250 ug/ml of SWNT (200 or 1000 nm length) do not effect the cell proliferation of Daudi cells (CD19+, human Burkitt lymphoma cell line).

Effects of SWNTs on Protein Expression

SWNT effects on protein expression in live cells is assessed broadly by use of expression microarrays (23). The effects of amine-modified soluble SWNT against fresh lymphocytes and normal fibroblasts at 4 hours (early events) and 24 hours (later events) are examined. Samples can be used fresh or snap-frozen and stored at −80° C. RNA is extracted from frozen cells by homogenization in RNAeasy, (Qiagen, Valencia, Calif.) Methods are exactly as described in the kits. Gene expression analysis is carried out using Affymetrix human gene arrays for individual gene/EST clusters using instruments and protocols recommended by the manufacturer. The average difference, i.e., the primary measure of expression level, and absolute call, as a secondary measure, are extracted for each gene as determined by default settings of Affymetrix Microarray Suite 4.0.

For oligonucleotide arrays, scanned image files are visually inspected for artifacts and analyzed using Microarray Suite v4.0 (Affymetrix). Differential expression is evaluated using several measures. Final ranking to obtain genes uniformly and strongly differentially expressed is determined by first filtering to include only those probe sets detecting genes with mean expression values that differed by at least 3-fold between the two groups (absolute base-ten logarithm of the ratio of the means>=0.4771). Probes are then ranked based on the relative magnitude of the difference (t test) between the means of the two sample sets.

Electronic Properties of Functionalized SWNT

Each functionalized SWNT is examined by atomic force microscopy and transmission electron microscopy to determine the purity, density and spacing of various pendent functionalities. Various electronic properties of functionalized SWNTs are characterized using semiconductor parameter analyzers. Such properties include the relationship between the number of pendant groups and the change in conductance and the optimum degree of sidewall modification necessary to retain the electronic properties while maintaining aqueous solubility. It is contemplated that chelated metals, such as indium and actinium atoms, known to promote charge transfer, are useful as radiotracers and radiotherapeutics, respectively. In addition, because of their potential application as MRI contrast agents the electronic properties of Gadolinium-SWNT constructs also are tested. In addition, it is contemplated that the stability of the electronic properties of SWNTs in vivo after exposure to plasma and other proteins in vivo is tested. SWNT that have been injected into mice are purified from sera and re-examined for retention of their characteristics Functionalized SWNTs (<0.5 mg/mL) are spincoated or dropcasted on prepatterned on electrodes, i.e., source drain and gate. Then AFM imaging identifys correctly aligned SWNTs, i.e. SWNTs straddling the source and drain. Subsequent electrical measurements are performed in FET geometry by measuring the electrical conductance vs. the gate voltage. Additionally, in situ changes to the conductance are measured upon conjugation of antibodies, oligonucleotides and or chelating metals.

Example 6

SWNT Interactions in Mammalian Models
Immunogenicity of Amine Functionalized SWNT In Vivo Ten doses of 0.1 mg of amine functionalized SWNTs (200 nm length in PBS) were injected into the peritoneal cavity of Balb/c mice over the course of 10 months. Serum titers to SWNT were tested by ELISA 14 days after each injection using biotinylated SWNT bound to strepavidin-coated microtiter plates. Controls were performed to account for any background signal from antibodies specific to bovine serum albumin, strepavidin or biotin.

Figure 6:
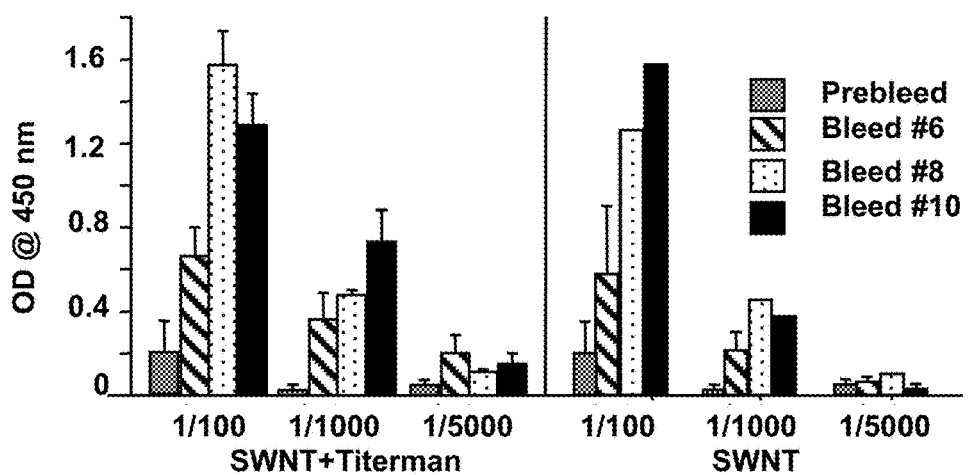
FIG. 6 demonstrates minimal serum titers to SWNTs over time for various lengths of SWNT.

After 10 injections, there was minimal antibody titer (1/100) to the SWNT (FIG. 6). Mice that had received similar i.p. injections with SWNT emulsified in adjuvant (titermax) generated slightly higher antibody titers (1:500 max). These antibodies were specific to SWNT since competition studies revealed that high concentrations (>0.1 mg/ml) of amine functionalized SWNT could inhibit 50-80% of serum antibodies, whereas biotin and free did not (data not shown).

While this finding may appear to be in contrast to earlier reports claiming that SWNT have no intrinsic immunogenicity (24), the assays described herein are far more sensitive and, therefore, can detect low levels of antibodies. It is not surprising that Abs to the SWNT are produced. In fact, a mAbs directed against the side wall of a fullerene, can interact with SWNT (25). This is advantageous since it is contemplated that the SWNT backbone may be able to induce a slight humoral immune response that can aid in the establishment of a stronger cellular immune response, while not overwhelming the host immune system.

Clearance of SWNTs

Aqueous solutions of derivatized SWNTs are injected intravenously into 4-6 weeks old BALB/c mice at a dose of 3.5 g/kg of body weight. The mice are anesthetized and then injected in the retro-orbital venous plexus with 5 µCi of the ($^{111}$In) SWNT construct. The injected volume is ~100 µL containing ~2-10 µg of SWNTs. Mice are housed in filter-top cages and provided with sterile food, water and bedding. Animal protocols are approved by the Animal Care and Use Committee at Memorial Sloan-Kettering Cancer Center. The samples are rinsed in saline, blotted dry, weighed and then counted using a gamma counter (Cobra II, Packard Instruments, Meriden, Conn.). The energy windows used are 15-550 keV for $^{111}$In which encompasses the chief peaks. Samples of the injectates are used as decay correction standards. Data is expressed as % ID/g.

Organ Histology after Injection of SWNTs

Female BALB/c 3-4 weeks of age, are obtained from Taconic, Germantown, N.Y. The mice are anesthetized and then injected intravenously (in retro-orbital venous plexus) with SWNT. Mice are euthanized by carbon dioxide asphyxiation at 2 hours, 2, 7, 14, 21 days post-injection with SWNT (3-5 mice per time-point) and chemistry in the blood including blood urea nitrogen (BUN) and serum creatinine is estimated. Tissues are fixed in 10% neutral buffered formalin, processed by routine methods and embedded in paraffin. Sections (2-3 μm) are stained with hematoxylin and eosin (H&E), Periodic acid Schiff (PAS) and Masson's trichrome, and evaluated with an Olympus BX45 light microscope. Age-matched normal BALB/c mice serve as controls for the comparison of gross and microscopic features at each time-point.

Immunohistochemistry and Electron Microscopy

Paraffin embedded tissue sections (2-3 μm) are immunostained with monoclonal antibodies to T cells, B cells, macrophages or neutrophils to examine inflammatory infiltrates if present, using methods described previously (19, 26). Pieces of tissue are fixed in 4% paraformaldehyde, post-fixed in 1% osmium tetroxide and later embedded in epon. Ultra-thin sections (200-400 μm) are cut on nickel grids, stained with uranyl acetate and lead citrate and examined using an electron microscope (Hitachi H-7500, Pleasanton, Calif.).

Evaluation of Renal Pathological Damage

Kidneys appear to be a key target organ. The glomeruli are assessed for decrease in size and cellularity. The percentage of glomeruli showing shrinkage (50% of control size) was evaluated by counting the total number of glomeruli in mid-coronal sections of the kidneys (3-4 per mouse). The number of juxtaglomerular cells per glomerular hilus and the extent of glomerular involvement (% of glomeruli involved) is calculated. The arterial and arteriolar medial (smooth muscle) cell vacuolization is semiquantitatively estimated, based on the percentage of cells involved per vessel cross section (<25%=+/−; 25-50%=1+; 50-75%= 2+; >75%=3+). The extent of tubular cell vacuolization, tubulolysis, loss of brush border and tubular atrophy is expressed as the mean percentage of total number of tubules in the kidney sections.

The extent of basement membrane thickening in the lysed tubules is examined in Trichrome stained sections.

Example 7

PET/CT Imaging Using SWNT-$^{86}$Y*DOTA

Imagers and Data Analysis

CT imaging was performed using the CT component of the XSPECT (Gamma Medica, Northridge, Calif.) a dedicated smallanimal SPECT-CT scanner for non-invasive, ultra-high-resolution imaging in vivo of single-photon-emitting radiotracers and ultrahigh-resolution CT scans for anatomic registration. The imaging times for the CT studies were 10 min. with a resolution of <0.100 mm. These CT imaging studies require animals to be fully anesthetized using isofluorane anesthesia.

The microPET Focus™ 120 (CTI Molecular Imaging, Inc., Knoxville, Tenn.) is a dedicated small-animal scanner for imaging PET radiotracers. An energy window of 350-750 keV, a coincidence timing window of 6 nsec, and an acquisition time of 10-20 min were used. The resulting list-mode data were sorted into 2D histograms by Fourier re-binning and transverse images reconstructed by filtered back-projection into a 128×128×95 matrix. The reconstructed spatial resolution is 2.6 mm full-width half maximum (FWHM) at the center of the field of view. The image data were corrected for non-uniformity of response of the microPET™, i.e. were normalized, deadtime count losses, physical decay to the time of injection, and the 86Y positron branching ratio but no attenuation, scatter, or partial-volume averaging correction was applied. An empirically determined system calibration factor, i.e. mCi/mL/cps/voxel, for mice was derived by imaging a mouse-size cylinder containing $^{18}$F uniformly dispersed in water and used to convert voxel count rates to activity concentrations. The resulting image data were then normalized to the administered activity to determine by region-of-interest analysis the percent of the injected dose per gram (% ID/g) of tissue corrected for radioactive decay to the time of injection.

AsiPRO VM 5.0 software (Concorde Microsystems, Knoxville, Tenn.) was used to perform image and region of interest (ROI) analyses with the PET and CT datasets. For the ROI analyses, a minimum of 3 regions per tissue per animal were collected and the average % ID/g and standard deviation determined. The average % ID/g tissue per animal was used to determine an average % ID/g per tissue per group and the standard deviation within the group values was calculated. Standards of each injected formulation were counted to quantify the % ID/g. Unpaired two tailed t-tests were performed to assess temporal differences of tissue activity. Prism software (Graphpad Software, Inc., San Diego, Calif.) was used for statistical analyses and plotting data. TEM image analysis was performed using ImageJ software available online from the National Institutes of Health. AFM image analysis was carried-out using Nanoscope II software from Digital Instruments.

Murine Model

Ten male athymic nude mice (Taconic, Germantown, N.Y.), 10-12 weeks old, were separated into three groups. Group I (n=4) received an intravenous (i.v.) injection of 6.7 MBq (0.18 mCi) and 0.012 mg 4 in 0.20 mL via the retroorbital sinus. Group II (n=3) received an intraperitoneal (i.p.) injection of 6.7 MBq and 0.012 mg 4 in 0.20 mL. Group III (n=3) received an intravenous (i.v.) injection of 13.3 MBq (0.36 mCi) $^{86}$Y-DOTA+0.015 mg of 2 in 0.20 mL via the retroorbital sinus. All animals were imaged by PET on day 1 at 3 hours post-injection; Group I and II animals were imaged by CT at this time as well, while still under anesthesia. On day 2, 24 hours post-injection, Group I and II animals were imaged by PET.

Animals were sacrificed at 24 h post-injection and the kidneys, liver and spleens were harvested according to approved IACUC institutional protocols. Tissue samples were weighed and counted in a Packard Cobra c-counter (Packard Instrument Co., Inc., Meriden, Conn.) using a 315-435 KeV window. Standards of each injected formulation were counted to determine the % ID/g.

Biodistribution of SWNT-$^{86}$Yttrium*DOTA Constructs in Whole Body Images

Figure 7A:
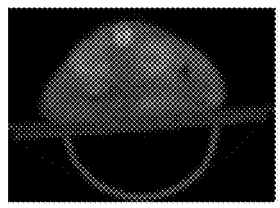
FIGS. 7A-7F are fused PET and CT images at 3 hours post-injection of SWNT-$^{86}$Y*DOTA, showing a transverse (z-direction, FIGS. 7A, 7D), a coronal (γ-direction, FIGS. 7B, 7E), and a sagittal (x-direction, FIGS. 7C, 7F) slice of one representative animal from group I (i.v., FIGS. 7A-7C) and one from group II (i.p., FIGS. 7D-7F).
Figure 7B:
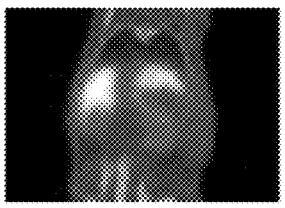
Figure 7C:
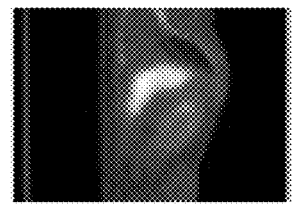
Figure 7D:
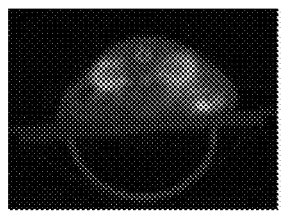
Figure 7E:
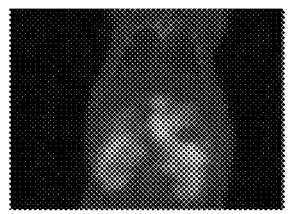
Figure 7F:
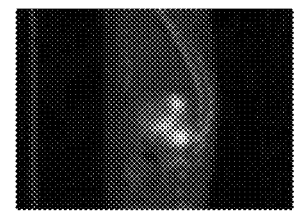

The ten mice were separated into three groups, each mouse in groups I and II received 0.012 mg of 4 labeled with 6.7 MBq of $^{86}$Y, administered i.v. or i.p., respectively. Animals in group III (control group) each received a physical mixture of 13.3 MBq of $^{86}$Y-DOTA and 0.015 mg of 2 via i.v. injection. The biodistribution of SWNT-$^{86}$Yttrium*DOTA in vivo by serial PET was evaluated and anatomic imaging using a dedicated small-animal CT scanner was performed. Software fusion of the resulting PET and CT images was carried out to combine the images. The imaging results were confirmed by sacrificing the animals and harvesting, weighing, and counting the activity in the organs. PET images of animals in groups I and II at 3 hours postinjection clearly demonstrated accumulation of activity in the kidneys, spleen and liver (FIGS. 7A-7B). The kidney images showed uptake primarily in the renal cortex, while the renal medulla was devoid of activity. There was no blood-pool activity observed in these images. In Group I, the SWNT-$^{86}$Yttrium*DOTA construct appeared to avidly localize in the spleen and liver. In group II, spleen and liver uptake was significantly lower and a diffuse activity was evident from the i.p. cavity suggesting a relatively slow egress from the i.p. compartment into the vascular compartment. After 24 hours there was no significant difference in the accumulated activity in the spleen and liver within each group compared to the 3 hour timepoint.

Additionally, the kidneys of the animals in groups I and II had begun to clear the constructs. These data indicate that the clearance from the spleen and liver is slower than from the kidneys. The radioactivity in the liver of the group I animals was still significantly higher than the group II animals at both timepoints evaluated. As expected for a stably chelated metal-ion species with a relatively small molecular weight, the control mixture cleared completely from group III within 3 hours. The imaged radioactivity was located primarily in the bladder (~1% ID/g at 3 hours) and was consistent with urinary excretion of small molecules (data not included).

Percent Injected Dose Per Gram of SWNT-$^{86}$Yttrium-DOTA Constructs

Figure 8A:
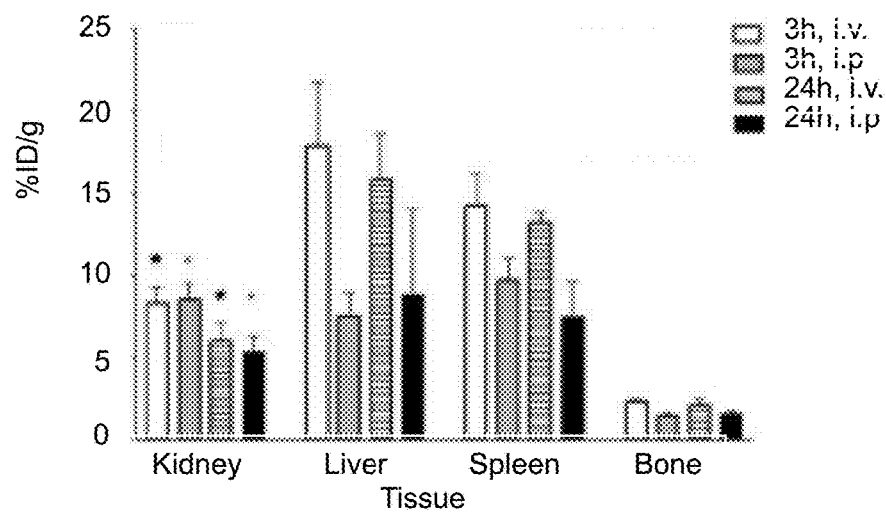
FIGS. 8A-8B show biodistribution data obtained from the PET imaging experiment and from tissue harvest.

Region of Interest (ROI) analysis of the PET images in each of the group I and II animals was performed to extract a decay corrected activity concentration in various organs. Data (FIG. 8A) are reported as the mean±standard deviation % ID/g. The kidneys had 8.30±0.92 and 8.50±1.05; the liver had 17.8±3.95 and 7.54±1.38; the spleen had 14.3±2.0 and 9.7±1.3; and the bone (femur and spine) had 2.26±0.14 and 1.44±0.23% ID/g at 3 hours post-injection in the group I and II animals, respectively.

At 24 hours post-injection, the kidneys had 5.96±1.23 and 5.42±0.85; the liver had 15.8±2.90 and 8.83±5.17; the spleen had 13.2±0.60 and 7.51±2.12; and the bone had 2.02±0.36 and 1.5±60.17% ID/g in the group I and II animals, respectively. The accumulated activity in the kidneys cleared significantly in Group I (P=0.023) and Group II (P=0.017) over this 21-hour period. However, statistical analysis showed that the activity accumulated in the spleen, liver and bone was not clearing over this period of time.

Residual SWNT-$^{86}$Yttrium*DOTA activity that was slowly exiting the i.p. compartment yielded poorer image contrast in the group II mice. Interestingly, the construct activity that did exit the i.p. cavity had the same kidney uptake as the i.v. administered construct at both timepoints, but very different liver and spleen accumulation. The % ID/g activity in the livers of group II animals is 42% of that in the group I animals at 3 hours post-injection, and 56% of that in the group I animals at 24 hours post-injection. It appeared that the equilibration process is slow and the liver activity increases with time in the Group II animals.

Figure 8B:
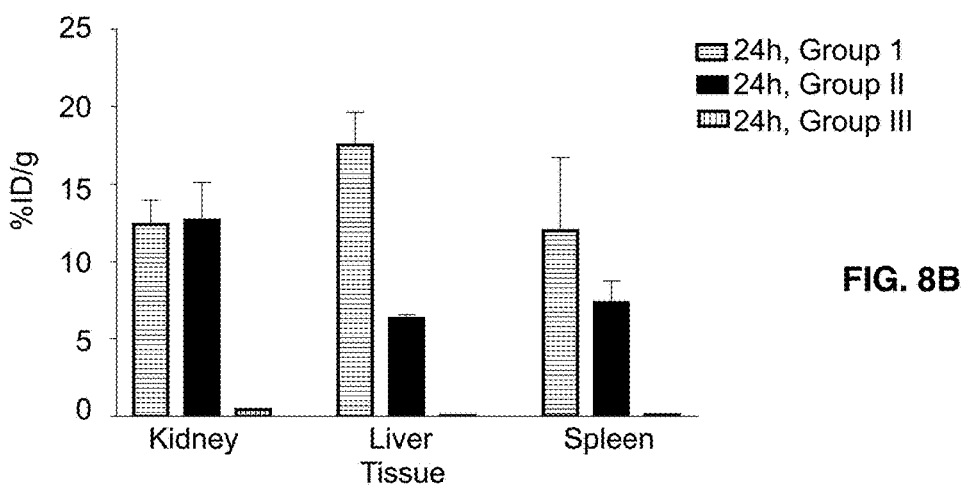

Biodistribution data (FIG. 8B) obtained from tissue harvest at 24 hours was in good agreement with the ROI data. The spleen showed the same differential accumulation as the liver as a function of i.p. versus i.v. administration. Group III control animals showed no organ-specific uptake of $^{86}$Y with only small amounts of activity (0.1 to 1% ID/g) in the kidney, liver and spleen. The post-mortem biodistribution data and the 3-hour PET images showed this control mixture rapidly cleared from the Group III mice.

The whole-body PET images indicated that the major sites of accumulation of activity resulting from the administration of SWNT-$^{86}$Yttrium*DOTA were the kidney, liver, spleen, and, to a much less extent the bone. The % ID/organ values for kidney, liver, and spleen, 24 hours post-i.v. injection, were 5.96±1.20, 15.2±1.54, and 0.82±0.04, respectively. The corresponding % ID/organ values for kidney, liver, and spleen, 24 hours post-i.p. injection, were 5.48±0.61, 4.46±1.08, and 0.60±0.09, respectively. Whole-body activity was decreasing over this 24 hour period of time, as only about 20% of the total i.v. administered activity in the Group I animals and about 11% of the total activity in the Group II animals could be accounted for. In another biodistribution experiment, SWNT-$^{111}$In*DOTA was injected into mice and ITLC analysis of urine samples obtained 1 hour after injection was consistent with SWNT-$^{111}$In*DOTA being excreted.

Figure 9:
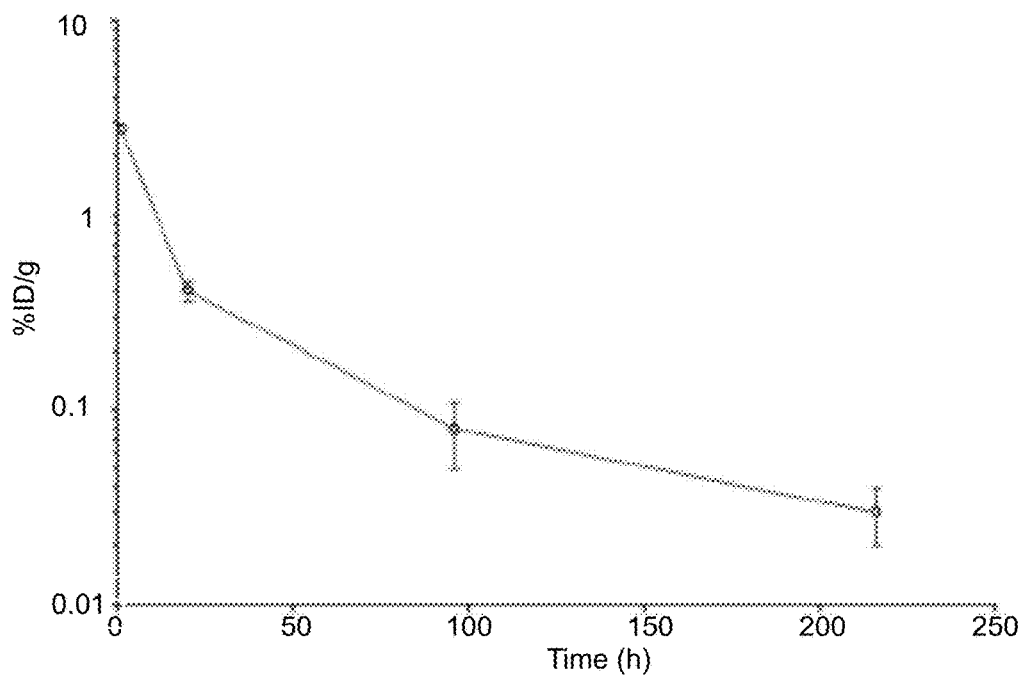
FIG. 9 is a plot of the blood clearance of SWNT-$^{111}$In*DOTA following i.v. injection (n=3 per group).

The clearance of radiometal-labeled SWNT constructs from the blood compartment is rapid. This was observed in this study (no blood pool activity at 3 h) and quantitatively measured using the longer half-lived SWNT-$^{111}$In*DOTA (Example 3). Briefly, SWNT-$^{111}$In*DOTA was injected into mice using the retroorbital sinus route and venous blood samples were obtained 1, 20, 96, 216, and 360 hours after injection from groups of three animals per timepoint (Example 11). The data are shown in FIG. 9. After 1 hour 2.76±0.14% ID/g was still in the blood and after 20 h only 0.41±0.05% ID/g was in circulation. The experiment was continued for 15 d at which time no activity was found in circulation. Example 11 presents biodistribution data of SWNT-rituxumab-$^{111}$In*DOTA in a study of lymphoma tumor targeting. Tissue harvest indicated that the major sites of $^{111}$In accumulation were the kidney, liver, spleen, and to a much less extent the bone, similarly to the $^{86}$Y accumulation. $^{111}$In cleared the kidneys more rapidly than the spleen and liver.

The mass amounts of SWNT construct that were used per animal herein also would be in the same range as the mass amounts used in therapeutic efficacy or diagnostic studies with targeting SWNT constructs. The amount of activity accumulating in the organs of these animals does not pose a problem in translating these constructs to other studies. It has been noted that the covalent attachment of targeting protein moieties to SWNT alters biodistribution. Thus, appropriately designed targeting diagnostic agents based on a SWNT platform, might further alter liver, kidney and spleen accumulation/clearance. Furthermore, the rapid blood clearance of drug construct can be beneficial in the use of short half-lived radionuclides in diagnostic applications, as prolonged persistence of blood pool activity following construct administration obscures target imaging due to a low signal-to-noise ratio. Using yttrium-86 allows for extrapolation of a therapeutic dose of $^{90}$Y-labeled compounds.

Example 8

Specific Delivery of and Therapy with SWNT in Mice Transfection of Cells

The lymphoma Burkitt cell line was transfected by electroporation, with a Gene Pulser II Electroporation System at 950 uF, 250 mV (Bio-Rad Laboratories, Menville, N.Y. 1998.). For the GFP-Daudi, selective media was prepared by adding Geneticin (GIBCO BRL) to complete media and for the GFP-PSA-Daudi, by adding Hygromycin B (Invitrogen) to complete media and selecting for 12 weeks. Previously pcDNA-3-GFP was prepared by transformation of bacteria using heat shock and selection on LB Amp Agar plates. The DNA construct was confirmed by restriction digestion with Big II (New England Bio Labs). In order to monitor the growth rates of the tumors in the serum of the animals the GFP-Daudi cell line is also transfected with a pSecTag2-Hygro-PSA vector (Invitrogen, Carlsbad, Calif.), which is amplified by transformation of E. coli DH5" using heat shock and selection on N Amp agar. After electroporation to obtain PSA-GFP-Daudi cells, cells are selected and subcloned as above, and tested for secretion of PSA (27-29).

Tumor Model

All animals are obtained from Taconic Farms (Taconic, Germantown, N.Y.). Female 5-7 weeks old immunocompromised CB17 SCID strain that are capable of growing human xenografts were selected. Mice are injected with 5E6 GFP-Daudi Cells in 0.1 mL of PBS by tail vein injection. Animals are monitored 5 d/week until paralysis of the lower extremities occurred at which point they are euthanized to do imaging and preparation of tissue samples for histopathology and flow cytometric analysis. Initially animals are inoculated with tumor intravenously and observed for plasma PSA levels (day 6,13,21); whole animal imaging (day 1,6,13,21,28) (30-31); and at sacrifice (day 1,6,13,21, 28) for histopathology and flow cytometry. Plasma PSA, GFP+ and $CD19^+$ cell numbers in the femur and blood are plotted vs time. Whole animal GFP imaging is correlated with these data. Estimates of cells in various organs can be made and used for modeling.

Sacrifice of each individual animal is made at the time points of interest. Tissues are fixed in 10% formalin solution, embedded in paraffin, and sectioned on a microtome into approx. thirty 8 micron sections per tissue. One third of these sections is stained with Hematoxylin & Eosin for general histology. A second section is stained immunohistochemically with anti-B cell antibodies (CD20, CD19). Whole sections from the final third are digitized on our BX60 Olympus fluorescent microscope with GFP filter cube and motorized stage. The spatial coordinates of all fluorescent tumor cells are recorded and are used as input for Monte Carlo modeling of the microdosimetry.

To image GFP-Daudi cells injected in the CB17-SCID mice the mice are anesthetized with Ketamine and Xylazine (4.3:1) by IP injection. The mice are shaved with A-5 Single Speed Clipper (Oster, Taiwan, China). A TLS 479/40 lamp (150 W halogen light), (Light Tools Research, Encinitas, Calif.) with two light dispersing arms (cut off at 515 nm) are directed towards the animals at 45° angle to excite the GFP-Daudi cells. Images are taken with a MTIA CCD 72 camera through an Omega optics excitation filter 535AF45 (480-490 nm). Images are analyzed with MCID software (Imaging Research, St. Catharines, Ontario, Canada.) (9-10, 32).

Injected GFP-Daudi cells grow well in mice. By day 21-28 whole body imaging shows cell uptake in the vertebra and long bones. Flow cytometry has quantitated a linear increase in $CD19^+$ and $GFP^+$ cells, beginning at day 13 in femur. No cells are detectable for first 13 days above level of background and then cell numbers steadily rise to 15-20% at day 21 and 25-30% by day 28. The geometric size of the tumor nodules has been initially observed by histopathology.

Example 9

Flow Cytometry of Antibody-SWNT-SAMSA Constructs

SWNT-DOTA-Mal was preconjugated to the fluorescent probe 5-((2-(and-3)-S-(acetylmercapto)succinoyl)amino) fluorescein ([SAMSA-fluorescein]; Molecular Probes) and then modified with thiolated-antibody for flow cytometry experiments. SAMSA-fluorescein was activated and then reacted with the thiol-reactive SWNT-DOTA-Mal, purified using a 10DG column and PBS mobile phase to obtain the fluorescent conjugate SWNT-DOTA-Mal-S. This SAMSA modification of the SWNT was performed under substoichiometric conditions, relative to the number of maleimides, to leave maleimides available for attachment of antibodies. Thiolated-antibody was then reacted and purified as described to yield SWNT-rituximab-SAMSA.

Flow cytometric analysis of Daudi and HL60 cell lines was performed with SWNT-rituximab-SAMSA construct or the isotype control SWNT-HuM195-SAMSA construct. Cells were acquired on an FC500 cytometer (Beckman Coulter, Fullerton, Calif.) and analyzed with FlowJo software (Tree Star, Inc., Ashland, Oreg.) for binding of antibody-SWNTs.

Figure 10:
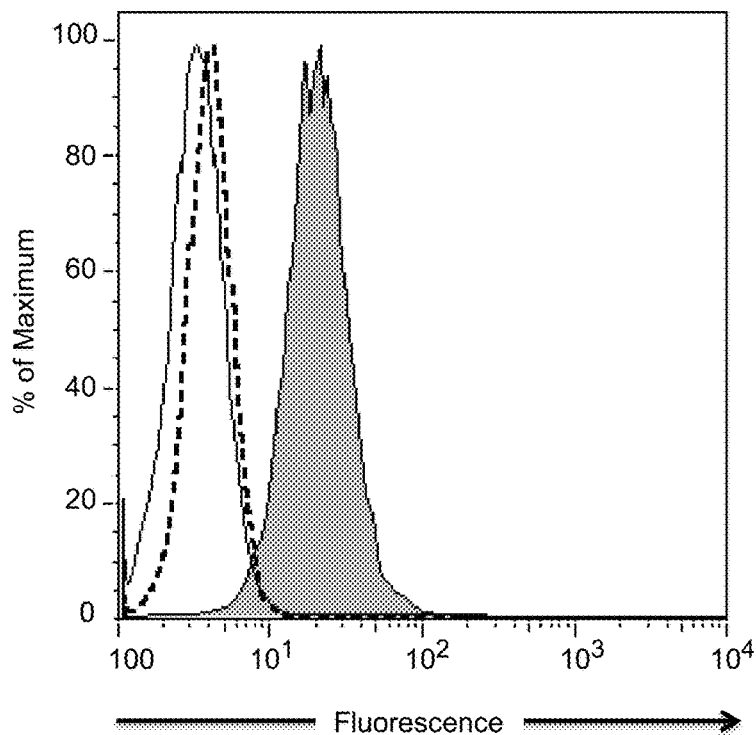
FIG. 10 depicts flow cytometric histograms demonstrating specific binding of fluorescent-labeled construct SWNT-rituximab-SAMSA to Daudi cells. Shown is overlay of single-parameter histograms of (i) Daudi cells+SWNT-rituximab-SAMSA (shaded histogram), (ii) Daudi cells+SWNT-HuM195-SAMSA (solid-line trace), and (iii) HL60 cells+SWNT-rituximab-SAMSA (dashed-line trace). Fluorescence being directly measured is due to the SAMSA chromophore that is attached to the SWNT backbone.

$1\times10^6$ Daudi human B cell lymphoma cells (CD20+, CD33−) or HL60 human promyelocytic leukemia cells (CD20+, CD33−) were incubated with 4 μg of SWNT-rituximab-SAMSA or the isotype control SWNT-HuM195-SAMSA. The SWNT-rituximab-SAMSA constructs showed specific binding to CD20+ Daudi cells, but not to CD20+ HL60 cells (FIG. 10). Similarly the SWNT-HuM105-SAMSA constructs bound specifically to CD33+ HL60 cell lines (data not shown). Because rituximab and HuM195 served as internal cross controls for each other, the results demonstrated the binding of the constructs to Daudi and HL60 was not an Fc receptor mediated event. Furthermore, the ability to directly trace label the SWNT backbone with the SAMSA, rather than the IgG, directly demonstrates that the IgG was delivering the SWNT to the cells when it binds.

Example 10

In Vivo Biodistribution and Tissue Uptake of Non-Targeted $^{111}$In-Labeled SWNTs The biodistribution of the nontargeting, radiolabeled construct prototype, SWNT-$NH_2$-$^{111}$In*DOTA was investigated in normal, nontumor-bearing mice. Female BALB/c mice, 8- to 12-wk old (Taconic Farms), were placed into 5 groups of 3 animals per group. Briefly, 0.007 mg of SWNT-$NH_2$-$^{111}$In*DOTA (specific activity, 37 GBq/g) in 0.1 mL of 1% HSA was injected intravenously per mouse via the retroorbital sinus. One group of mice was sacrificed at each of 1, 24, 96, 216, and 360 h and tissue samples, including blood, brain, lung, heart, adipose tissue, liver, kidney, spleen, and femur were harvested, weighed, and counted using a Cobra g-counter (Packard Instrument Co., Inc.) with a 315- to 435-keV window. Standards of the injected formulation were counted to determine the percentage injected dose per gram (% ID/g). The control for this study was a mixture of $^{111}$In-DOTA and SWNT-$NH_2$. This mixture was prepared by adding 37 MBq of acidic 111In chloride to 0.5 mg (10 g/L in MFW) of 1,4,7,10-tetraazacyclododecane-1, 4,7,10-tetraacetic acid (DOTA; Macrocyclics, Inc.) and 0.050 mL of 3 M ammonium acetate to yield a pH 5.5 solution. The reaction mixture was heated to 60 C for 30 min and then purified as described; 0.150 mg of SWNT-$NH_2$ in MFW was added to the $^{111}$In-DOTA product and mixed.

Figure 11A:
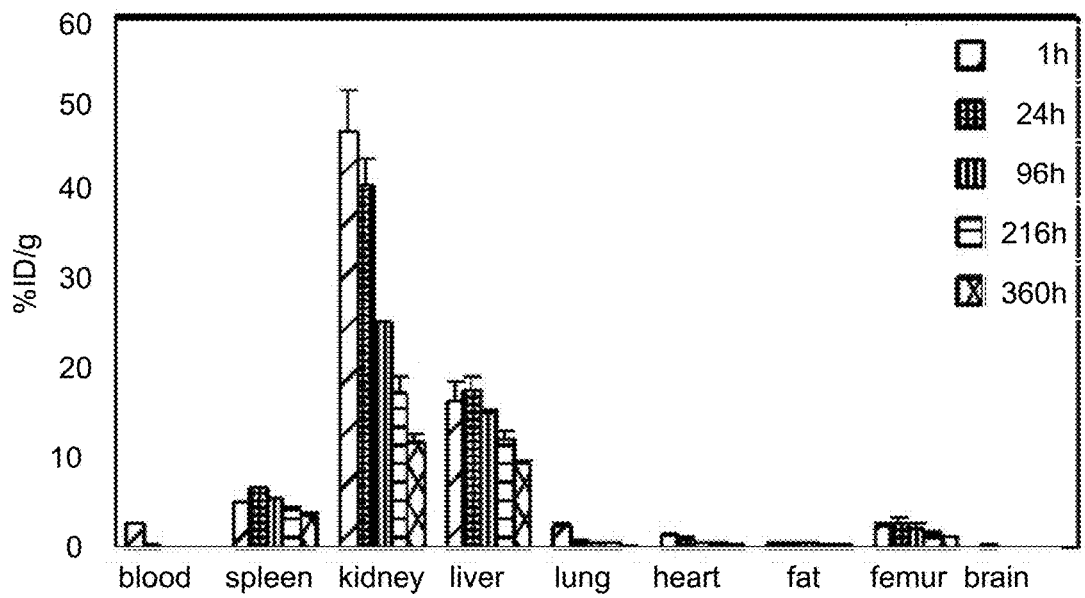
FIGS. 11A-11B depict biodistribution data (% ID/g values [mean±SD]) after administration of SWNT-$^{111}$In*DOTA in nontumor-bearing mice (FIG. 11A) and clearance of radioactivity from kidney, liver, and spleen as a function of time after administration of SWNT-$^{111}$In*DOTA (FIG. 11B).
Figure 11B:
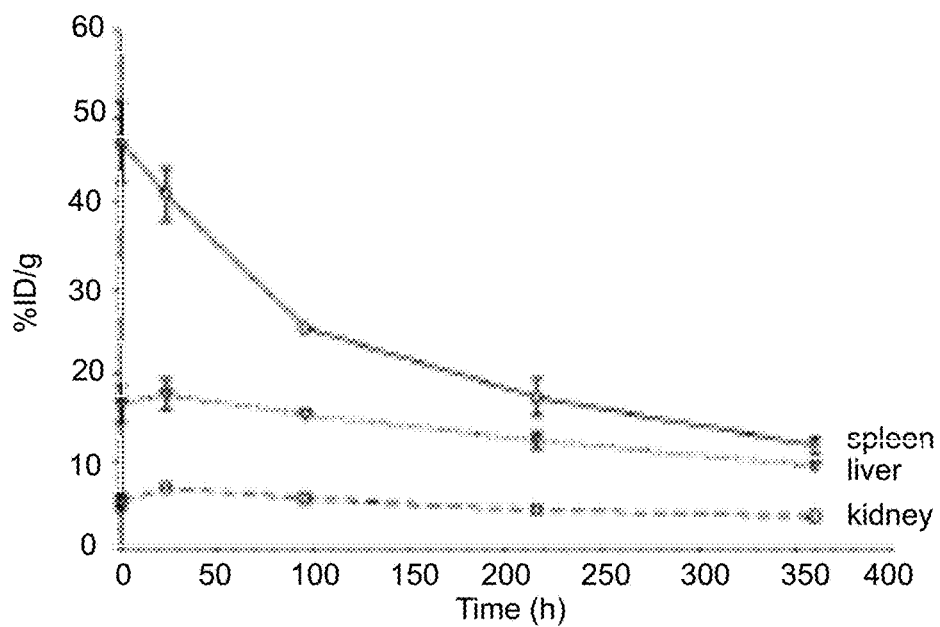

Clearance of the nontargeting, radiolabeled construct SWNT-$NH_2$-$^{111}$In*DOTA from the blood compartment was rapid. After 1 h, 2.76±0.14% ID/g was still in the blood and, after 20 h, only 0.41±0.05% ID/g was in circulation. The experiment was continued for 15 d, at which time no activity was found in circulation. Tissue harvest indicated that the major sites of $^{111}$In accumulation were the kidney, liver, spleen, and, to a much lesser extent, bone (FIGS. 11A-11B). $^{111}$In cleared the kidneys more rapidly than the spleen and liver. Urine samples were collected from mice 1 h after injection. Radioactivity was noted and the samples were analyzed using the ITLC methods described. The activity remained at the origin of strips submitted to mobile phase I, indicating $^{111}$In associated with SWNT. As expected, the control mixture containing the low-molecular-weight radiolabeled DOTA and SWNT-NH$_2$ cleared completely from the mice within a few hours (data not shown). It is contemplated that the SWNTs most likely cleared via filtration through the slit-like spaces in the renal glomeruli, which have a pore diameter of about 30 nm. ITLC on urine samples obtained after 1 hour is consistent with SWNT-$^{111}$In*DOTA.

It also is contemplated that these methods are suitable for longer term toxicity studies in mice, e.g., up to 6 months. Mice are injected IV with high (200 ug) and low (10 ug) amounts of SWNT constructs (5 mice per group) or PBS control (5 mice). Mice are observed over 1, 3, and 6 months. Weights are recorded weekly. Clinical appearance is recorded twice per week. At 1, 3 and 6 months, blood chemistries, hematologic indices, and organ histology are evaluated in each group as described in this Example.

Generation of GFP-FFLuc Transfected Daudi

The green fluorescent protein (GFP) and firefly luciferase (FFLuc) gene (Clonetech Laboratories) was subcloned into the SFG retroviral vector, and vesicular stomatitis virus G glycoprotein (VSV-G) retroviral supernatants derived from gpg29 fibroblasts transduced with the resulting SFG (GFP-FFLuc) plasmid were used to transduce Daudi tumor cells (34-35). The resulting cells were sorted by flow cytometry for GFPexpression to isolate a homogeneous population of GFP1/FFLuc1 Daudi tumor cells for expansion. This modification permitted us to monitor disease progression by bioluminescence imaging (BLI) (38) and to quantitate the extent of lymphoma in the bone marrow.

In Vivo Disseminated Tumor Model

The specific SWNT-rituximab-$^{111}$In*DOTA construct or control SWNT-HuM195-$^{111}$In*DOTA (Lintuzumab) construct was prepared by adding 111-185 MBq of acidic 111In chloride to 0.50 mg of SWNT-rituximab-DOTA or SWNT-HuM195-DOTA (50 g/L) in MFW and 0.050 mL of 3 M ammonium acetate to yield a pH 5.5 solution. The reaction mixture was maintained at ambient temperature for 30 min and then purified using a 10DG column with 1% HSA/0.9% NaCl. The radiochemical purity of SWNT-rituximab-DOTA or SWNT-HuM195-DOTA was 95% and the radiolabeled Rituximab was 98% as determined by the ITLC-SG methods described herein.

The biodistribution and tumor targeting specificity of SWNT-rituximab-$^{111}$In*DOTA was evaluated against different controls in a murine model of disseminated lymphoma (33) using the GFP1/FFLuc1 Daudi cell line. The tumor was introduced by injecting 5 million cells into each of the female C.B.-17 severe combined immunodeficiency (scid) mice (8- to 10-wk old; Taconic Farms) intravenously via the retroorbital sinus route. Tumor growth in mice was determined by BLI using a Xenogen IVIS Optical Imaging System (Xenogen Corp.). Imaging was performed on mice that received an intraperitoneal injection of 3 mg of D-Luciferin (Xenogen) per mouse. On day 28 after tumor infusion, the tumor-bearing mice were separated into 4 groups; an additional 2 groups of scid mice with no tumor were included as control. Biodistribution studies were performed at 24 h after injection of the radiolabeled constructs.

Group 1 mice (n=6), with tumor, received 0.018 mg of the specific construct SWNT-rituximab-$^{111}$In*DOTA. Group 2 mice (n=6), with tumor, received 0.018 mg of the nonspecific control construct SWNT-HuM195-$^{111}$In*DOTA. Group 3 mice (n=3), with no tumor, received 0.018 mg of the specific construct SWNT-rituximab-$^{111}$In*DOTA. Group 4 mice (n=3), with no tumor, received 0.018 mg of the nonspecific control construct SWNT-HuM195-$^{111}$In*DOTA. Group 5 mice (n=4), with tumor, received 0.010 mg of the nontargeting construct SWNT-$^{111}$In*DOTA as a control for CNT. Group 6 mice (n=6), with tumor, received 0.015 mg of the [$^{111}$In]Rituximab targeting antibody as a positive control. All constructs were adjusted to a specific activity of 37 GBq/g and were administered intravenously by the retroorbital sinus route. Mice in groups 1, 2, 5, and 6 were xenografted 28 d before this biodistribution study with the GFP1/FFLuc1 Daudi tumor.

Figure 12A:
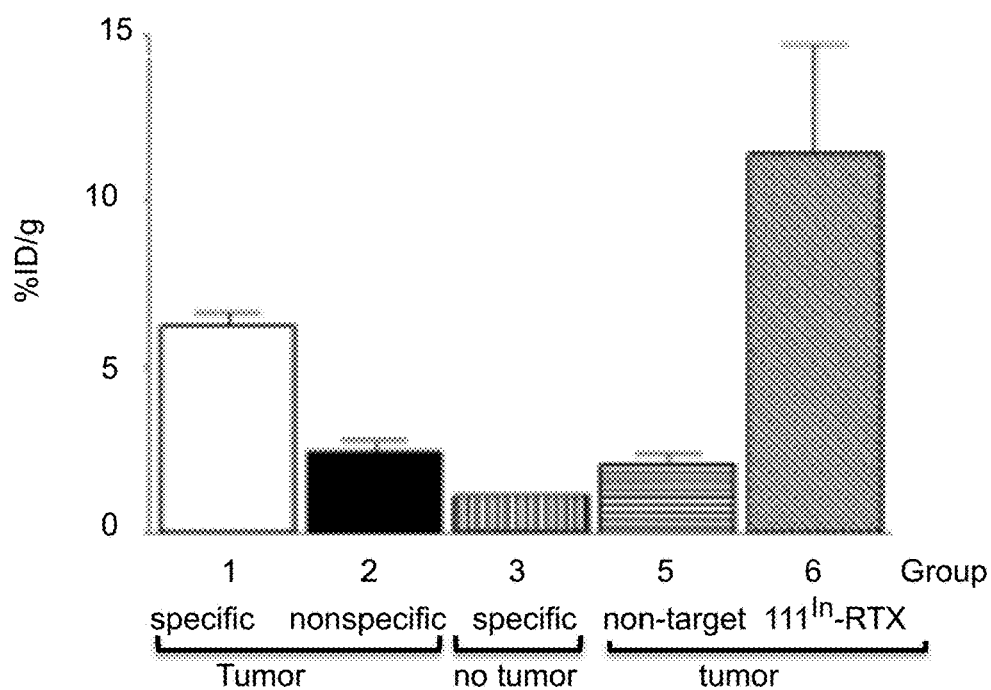
FIGS. 12A-12B depict lymphoma-infiltrated femur (FIG. 12A) and spleen (FIG. 12B) uptake data (% ID/g values [mean±SD]) of SWNT constructs and controls in scid mice with and without GFP1/FFLuc1 Daudi tumor.

In the femurs of tumor-bearing mice, the mean % ID/g values were greater for the specific SWNT-rituximab-$^{111}$In*DOTA construct (group 1) than for the nonspecific SWNT-HuM195-$^{111}$In*DOTA construct (group 2) (P<0.0001) (FIG. 12A). FIG. 5 displays the data for all groups for the tissues measured. The mean % ID/g values were 5.6-fold greater (FIG. 12A) for the group 1 mice with tumors compared with the group 3 control mice (P<0.0001). More of the specific construct SWNT-rituximab-$^{111}$In*DOTA (group 1) accumulated in the femur of mice with tumors than did nontargeting, nonantibody-appended construct SWNT-$^{111}$In*DOTA (group 5) (P<0.0001) (FIG. 12A).

Figure 12B:
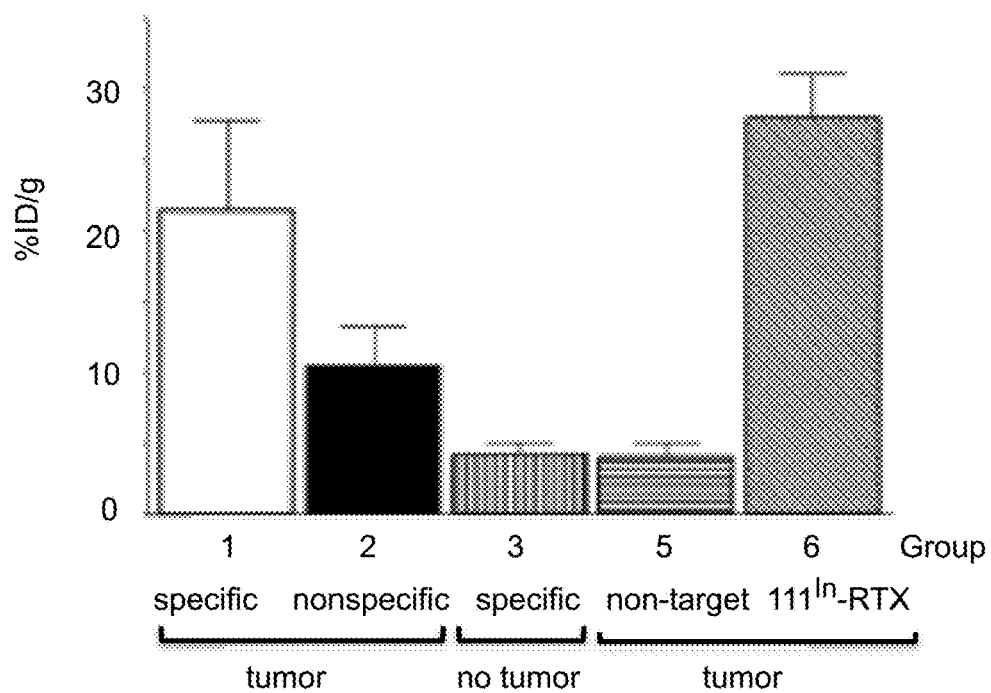
Figure 13A:
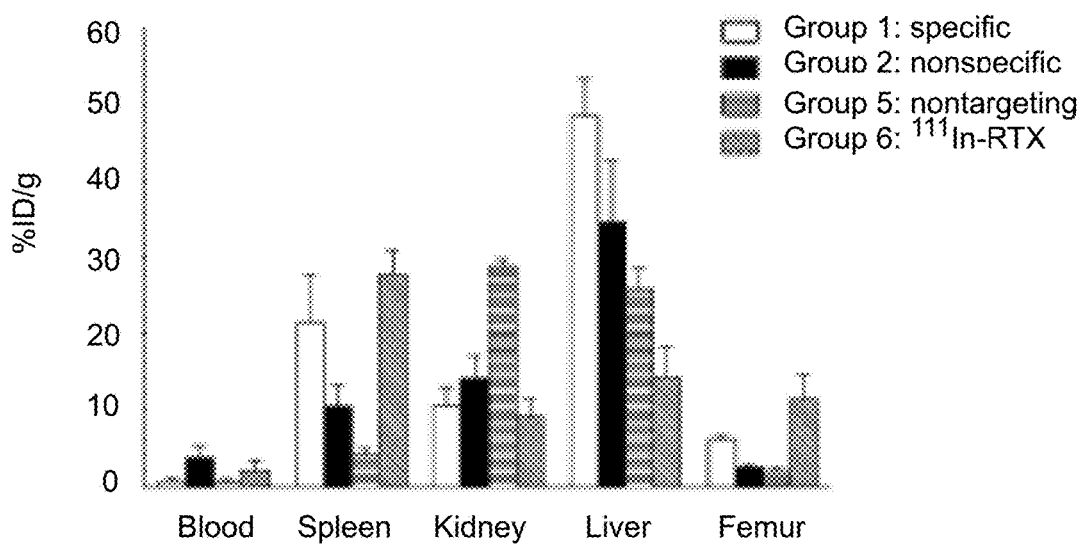
FIGS. 13A-13B depict the iodistribution data (% ID/g values [mean±SD]) of SWNT constructs and controls in scid mice with GFP1/FFLuc1 Daudi tumor (FIG. 13A) and without tumor (FIG. 13B).
Figure 13B:
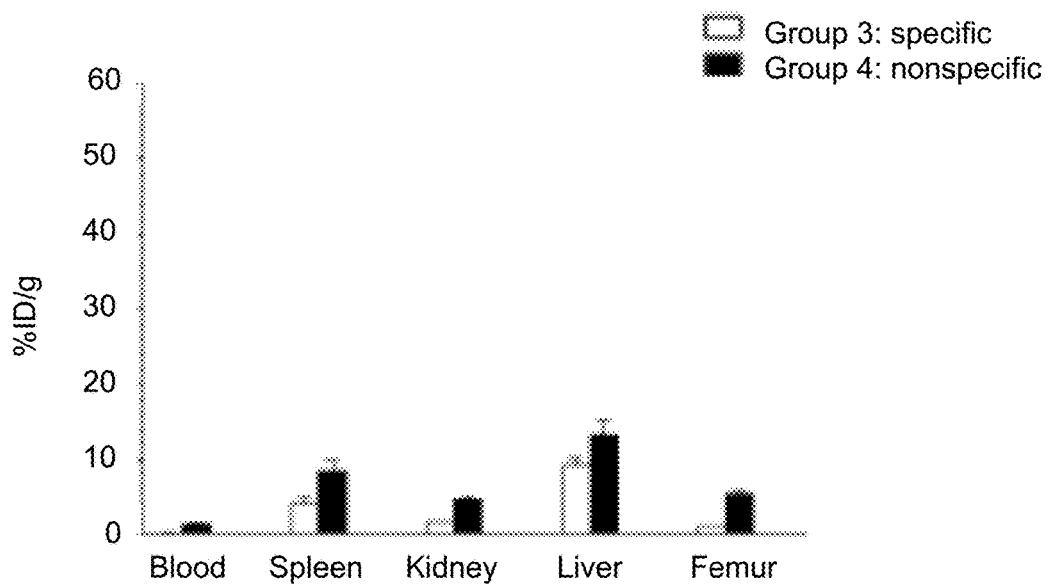

The specific targeting antibody construct [111In]Rituximab (group 6) served as a positive control for the antibody portion of the construct SWNT-rituximab-$^{111}$In*DOTA. The femurs of mice in group 1 accumulated 6.23±0.42% ID/g, whereas the femurs in group 6 mice accumulated 11.4±3.32% ID/g; these values were significantly different (P=0.0035). The specific construct SWNT-rituximab-$^{111}$In*DOTA (group 1) also showed statistically greater uptake (P=0.0035) in spleen than the nonspecific construct SWNT-HuM195-$^{111}$In*DOTA (group 2) of tumor-bearing mice (FIG. 12B).

The covalent attachment of antibodies to the SWNT scaffold dramatically altered the kidney biodistribution and pharmacokinetics as illustrated by the comparison of SWNT-$^{111}$In*DOTA and SWNT-rituximab-$^{111}$In*DOTA in tumor-bearing (groups 1 and 5 had 10.5±2.47% ID/g and 28.8±0.97% ID/g, respectively) versus nontumor-bearing mice (group 3 had 1.63±0.06% ID/g and SWNT-NH$_2$-DOTA in another biodistribution study (FIGS. 11A-11B, 13A-13B) had 41.06±3.09% ID/g) at 24 h.

Flow Cytometry of Bone Marrow

Figure 14:
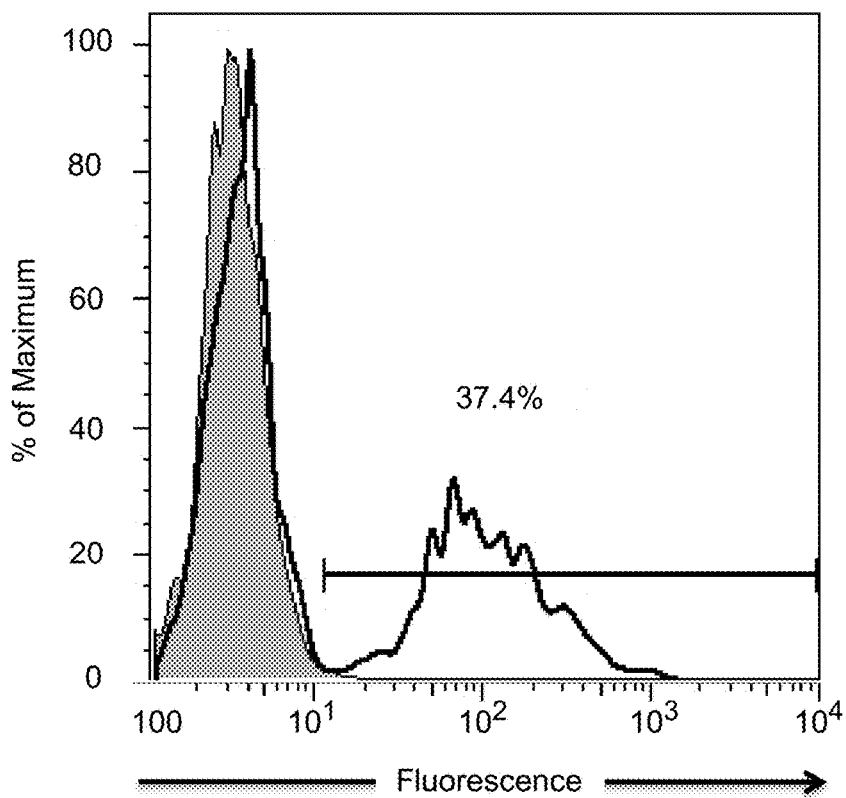
FIG. 14 is a flow cytometric demonstration of human lymphoma cells present in femurs of tumor-bearing mice 28 d after intravenous injection of GFP1/FFLuc1 Daudi cells into mice. Shown is overlay of single-parameter histograms of tumorbearing (solid-line trace) and nontumor-bearing (shaded histogram) mice. Fluorescence being measured is due to the GFP signal.

Twenty-eight days after intravenous injection of GFP+/FFLuc+ Daudi cells into scid mice, macroscopic, disseminated tumors developed in the bone marrow and spleen and in kidneys, liver, lungs, ovaries, and adipose tissue. BLI clearly showed the presence of lymphoma in the femur, spine, spleen, kidney, and, to a lesser extent, liver. The amount of tumor per tissue on a per-weight basis was spine (bone marrow)>spleen>kidney>liver (data not shown). Femurs from tumor and non-tumor bearing mice were removed and crushed by mortar and pestle in order to recover bone marrow. Assuming that 1×10$^9$ cells weigh about 1 g, the weight of the Daudi cells in the femur are estimated to be about 12 mg. For short SWNT-IgG constructs, 15 µg IgG on 3 µg of SWNTs was injected per mouse of which approximately 6% of the ID/g was targeted to the femur. Bone marrow was redissolved as a single cell suspension in FACS buffer (PBS/0.5% BSA/0.02% sodium azide). Cells were acquired on an FC500 cytometer and analyzed with FlowJo software for GFP expression. Flow cytometry on the bone marrow derived cells ($37 \times 10^6$ cells) indicate that about 37% were GFP positive Daudi cells. FIG. 14 demonstrates that the fluorescent GFP+/FFLuc+ Daudi cells were present in the marrow in the femurs of tumor-bearing mice.

Bioluminescence Imaging (BLI)

For quantitative assessment of GFP-Luc Daudi tumor burden by BLI, mice were anesthetized with isoflurane and received an i.p. injection of 3 mg/mouse D-Luciferin (Xenogen, Alamaeda, Calif.). Ten minutes later, mice were placed into the IVIS bioluminescence imaging system (Xenogen) and bioluminescence signal intensity was recorded. To assess the tumor burden in individual organs, mice were sacrificed and organs were removed immediately. The organs were placed in a 12-well plate with enough D-Luciferin (14 mg/ml) to cover the organ. The plate was immediately placed into the IVIS bioluminescence imaging system and bioluminescence signal intensity was recorded. Pseudocolor images showing the whole body or specific organ distribution of biolumnescent signal intensity were superimposed on conventional grayscale photographs.

Figure 15A:
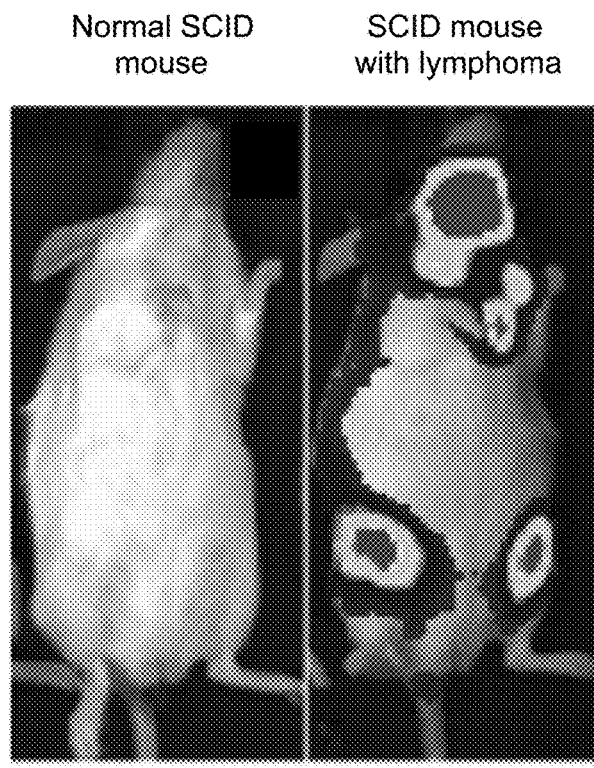

Twenty eight days after i.v. injection of Daudi cells, macroscopic, disseminated tumors develop in the lungs, kidneys, ovaries, and adipose tissue as well as in the spleen and bone marrow (37). Biodistribution was determined with targeted and control SWNT constructs. A comparison of bioluminescence images from normal and tumor-bearing SCID mice (FIG. 15A) clearly shows the presence of the Daudi cells in the femur and spleen (FIG. 15B) as well as in the kidney (FIG. 15C), spine (FIG. 15D) and, to a lesser extent, in the liver (FIG. 15E).

Example 11

SWNT-IgG-$^{111}$In*DOTA Constructs
Synthesis and Stability

The specific SWNT-rituximab-$^{111}$In*DOTA construct or control SWNT-HuM195-$^{111}$In*DOTA are prepared by adding 111-185 MBq of acidic $_{111}$In chloride to 0.50 mg of SWNT-rituximab-DOTA or SWNT-HuM195-DOTA (50 g/L) in MFW and 0.050 mL of 3 M ammonium acetate to yield a pH 5.5 solution. The reaction mixture was maintained at ambient temperature for 30 min and then purified using a 10DG column with 1% HSA/0.9% NaCl. The radiochemical purity was determined by the ITLC-SG methods described in Example 3.

Quantitative In Vitro Immunoreactivity of SWNT-IgG-$^{111}$In*DOTA Constructs

The binding efficiency of the CNT antibody hybrids was determined immediately after radiolabeling the hybrid. Target cells (Daudi) and control (HL60), $5 \times 10^6$ with greater than 90% viability were used for the assay. The SWNT-rituximab-$^{111}$In*DOTA construct (7 ng) was diluted in 2% human/bovine serum albumin (BSA; Sigma) and incubated on ice and at room temperature with cells pellets (n=3) of Daudi (CD20+, specific) and HL60 (CD20−, nonspecific) containing $3 \times 10^6$ cells in total volume of less than 200 µL at 4° C. and 37° C. The immunoreactivity was measured both on ice as well as physiologic temperature for periods of 30, 60, and 120 minutes with periodic light vortexing. After incubation the cells were washed twice with 1 mL of cold PBS and pelleted (1200 rmp for 5 minutes at 4° C.). The radioactivity of the resulting cell pellet and the two washes were collected and counted separately. The % immunoreactivity—(Cell pellet cpm/total cpm[cell pellet+wash 1+wash2])×100.

The stability of SWNT-rituximab-$^{111}$In*DOTA was determined in vitro by incubating the radiolabeled construc in human plasma at physilogic temperatures for 96 h and no significant change in the radiochemical purity was detected. An aliquot of SWNT-rituximab-$^{111}$In*DOTA in plasma was removed at 24 h intervals and the radiochemical purity was determined by ITLC as in Example 3. The purity was assayed to range between 90% and 94%, suggesting that the [$^{111}$In]DOTA-to SWNT thiourea bond and the $^{111}$In-to-DOTA coordination bonds were stable in human plasma over this 4 day period.

The $^{111}$In labeled SWNTs had about 25 rituximab (anti-CD20+) or HuM195 (anti-CD33) antibodies per SWNT. In these constructs the antibodies were attached randomly to the SWNT surface since the thiolation of the lysine groups, present both on the constant and binding regions, was a random event. It was contemplated that the binding kinetics of the large molecular weight, i.e., $2$-$6 \times 10^6$ Daltons, constructs to the cells might be slowed significantly.

Figure 16:
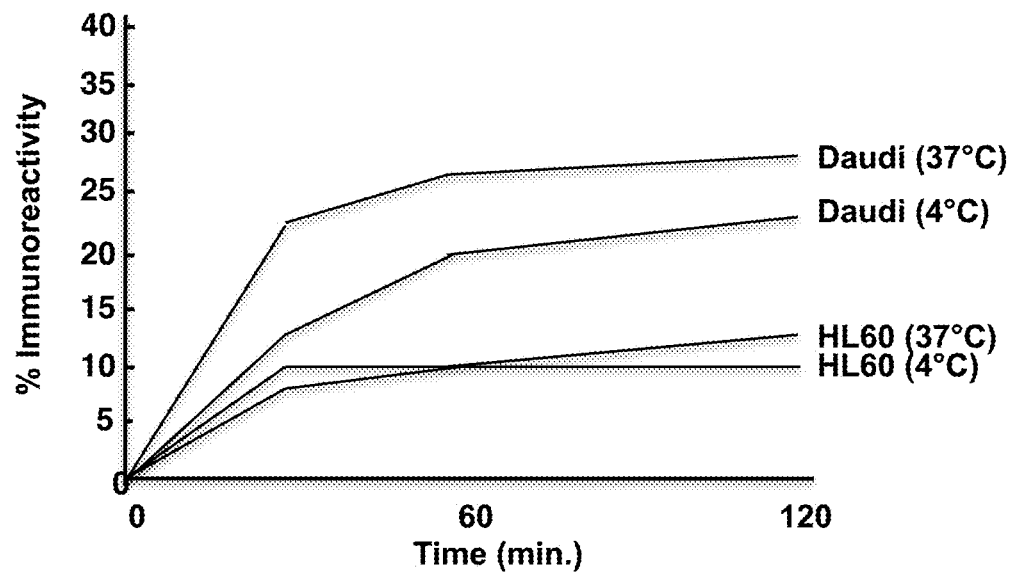
FIG. 16 depicts the cell-based immunoreactivity of SWNT-rituximab-$^{111}$In*DOTA as a function of time and temperature vs. specific (Daudi) and nonspecific (HL60) cell lines. Mean±SD values for each measurement are plotted.

The immunoreactive fraction of SWNT-rituximab-$^{111}$In*DOTA was measured in vitro using a live cell assay (57). On the basis of the time and temperature data from this assay, the binding kinetics of the construct appeared to be diffusion controlled, and the binding efficiency increased with both time and temperature (FIG. 16). The construct SWNT-rituximab-$^{111}$In*DOTA approached maximum binding after about 1 h, whereas the binding to the control cells was less. The maximum binding for this construct was 29%±0.5%, similar to the immunoreactive fraction of radiolabeled-rituximab measured previously as 42%±17% (33) (and repeated here; data not shown). The binding of SWNT-rituximab-$^{111}$In*DOTA to CD201 Daudi cells at 37° C. and 4° C. was statistically different (P<0.0001) as was the binding of SWNT-rituximab-$^{111}$In*DOTA to Daudi cells and CD20-HL60 cells at 37° C. (P<0.0001).

Example 12

SWNT-(IgG)$_m$-($^{225}$Ac*DOTA)$_n$ Constructs
Synthesis

The components of the construct molecule are synthesized as described in Examples 2-3. Generally, the maleimide-functionalized SWNTs are reacted with a mixture of intact anti-CD20 antibody rituximab or isotype control HuM195 (anti-CD33) and an Ac-225-radiolabeled DOTA-thiol complex. The DOTA-thiol is prepared by reaction of 1 equivalent of 2β-DOTA-NCS, 2-(p-isothiocyanatobenzyl)-1,4,7,10-tetraazacyclododecane-1,4,7,10-tetraacetic acid (Macrocyclics, Inc., Dallas, Tex.) with 1.3 equivalents of 2-mercaptoethylamine in dry N,N-dimethylformamide and triethylamine. This reaction proceeds instantaneously with 85% yield and yields a 92% pure product. The DOTA-thiol product can then be radiolabeled with Ac-225 for therapeutic applications (39). This strategy allows the stoichiometries m and n of antibody and radiometal to the nanotube to be varied. Purification is effected as described in Example 1.

Analysis of the final product is performed using AFM, fluorescence and UV-VIS spectroscopy, CE, and HPLC. In addition, an in vitro stability assay is performed by incubating construct in 100% human serum and 100% mouse serum at 37° C. over a 2 week period and analyzing the extent of construct degradation by size exclusion HPLC and immunoreactivity assay.

Example 13

Biodistribution of SWNT-Rituximab-$^{225}$Ac*DOTA Constructs

The biodistribution of the constructs is determined using a 20 g female CB17/ICR SCID mouse model (Taconic, Germantown, N.Y.) in both normal (non-tumor bearing) animals and tumor bearing animals as in Example 5.

A group (n=12) of normal mice receive approximately 0.5 mL of the SWNT-(anti-CD20)$_m$-(M*DOTA)$_n$ construct (350 nCi $^{225}$Ac) while another group (n=12) receive the non-targeting irrelevant (HuM195) control construct via i.p. injection. Three animals from each group are sacrificed at 48, 72, 120, and 168 hrs post injection. Blood and tissue samples, including heart, kidneys, lung, spleen, liver, stomach, intestine, and tumor, are harvested, weighed and are counted using a Packard Cobra Gamma Counter (Packard Instrument Co., Inc., Meriden, Conn.) with two energy windows, Fr-221 (185-250 KeV window) and Bi-213 (360-480 window). The percent of the injected dose per gram of tissue (% ID/g) is determined by measuring the activity in 0.025 mg aliquots of each respective construct injectate.

In a second experiment, two groups (n=12) of mice are xenografted with 5 million cells i.v. There is a 100% take rate of tumor in this model with death at 21 days. The animals are held for 2 weeks and then receive approximately 0.5 mL of CD20+ tumor targeting SWNT-(rituximab)$_m$-(M*DOTA)$_n$ construct (350 nCi $^{225}$Ac) or a similar amount of the non-targeting irrelevant control (HuM195) construct via i.p. injection. Three animals from each group are sacrificed at 48, 72, 120, and 168 h post injection. Blood and tissue samples are collected and are analyzed as described above.

Example 14

Synthesis of SWNT-(DNA-(IgG)$_m$-(M*DOTA)$_n$) Constructs

Figure 17:
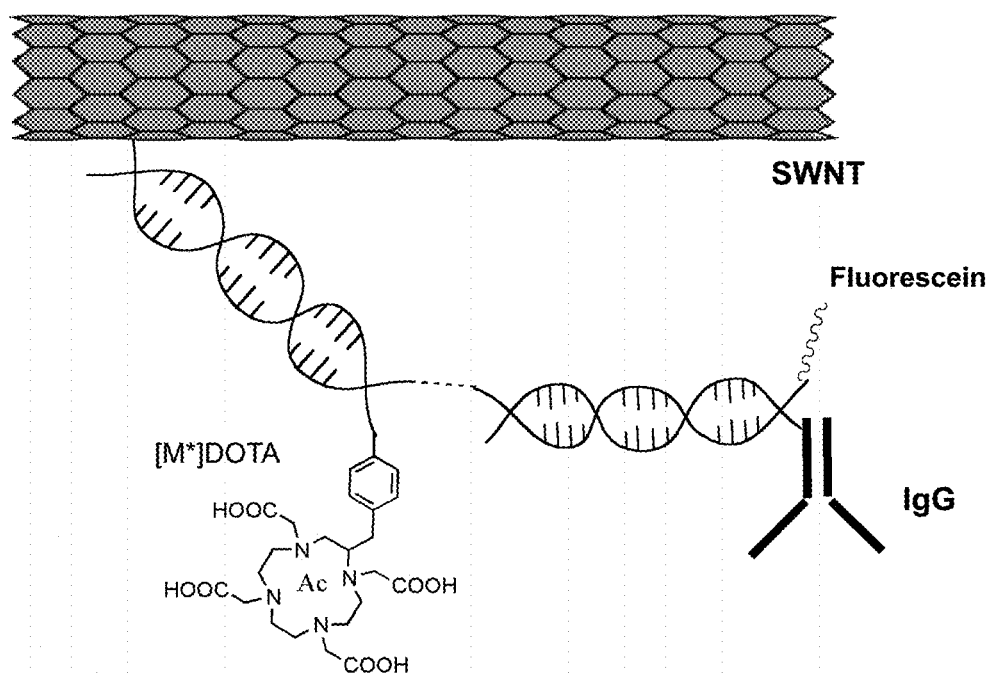
FIG. 17 is a cartoon of the SWNT-(DNA)-(rituximab)$_m$-(Ac-225*DOTA)$_n$) construct.

SWNT-(DNA-(IgG)$_m$-(M*DOTA)$_n$) construct (FIG. 17) is synthesized using chemical steps described in Example 2. Each of the three components is built individually. First, SWNTs with appended reactive maleimide functionalities are prepared as described in Example 2. This compound is now reactive toward thiolated compounds. The oligodeoxynucleotide (ODN) to be coupled to the SWNT is fluorescein labeled 5'-(FAM)-TAG-TGT-TGA-CGA-AGG-GAC-(PEG150)-TAT-GGG-TCA-TCG-TAC-GAC-(C$_6$—SH)-3' (SEQ ID NO: 1; Trilink Biotechnologies, San Diego, Calif.) and is referred to as FAMODN36SH. The ODN is obtained as the disulfide and is reduced using Reduce-IMM Immobilized Reducing Kit (Pierce, Rockford Ill.) to yield the reactive ODN thiol. The activated ODN is added in 100-fold stoichiometric excess to LC-SMCC functionalized SWNTs. The reaction mixture is purified by size exclusion chromatography or Centricon methodology. Removal of excess unreacted ODN is crucial. Analysis of the final product is performed using AFM, fluorescence and UV-VIS spectroscopy, CE, and HPLC.

Backbone modification of the oligodeoxynucleotides was performed to enhance in vivo stability. For example, phosphorothiolate backbone substituted oligodeoxynucleotides exhibit greater stability in mice when compared to phosphodiester backbone substituted oligodeoxynucleotides while being biodistributed in a similar fashion (40). The SWNT now contains ODNs with 2 different complementary sequences and a fluorescein tag.

Second, a maleimide-functionalized anti-CD20 antibody is prepared by exposing thiols on the antibody and reacting with Sulfo-SMCC (Pierce, Rockford Ill.). Approximately 8 maleimide groups per IgG are appended. A parallel reaction with HuM195 (anti-CD33) monoclonal antibody is performed to yield an irrelevant isotype control. The reaction mixture is purified by size exclusion chromatography to remove the excess sulfo-SMCC and yield pure maleimide-modified antibody.

An ODN that is complementary to the distal 18 mer sequence on FAMODN36-SWNT 5'-GTC-CCT-TCG-TCA-ACA-CTA-(C$_6$—SH)-3' (SEQ ID NO: 2) is reacted with the maleimide-functionalized IgG. This activated ODN has a PS backbone and the calculated T$_m$ is 48° C. and is referred to as CODNdis (Trilink Biotechnologies). Reaction of a 20-fold excess of CODNdis with the maleimide-functionalized IgG yields a CODNdis-IgG construct. The reaction mixture is purified by size exclusion chromatography.

Third, a DOTA-ODN is prepared by reaction of 1 equivalent of 2B-DOTA-NCS, 2-(p-isothiocyanatobenzyl)-1,4,7,10-tetraazacyclododecane-1,4,7,10-tetraacetic acid (Macrocyclics, Inc., Dallas, Tex.) with 1.2 equivalents of 5' ATA-CCC-AGT-AGC-ATG-CTG-(C$_3$—NH$_2$) 3' (SEQ ID NO: 3) in dry N,N-dimethylformamide and triethylamine. This oligo has a PS backbone and is a sequence complementary to the ODN sequence proximal to the SWNT with a calculated Tm of 47° C. This ODN is referred to as CODNprox (Trilink Biotechnologies). This reaction proceeds with heating and with an approximately 30% yield. The reaction mixture is purified by Reverse Phase SeP-Pak to desalt the product. Analysis of the final product is performed using radiolabeling, UV-VIS spectroscopy, CE, and HPLC. The DOTA-CODNprox product can then be radiolabeled with Ac-225 for therapeutic applications or In-111 for diagnostic applications as previously described (39).

The number of FAMODN36-substituents per SWNT is determined spectroscopically using the fluorescein chromophore. This number of oligodeoxynucleotides per SWNT, I, determines the stoichiometric amounts of complementary CODNdis-IgG construct and complementary M*DOTA-CODNprox that are reacted to assemble the complex. It is contemplated that 1<m<5 equivalents of CODNdis-IgG construct are added initially and then titrating the M*DOTA-CODNprox from 1<n<the maximum. The maximum could be on the order of 500 equivalents. This would insure that every targeting SWNT-(DNA-(IgG)$_m$-(M*DOTA)$_n$) construct contained at least 1 Ac-225. This is a consequence of 1 in 500 DOTA molecules being radiolabeled. Once fully assembled SWNT-DOTA-IgG are made, it is contemplated further that they can be assembled in vitro in cells in the order SWNT-DNA-IgG followed by DOTA-DNA. The SWNT-(DNA-(IgG)$_m$-(M*DOTA)$_n$) constructs are physically and biologically characterized as described in Example 12.

Therapy Experiments in a Tumor Model

Five groups of ten female CB17/ICR SCID mice are xenografted with 5 million cells i.v. of GFP-PSA-Daudi cell line in Example 8. Tumor take rate is 100% and the median time to death in a 20 g mouse is 21 days). The five experimental therapy groups examine 1) treatment with 250 nCi of SWNT-(DNA-(rituximab)$_m$-(Ac-225*DOTA)$_n$) construct assembled pre-injection; 2) treatment with 250 nCi of SWNT-(DNA-(HuM195)$_m$-($^{225}$Ac*DOTA)$_n$) control construct assembled pre-injection; 3) treatment with 250 nCi of SWNT-(DNA-(rituximab)$_m$-($^{225}$Ac*DOTA)$_n$) construct assembled in vivo; 4) treatment with 250 nCi of SWNT-(DNA-(HuM195)$_m$-($^{225}$Ac*DOTA)$_n$) control construct assembled in vivo; and 5) untreated growth control.

Seven days post xenograft, tumor growth is assessed via PSA levels in serum. This measurement confirms the presence and extent of tumor growth, i.e., where measurable serum PSA>1 ng/mL. In addition, 3 animals from each group are optically imaged at this time. On day 12, each of the 5 groups of animals is treated via intraperitoneal injection as described above. The individual mouse serum PSA levels are measured on day 20 and thereafter as a function of time, i.e., approximately every 2 weeks, in each of the treatment and control groups. The same three mice are optically imaged at these PSA assay time points. Animals that are sacrificed due to progression of disease will be optically imaged and blood collected to assay the PSA level prior to sacrifice. Survival fractions between the various treatment and control groups will be compared using Kaplan-Meier analyses.

Assembly in vivo can utilize several possible routes for treatment and schedules. Route 1 utilizes FAMODN36-SWNT which can be annealed with a fixed number of CODNdis-IgG at the bench and injected followed by M*DOTA-CODNprox injection. This approach is similar to other pretargeting methods which employ avidin and biotin. In Route 2, all 3 parts can be separately injected. This approach would require the two complementary annealing steps proceed efficiently so that both targeting and therapy are effective.

Example 15

Use of Self-Assembling Constructs to Build an Enzymatic Nanofactory

In Vitro Assembly of the Enzymatic Nanofactory

First the antibodies are conjugated to the SWNTs and the extent of derivatization is estimated by the shift in apparent molecular weight of the constructs. Then the fluorescent oligonucleotide is added to the preparation, and its coupling to the SWNTs is assessed by the appearance of a fluorescent peak at the same retention time on the chromatogram. Purification is performed by preparative size-exclusion FPLC. Functionalization of the enzyme with the complementary oligonucleotide also is performed through thiol/maleimide chemistry as is described in Example 3. The complementary oligo bears a different fluorescent tag. The optimal extent of derivatization is determined by measuring the enzymatic activity after functionalization with varying amounts of maleimide groups. Purification will be performed by preparative SE-FPLC. The kinetics of the self-assembly of the nanofactory will be assessed by SE-HPLC analysis at different time points. Appearance of a high molecular weight peak having the fluorescent properties of both tags will indicate assembly of the nanomachine.

Figures 18A, 18B, 18C:
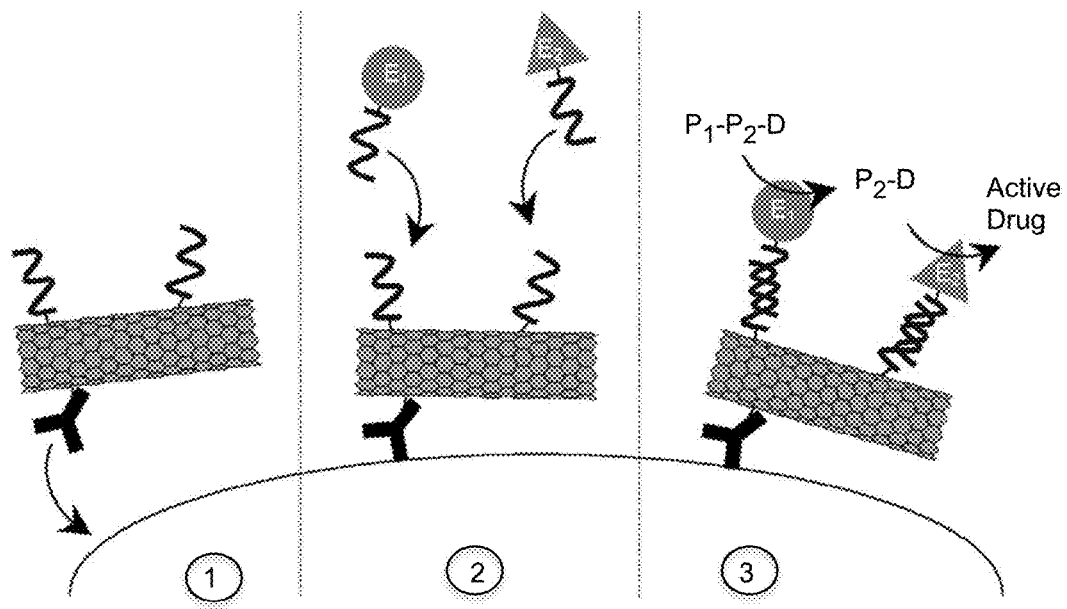
FIGS. 18A-18D illustrate the general scheme for pre-prodrug activation on a SWNT platform using two activating enzymes (FIGS. 18A-18C) and a particular scheme for cleavage of pre-pro-doxirubicin cleavage using carboxypeptidase A and β-glucuronidase (FIG. 18D).

The ability of the construct to bind to target cells is verified as in Example 5 (FIG. 18A). This is performed by direct FACS analysis, using the fluorescent tags of the oligos as a readout. Controls with free oligos and enzyme-oligos are included in the study. (FIG. 18B). The results determine whether the SWNTs prevent internalization of the conjugated antibodies.

The ability of the nanofactory to convert a prodrug into drug is assessed by reversed-phase HPLC. The purified nanofactory is incubated with the prodrug for varying amounts of time and aliquots of the reaction mixture are injected and are analyzed in comparison to drug and prodrug standards. It is expected that progressive disappearance of the prodrug with concomittant appearance of the drug will occur. Controls are run in parallel to assess the specificity of the prodrug cleavage. The efficiency of the nanopharmacy at specifically killing target cells is tested by incubating HL-60 cells with the construct, washing the cells, and then adding the prodrug. Cell toxicity is measured, in comparison with a control not treated with the construct, or with cells receiving both treatments, but lacking the target antigen.

Two distinct activating enzymes may be incorporated on the SWNTs for activation of a pre-prodrug (FIG. 18C). An example of an enzyme/pre-prodrug system relies on the sequential activation of a drug by carboxypeptidase A and β-glucuronidase. The key element in this strategy is that only after cleavage by both enzymes will the prodrug deliver the active drug. Only after cleavage of the first protecting group by carboxypeptidase A will β-glucuronidase be able to cleave the glucuronoconjugate, therefore releasing the active drug. The prodrug of doxorubicin has been extensively studied (41).

It is contemplated that derivatization of the carboxylic acid of the glucoronic acid moiety will prevent its recognition as a substrate by β-glucuronidase. It has been shown that this moiety constitutes an important substrate recognition determinant for α-glucuronidases, and likely acts the same way with β-glucuronidases (42). Hence, addition of a peptide substrate for carboxypeptidase A at that position will prevent cleavage of this pre-prodrug by β-glucuronidase. But preliminary cleavage of that peptide by carboxypeptidase A will restore recognition of the prodrug by β-glucuronidase and subsequently release doxorubicin.

Figure 18D:
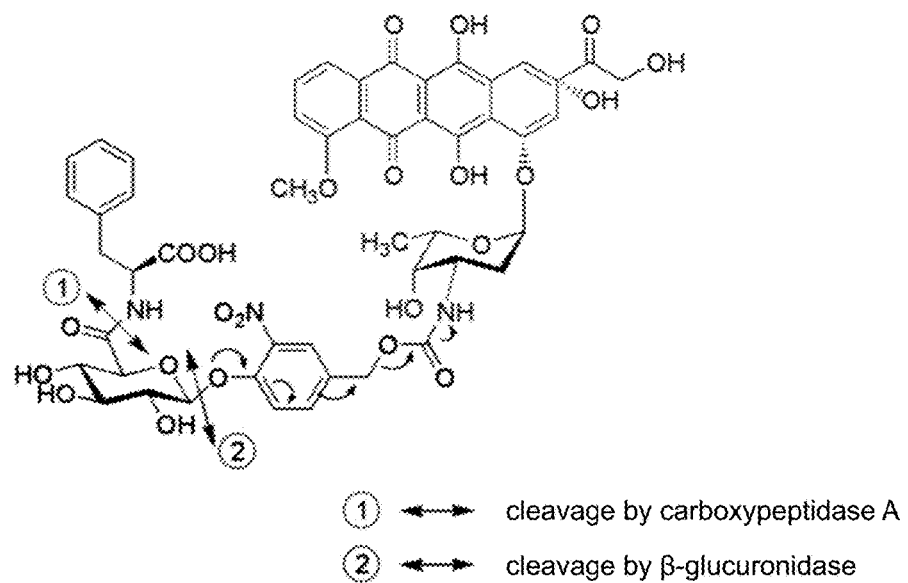

Pre-pro-doxorubicin is sequentially cleaved by CPA and beta-glucuronidase (FIG. 18D). After cleavage of the glycosidic bond, the self-immolative spacer is quickly released by breaking the benzyl-carbamate bond. The resulting doxorubicin carbamate is unstable and rapidly loses $CO_2$ to generate free doxorubicin. CPA is an exoprotease which removes preferentially aromatic aminoacid acids from the C-terminal of a peptide chain. A phenylalanine residue on the glucuronide prodrug is tested as a substrate for CPA, since that approach has proven successful for an ADEPT prodrug (43). CPA does not specifically require an aminoacid residue at the $P_1$ site, so it is expected that this molecule will be a substrate for the enzyme (44). However, the possibility that the enzyme will not be able to remove this residue when bound to glucuronic acid must be considered. In that case, a substrate dipeptide may be incorporated on the prodrug. Restoration of the carboxylic acid moiety on the glucuronic acid then is performed through the use of an appropriate self-immolative linker.

In Vivo Study of the Enzymatic Nanofactory

The in vivo use of the targeted enzymatic nanofactory requires self assembly at the tumor site similar to that described in Example 14. Biodistribution of the radiolabeled enzyme-oligo conjugates will be studied in a xenograft tumor model in mice after prior injection of the SWNT addressing platform as in Example 8. A control experiment where mice are not treated with that platform determines whether specific localization of the enzymes at the tumor site is achieved using this strategy.

The efficacy of in vivo use of the enzymatic nanofactory in tumor-xenografted mice sequentially treated with the addressing platform, the enzyme-oligo conjugates, and the pre-prodrug is determined as in Example 8. Groups of 5 mice, each bearing CD20 positive tumor are injected with Antibody-DNA-SWNT, followed by anti-sense DNA-enzyme, followed by pre-prodrug. It is expected that dosing, scheduling, and interval times between each of the 3 steps will require considerable trial and error to optimize specificity and potency. Multiple experiments will be necessary. Controls using drug alone or SWNT alone, and tumors that are CD20 negative will also be assessed. These experiments can be done as described for the targeted isotope generators in Example 5.

PSMA+ prostate cancer and a CD33+ myeloid leukemia murine models may be used. Methods are the same as described for the CD20 system except for the change in antibody and cell targets. These models allow comparison of results in tumors that are solid (prostate) or rapidly modulating (leukemia) in order to better understand the pharmacology of the SWNT.

Example 16

SWNT-Based Tumor Vaccines
Bone Marrow Derived Dendritic Cells

Murine femurs and tibias are isolated, cleaned and bone marrow is removed with sterile PBS and a 25 gauge needle. After red blood cell lysis, cells are incubated in RPMI media containing GMCSF. The following day, non-adherent cells are removed. On day 4, the immature dendritic cells that begin to pop off the plates are removed and incubated with GMCSF. On day 7, mature dendritic cells can be harvested and stained with CD11c to estimate purity.

Antigen Processing

It is known that carboxyl-terminal residues contribute significantly to the efficiency of class I presentation. While aromatic, basic and small aliphatic residues lead to a more efficient epitope recognition, acidic and helix breaking residues significantly inhibit the recognition. Therefore, various constructs listed in Table 2, containing the OVA CD4+ and CD8+ peptide epitopes, are linked to the maleimide functionalized SWNT of various lengths, incubated with APCs and assayed for the presentation of peptides on the surface of the cells. A clear advantage to using the OVA system is that an MHC-peptide complex specific mAb, 25-D1.16, is available, enabling these assays to be analyzed via FACS (38). For all other peptides, $^{125}$I labeling via lysine residues will allow for the analysis of peptides.

TABLE 2

| Abbreviation | Description | SEQ ID NO: | Sequence |
|---|---|---|---|
| CD8-short-N | Minimal CD8 epitope | 4 | CSIINFEKL |
| CD8-short-C | Minimal CD8 epitope | 5 | SIINFEKLC |
| CD8-long-N | CD8 plus flanking amino acids | 6 | CEVSGLEQL ESIINFEKL |
| CD8-long-C | CD8 plus flanking amino acids | 7 | SIINFEKLT EWTSSNVME ERC |
| CD4-short-N | Minimal CD4 epitope (contains a B cell epitope) | 8 | CISQAVHAA HAEINEAGR |
| CD4-short-C | Minimal CD4 epitope (contains a B cell epitope) | 9 | ISQAVHAAH AEINEAGRC |
| CD4-CD8-N | CD4 plus CD8 flanking amino acids | 10 | CISQAVHAA HAEINEAGR ESIINFEKL TEWT |
| CD4-CD8-C | CD4 plus CD8 flanking amino acids | 11 | ISQAVHAAH AEINEAGRE SIINFEKLT EWTC |
| CD8-CD4-N | CD8 plus CD4 flanking amino acids | 12 | CEQLESIIN FEKLTEKIS QAVHAAHAE INEAGR |
| CD8-CD4-C | CD8 plus CD4 flanking amino acids | 13 | EQLESIINF EKLTEKISQ AVHAAHAEI NEAGRC |

Following incubation of APCs with SWNT-peptide constructs, the peptides in the MHC molecules are stripped and analyzed in the gamma-counter to determine if these peptides are cleaved properly and are processed by the proteosome, if the addition of a cysteine residue at the N or C terminal effect the presentation of the peptide, what is the minimum or maximum length of the peptides necessary for processing, if the requirements differ for CD4+ or CD8+ epitopes; if the synthesis of CD4+ and CD8+ epitopes together aid in the presentation and if the density of peptides on the SWNT correlate with level of presentation.

Immunization with Synthetic Peptide Epitopes

Mouse footpads of C57BL/6 or BALB/c, depending on the peptide specificity, are injected with the various OVA constructs in the presence or absence of adjuvant (Titermax, Sigma) along with appropriate control groups. Serum from immunized animals is obtained via retro-orbital bleeding and assayed for SWNT specific Abs using the ELISA protocol described above.

IFN Gamma ELISPOT Assay

Figure 19:
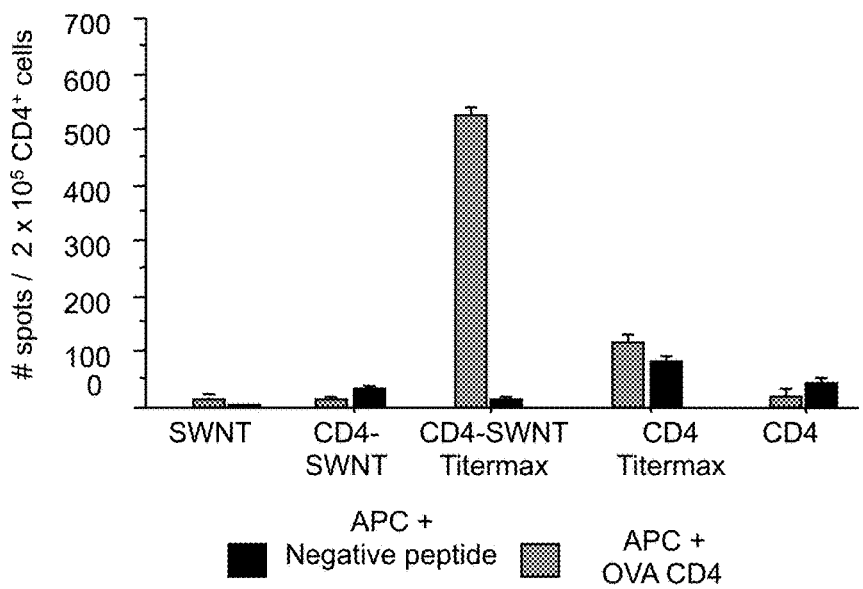
FIG. 19 demonstrates that OVA CD4+ peptides linked to SWNTs activated a greater number of CD4+ T cells in the presence of adjuvant than an equal amount of CD4+ peptide alone or with adjuvant.

HA-Multiscreen plates were coated with rat-anti-mouse IFN-g antibody (MabTech). CD8+ T cells isolated and purified from the paplitial lymph nodes of immunized animals are plated, and APCs from a non-immunized mouse are isolated, irradiated, pulsed with peptides, and added to the CD8+ T cells at an E:T ratio of 1:4. The cellular mixture is incubated overnight at 37° C. and the plates were developed the next day using an antibody against rat IgG. Spots were counted using a computer assisted video image analyzer with KS ELISPOT 4.0 software (Carol Zeiss Vision, Germany). FIG. 19 demonstrates OVA CD4+ peptides linked to SWNT were able to activate a greater number of CD4+ T cells than an equal amount of CD4+ peptide alone. Interestingly, the SWNT was unable to act as an adjuvant. It will be determined whether the addition of more peptides to the tubes generates a more robust immune response.

Selection of Synthetic WT-1 CD8+ Peptide Epitopes

Using the BIMAS computer based algorithm software, six peptides from the murine WT-1 protein with comparatively high binding to MHC H-2K$^d$ and four peptides with comparatively high binding to MHC H-2D$^b$ were selected and synthesized. In addition, heteroclitic peptides having anchor residue mutations in each of these peptides were synthesized which leads to a higher predicted binding. Tables 3 and 4 show the name and sequence of predicted native and heteroclitic WT1 specific CD8+ peptide epitopes. It is contemplated that, using the human HLA-DR+ peptide LVRHH-NMHQRNMTKL (SEQ ID NO: 14) as a template, further native and heteroclitic murine CD4+ WT-1 epitopes may be identified and synthesized.

TABLE 3

WT-1 MHC I (H-2Kd) peptides

| Name | SEQ ID NO: | Sequence | | Predicted Half Life |
|---|---|---|---|---|
| WTI-10 | 15 | ALLPAVSSL | 10-18 | 115 |
| WTI-10A | 16 | AYLPAVSSL | | 5760 |
| WTI-126 | 17 | RMFPNAPYL | 126-134 | 57 |
| WTI-126A | 18 | RYFPNAPYL | | 2880 |
| WTI-136 | 19 | SCLESQPTI | 136-144 | 115 |
| WTI-136A | 20 | SYLESQPTI | | 5760 |
| WTI-239 | 21 | NQMNLGATL | 239-247 | 115 |
| WTI-239A | 22 | NYMNLGATL | | 5760 |
| WTI-285 | 23 | QYRIHTHGV | 285-293 | 600 |
| WTI-285A | 24 | QYRIHTHGL | | 2400 |
| WTI-424 | 25 | KFARSDELV | 424-432 | 288 |
| WTI-424A | 26 | KFARSDELI | | 1152 |

TABLE 4

WT-1 MHC I (H-2Dd) peptides

| Name | SEQ ID NO: | Sequence | | Predicted Half Life |
|---|---|---|---|---|
| WTI-126 | 27 | RMFPNAPYL | 126-134 | 1990 |
| WTI-126B | 28 | RMFPNAPYM | | 1990 |
| WTI-221 | 29 | YSSDNLYQM | 221-229 | 930 |
| WTI-221A | 30 | YMSDNLYQM | | 1422 |
| WTI-228 | 31 | QMTSQLECM | 228-236 | 33 |
| WTI-228A | 32 | QMTSNLECM | | 3370 |
| WTI-235 | 33 | CMTWNQMNL | 235-243 | 5255 |
| WTI-235A | 34 | CMTWNQMNM | | 3754 |
| WTI-126 | 35 | RMFPNAPYL | 126-134 | 1990 |

Figure 20:
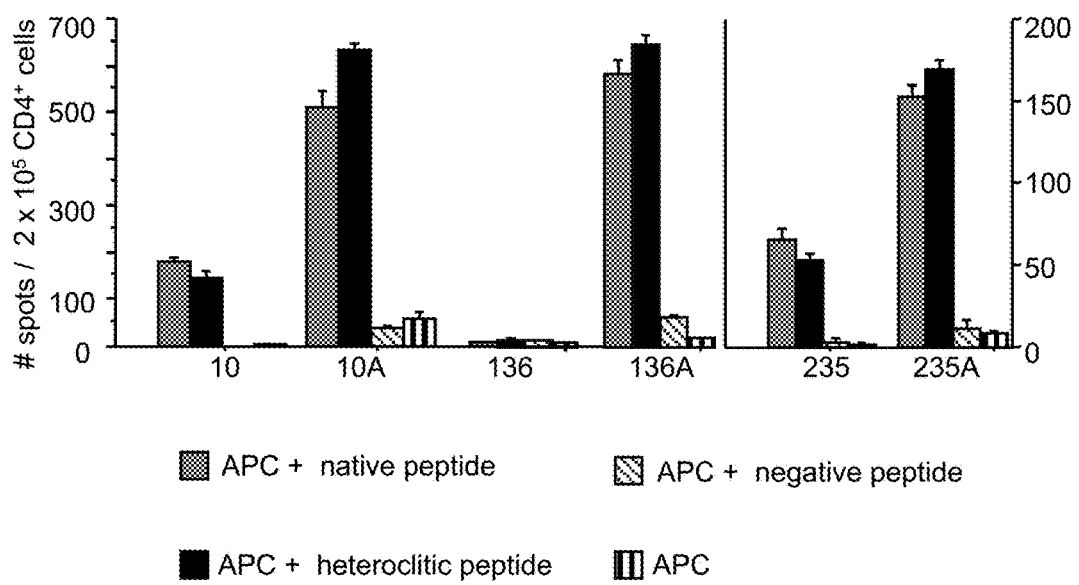
FIG. 20 illustrates that native and heteroclitic WT1 peptides incorporated on SWNTs elicit WT1 peptide specific CTL responses in vivo.

A few of these peptides were screened for their ability to elicit WT-1 peptide specific CTL responses in vivo using the methods described above. The mutated peptides WT1-10A and WT1-136A and WT-1 235A generated a robust immune response, but more importantly, stimulated CD8+ T cells that cross reacted with the native sequence, which the native sequences, WT1-10, WT1-136 or WT1-235 were unable to do (FIG. 20).

$^{51}$Cr Cytotoxicity Assay

Figure 21:
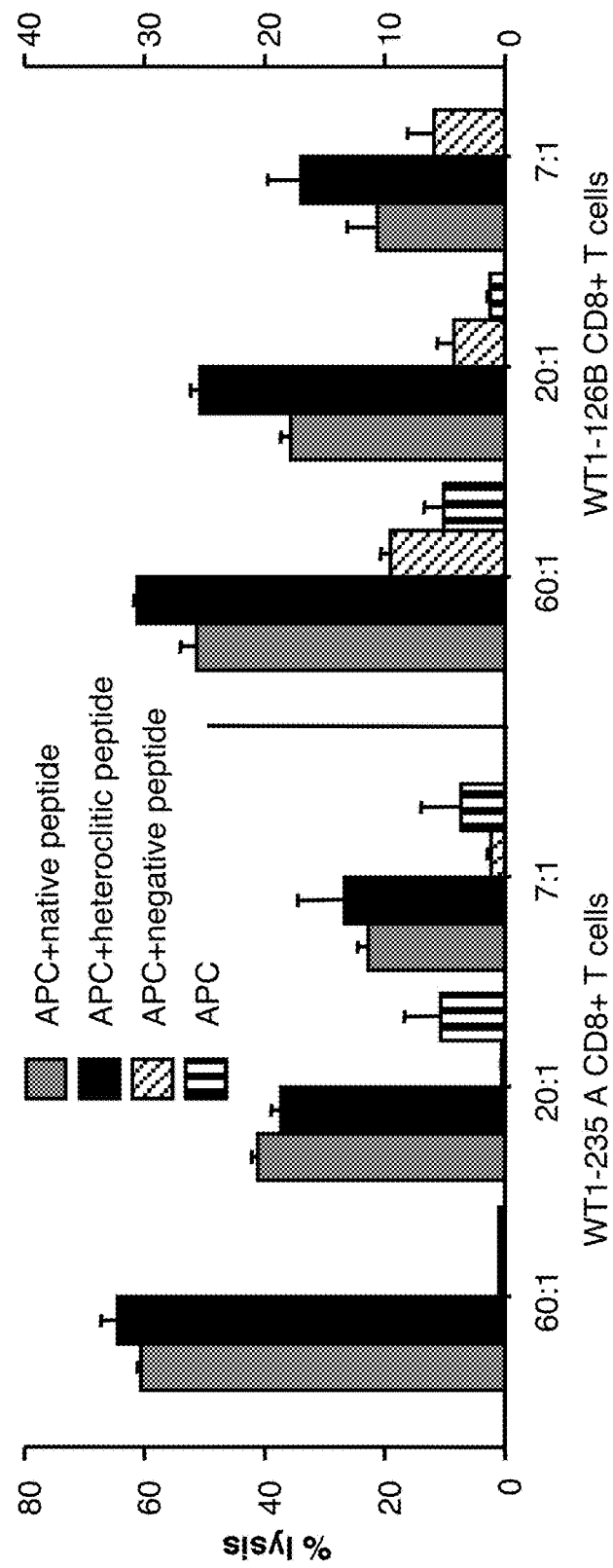
FIG. 21 depicts a $^{51}$Cr cytotoxicity assay demonstrating that peptides WT1-126A and WT1-235A stimulate a heteroclitic response in CD8+ T cells which kill native peptide pulsed APCs.

To detect the cytotoxic nature of the activated CD8+ T cells peptide specific CD8+ cells and irradiated peptide pulsed APCs were prepared as described above. The peptide sensitized APCs were labeled with 100 μCi of $^{51}$Cr and incubated together with the CD8+ cells at E:T ratios varying from 1:60-1:7. After incubation together for 4 hours, supernatants were harvested and measured in a gamma counter. Peptides WT1-126A and WT1-235A were able to stimulate a heteroclitic response and the CD8+ T cells killed pulsed targets (FIG. 21).

CTLs generated from immunizations with these peptides will be tested against WT-1 expressing murine tumor cells such as TRAMP-C (prostate cancer—H-2Kb), FBL3 (leukemia—H-2Kb) and AB12 (mesothelioma—H-2Kd). Previous reports have identified native peptides WT1-126 (41) and WT1-235 (42) as CD8+ epitopes. They have had limited ability to kill tumor expressing cells or to produce a successful vaccine. It is contemplated that the heteroclitic peptides will be able to better stimulate a response and that conjugating these peptides to SWNT will greatly enhance the CD8+ activity. In order to conjugate these peptides to SWNT, additional cysteine residues will be added to the N or C terminal portion of these peptides, as necessary.

Effect of SWNT-Peptide Vaccine Against Tumors

EL4 tumor cells transfected with OVA (43) or the WT-1+ tumor cells are injected into an appropriate murine model. The mice are vaccinated with a SWNT-peptide construct that is non-toxic, whose peptides are properly presented in MHC molecules at the surface of APCs and is able to elicit a strong CD8+ immune response to determine if the vaccination schemes can protect against tumor challenge or if established tumors will shrink.

Example 17

Synthesis of SWNT-(DNA$_{12}$-(cDNA$_1$-cRGD)$_m$-(cDNA$_2$-M*DOTA)$_n$)$_x$ Construct The ODN-Modified SWNT Platform: SWNT-(DNA$_{12}$)$_x$ The ODN-modified SWNT platform SWNT-(DNA$_{12}$)$_x$ is synthesized as described in Example 1. 5'-(Cy3)-TAG-TGT-TGA-CGA-AGG-GAC-(PEG150)-TAT-GGG-TCA-TCG-TAC-GAC-(C$_6$-SH) 3' (SEQ ID NO: 1) is synthesized and purified as described in Example 12 except that Cy3 fluorophore is coupled to the 5' end. The thiol-activated ODN is reacted in stoichiometric excess to maleimide functionalized SWNT. The stoichiometry will be varied to produce SWNT-(DNA$_{12}$)$_x$ with several different values of x. It is intended that the range is 1≤x≤100. The SWNT now contains x appended ODNs each with two different information addresses and a Cy3 chromophore. Visible spectroscopic analysis of the Cy3 chromophore allows for determination of the extent of substitution which yields the stoichiometric value of x.

The ODN-Modified cRGD Targeting Peptide: (cDNA$_1$-cRGD)$_m$

The terminal amine of 5' GTC-CCT-TCG-TCA-ACA-CTA-C$_6$-NH$_2$ 3' (SEQ ID NO: 2) is sulfo-SMCC activated to yield 5'-GTC-CCT-TCG-TCA-ACA-CTA-C$_6$-SH-3'. The reaction mixture will be chromatographed over poly-lysine resin to remove the excess sulfo-SMCC and yield pure maleimide-modified ODN. cRGDf (e-S-acetylthioacetyl)K (Ansynth, Roosendaal, the Netherlands) is deprotected by reaction with hydroxylamine in situ. This yields a reactive cRGD-thiol. The maleimide-activated ODN and the deprotected peptide are reacted using a 1:2 stoichiometry.

The reaction mixture is purified by Reverse Phase SeP-Pak to desalt the product using a preparative divinylbenzene (DVB) cartridge (Alltech, 500 mg, 4.0 mL) with a negative pressure and a flow rate 1-2 mL/min. The DVB cartridge is conditioned with 2 mL each of absolute ethanol, metal-free water, and 0.15M NaCl. The reaction mixture is loaded in 1.5 mL of volume. The cartridge is washed with 20 mL metal-free water. The product is eluted in 2 mL of absolute ethanol and the ethanol will be removed by rotoevaporation. Analysis of the final product will be performed using UV-VIS spectroscopy, CE, and HPLC. The control peptide, cRAD (e-S-acetylthioacetyl)K, is reacted and purified using a similar scheme.

The ODN-Modified DOTA Chelate: (cDNA$_2$-DOTA)$_n$

Metal-free reagents must be used. Sulfo-SMCC is used to activate the primary amine of DOTA-CH$_2$—Bz-NH—C(S)—NH—(CH$_2$)$_3$—NH$_2$ (Macrocyclics, Inc. (Dallas Tex.). The reaction mixture is purified as described above to yield maleimide-modified DOTA, i.e., DOTA-NCS. 5'-ATA-CCC-AGT-AGC-ATG-CTG-C$_3$-SH-3' (SEQ ID NO: 3) is reduced using Reduce-IMM Immobilized Reducing Kit (Product 77700; Pierce, Rockford Ill.) to yield the reactive thiol. The reduced ODN-thiol is coupled to the sulfo-SMCC activated DOTA using a 1:2 reaction stoichiometry. The reaction mixture is purified and analysed as is (cDNA$_1$-cRGD)$_m$.

Radiolabeled (cDNA$_2$-M*DOTA)$_n$

For In-111 labeling, an acidic In-111 chloride solution (Perkin Elmer, North Bellirica, Mass.) is adjusted to pH 4-4.5 with the addition of 0.10 mL of 3 M ammonium acetate. To this solution 0.1 mg of the cDNA$_2$-DOTA construct is added. Reactions approach 100% completion in approximately 20 minutes at ambient temperature and are quenched with the addition 0.020 mL of 10 mM EDTA.

For Ac-225 labeling, an acidic Ac-225 chloride solution (Oak Ridge National Laboratory, Oak ridge, Tenn.) is adjusted to pH 4-4.5 with the addition of 0.05 mL of 2 M tetramethylammonium acetate and 0.05 mL of 5 g/L l-ascorbic acid. To this solution 0.5 mg of the cDNA$_2$-DOTA construct is added. Reactions reach approximately 90-100% completion in approximately 30 minutes at 60° C. and are quenched with the addition 0.020 mL of 10 mM DTPA.

Assembling SWNT-(DNA$_{12}$-(cDNA$_1$-cRGD)$_m$-(cDNA$_2$-M*DOTA)$_n$)$_x$

The stoichiometric number of oligodeoxynucleotides per SWNT, x, is determined spectrophotometrically. The stoichiometric equivalents of cDNA$_1$-cRGD targeting peptide, m, and cDNA$_2$-M*DOTA, n, to be reacted with SWNT-(DNA$_{12}$)$_x$ are varied systematically to produce constructs with different compositions. Assume that the molecular weights of these components are 7700 for cDNA$_1$-cRGD, 7925 for cDNA$_2$-$^{225}$Ac*DOTA, and 1060000 g/mol for l=500, d=1 nm SWNT-(DNA$_{12}$)$_{50}$. If both m and n can be titrated onto a SWNT-(DNA$_{12}$)$_{50}$ in stoichiometries ranging from 1 to 50, then the molecular weight of the completed construct can vary from 1080000 to 1840000 g/mol. Table 5 is a SWNT stoichiometry and MW calculator per construct.

TABLE 5 x is the number of DNA1,2 per SWNT, m is the number of peptide-DNA1, n is the number of [M]DOTA-DNA2

| Item | D(nm) | L (nm) | C (molecules) | MW (g/mol) |
|---|---|---|---|---|
| SWNT-2000 | 1 | 2000 | 120000 | 14400000 |
| SWNT-1000 | 1 | 1000 | 60000 | 720000 |
| SWNT-500 | 1 | 500 | 30000 | 360000 |
| SWNT-250 | 1 | 250 | 15000 | 180000 |
| SSWNT-50 | 1 | 50 | 3000 | 36000 |
| 36 mer DNA | | | | 15000 |
| Peptide-18 mer DNA | | | | 7700 |
| [AC-225]DOTA-18 mer DNA | | | | 7925 |

| Code | x | m | n | MW (g/mol) |
|---|---|---|---|---|
| SWNT-1000 | 50 | 0 | 0 | 1470000 |
| SWNT-1000 | 50 | 1 | 25 | 1675825 |
| SWNT-1000 | 50 | 2 | 25 | 1683525 |
| SWNT-1000 | 50 | 5 | 25 | 1706625 |
| SWNT-1000 | 50 | 10 | 25 | 1745125 |
| SWNT-1000 | 50 | 25 | 25 | 1860625 |
| SWNT-1000 | 50 | 50 | 25 | 2053125 |
| SWNT-1000 | 50 | 50 | 50 | 2251250 |
| SWNT-500 | 50 | 0 | 0 | 1110000 |
| SWNT-500 | 50 | 1 | 25 | 1315825 |
| SWNT-500 | 50 | 2 | 25 | 1323525 |
| SWNT-500 | 50 | 5 | 25 | 1346625 |
| SWNT-500 | 50 | 10 | 25 | 1385125 |
| SWNT-500 | 50 | 25 | 25 | 1500625 |
| SWNT-500 | 50 | 50 | 25 | 1693125 |
| SWNT-500 | 50 | 50 | 50 | 1891250 |
| SWNT-50 | 50 | 0 | 0 | 786000 |
| SWNT-50 | 50 | 1 | 25 | 991825 |
| SWNT-50 | 50 | 2 | 25 | 999525 |
| SWNT-50 | 50 | 5 | 25 | 1022625 |
| SWNT-50 | 50 | 10 | 25 | 1061125 |
| SWNT-50 | 50 | 25 | 25 | 1176625 |
| SWNT-50 | 50 | 50 | 25 | 1369125 |
| SWNT-50 | 50 | 50 | 50 | 1567250 |

The reagents containing complementary strands of oligodeoxynucleotides are mixed in a minimal volume at determined stoichiometries, heated to 90° C., and then allowed to cool to ambient temperature to anneal. The peptide constructs, radiolabeled DOTA constructs, and SWNT constructs are robust and can be heated to temperatures as high as 90° C. The molecular weights of the peptide and DOTA oligodeoxynucleotide-constructs are <8000 g/mol which is 2 orders of magnitude smaller than the larger final construct product and thus should be separable from the assembly reaction mixture.

The reaction mixture will be purified by size exclusion chromatography or Centricon methodology. Removal of excess unreacted ODN-constructs is crucial. The SWNT-(DNA$_{12}$-(cDNA$_1$-cRGD)$_m$-(cDNA$_2$-M*DOTA)$_n$)$_x$ constructs are characterized physically as in Example 14.

Control SWNT-(DNA$_{12}$-(cDNA$_1$-cRAD)$_m$-(cDNA$_2$-M*DOTA)$_n$)$_x$

The reaction scheme for the preparation of control SWNT-(DNA$_{12}$-(cDNA$_1$-cRAD)$_m$-(cDNA$_2$-M*DOTA)$_n$)$_x$, is the same as described in this Example with the substitution of the RAD sequence for the RGD peptide and uses cRAD (ε-S-acetylthioacetyl)K. Only those stoichiometric combinations that serve as direct controls for the specific targeting constructs of interest are constructed.

Example 18

In Vitro Pharmacology of SWNT-(DNA$_{12}$-(cDNA$_1$-Peptide)$_m$-(cDNA$_2$-M*DOTA)$_n$)$_x$ Constructs Cell Adhesion Assay The cell adhesion assay (44) examines the ability of SWNT-(DNA$_{12}$-(cDNA$_1$-cRGD)$_m$-(cDNA$_2$-$^{111}$In*DOTA)$_n$)$_x$ constructs to interfere with HUVEC cell adhesion to fibronectin (Chemicon International, Inc., Temecula, Calif.) coated-plates. Briefly, 96 well plates are coated with 0.001 mg of fibronectin (approximately 9.5E11 molecules) in PBS at 4° C. for 10 hours. Nonspecific binding interactions are blocked by treating wells with 2% human serum (1 h at 37° C.) and washed three times with ice cold PBS. HUVEC cells are trypsinized and suspended in serum-free media. Radiolabeled construct is added to the HUVEC cells at a concentration of 2 ng per 10E3 cells and incubated for 30 min. on ice. The treated cells are added to fibronectin coated wells in triplicate at a concentration of 20E3 cells per well and incubated for 24 h at 37° C. Following this incubation period, attached cells and supernant are aspirated, the wells are washed with ice cold PBS and then are trypsinized. The trypsinized cells and associated radioactivity is harvested and is counted using a gamma counter. A negative control radiolabeled construct containing the RAD peptide is examined with and without added cRGD peptide (0.025 mg per 0.1 mL).

Cell Binding Assay

The cell binding reactivity of SWNT-$(DNA_{12}$-$(cDNA_1$-$cRGD)_m$-$(CDNA_2$-$M^*DOTA)_n)_x$ constructs is determined by incubating radiolabeled construct with HUVEC cells that have been trypsinized, collected and suspended in serum-free media. Radiolabeled construct is added to the HUVEC cells at a concentration of 2 ng per 10E6 cells and is incubated for 30 min. on ice. A negative control radiolabeled construct containing the RAD peptide is examined. In addition, 10E6 AL67 cells (murine fibroblast transfected to express CD33) will serve as another negative control. After 30 min. incubation at 0° C., the cells are collected by centrifugation and the supernatant is removed, the cells are washed once with PBS and this wash is removed. The three components, i.e., cell pellet, supernatant and wash, are counted using a gamma counter. The binding fraction is calculated as equal to (construct bound to cells)/(total bound plus unbound activity in the pellet, supernatant, and wash)) times. To avoid nonspecific cell binding, the assays are performed in the presence of 2% human serum (50-51).

Scatchard Assay

An analysis of Scatchard experimental data provides a value for the SWNT-$(DNA_{12}$-$(cDNA_1$-$cRGD)_m$-$(cDNA_2$-$^{111}In^*DOTA)_n)_x$ construct binding affinity and the integrin receptor density per cell. Both HUVEC and H5V cell lines are evaluated separately. A 100-fold excess of unlabeled construct (cold) is added to serial increments of SWNT-$(DNA_{12}$-$(cDNA_1$-$cRGD)_m$-$(cDNA_2$-$^{111}In^*DOTA)_n)_x$ hot construct (in triplicate). Freshly prepared HUVEC or H5V cells at 4° C. (5E4 cells/tube) are mixed with these mixtures of radiolabeled and cold construct. In addition, serial increments of SWNT-$(DNA_{12}$-$(cDNA_1$-$cRGD)_m$-$(cDNA_2$-$^{111}In^*DOTA)_n)_x$ hot construct (in triplicate) will be added to cells to measure the extent of non-specific binding. After 60 min. incubation at 0° C., the cells are collected by centrifugation and the supernatant is removed, the cells are washed once with PBS and this wash is removed. The radioactivity in the cell component is counted using a gamma counter along with a standard. The standard is an aliquot of the drug construct with a known specific activity. A nonlinear regression method (Prism, Graphpad Software, Inc., San Diego, Calif.) is used to fit a curve to the plot of counts per minute per cell pellet vs. added radiolabeled construct. The value of $B_{max}$ will be corrected for the binding fraction of the preparation and used to determine the number of integrin receptor binding sites per cell. An apparent Kd will be read from the plot at a value of 0.5 times the binding fraction corrected $B_{max}$ (51).

Dose Response Binding Assay

The dose response binding of SWNT-$(DNA_{12}$-$(cDNA_1$-$cRGD)_m$-$(cDNA_2$-$^{111}In^*DOTA)_n)_x$ construct to HUVEC and H5V cells is investigated for each of the stoichiometrically varied constructs that are to be investigated in vivo. Both HUVEC and H5V cell lines are evaluated separately. A 100-fold excess of unlabeled construct (cold) is added to serial increments of SWNT-$(DNA_{12}$-$(cDNA_1$-$cRGD)_m$-$(cDNA_2$-$^{111}In^*DOTA)_n)_x$ hot construct (in triplicate). Freshly prepared HUVEC or H5V cells at 4° C. (5E4 cells/tube) are mixed with these mixtures of radiolabeled and cold construct. The cells are collected, are washed and the radioactivity counted against a standard as described in this Example. The fraction of activity bound per cell pellet is plotted as a function of the log of the concentration of total construct added.

Cell Cytotoxicity Assay

The potency and specificity of SWNT-$(DNA_{12}$-$(cDNA_1$-$cRGD)_m$-$(cDNA_2$-$^{225}Ac^*DOTA)_n)_x$ for killing single H5V cells are determined using 5E4 H5V ($a_vb_3$ integrin-positive) cells per well in 0.20 mL in 96 well plates. Serial dilutions of SWNT-$(DNA_{12}$-$(cDNA_1$-$cRGD)_m$-$(cDNA_2$-$^{225}Ac^*DOTA)_n)_x$ are added to the cells to yield final activity in the wells ranging from 10 to 10,000 nCi/mL. The experiments are done with different specific activities of the Ac-225 labeled constructs (0.05 to 0.5 mCi/mg). The plates are incubated 48 h at 37° C. in 5% $CO_2$. Controls are HCl and serum free media and PBS formulation. Specificity is confirmed using hot construct diluted 100-fold with cold unlabeled construct. After incubation, cell viability is determined by [$^3$H]thymidine (DuPont NEN, North Billerica, Mass.) incorporation (50-51).

Stability Assays

Stability in vitro of SWNT-$(DNA_{12}$-$(cDNA_1$-$cRGD)_m$-$(cDNA_2$-$^{225}Ac^*DOTA)_n)_x$ constructs is examined in 100% human serum (Sigma Chemical Co., St. Louis, Mo.), 100% mouse serum, PBS, and 25% human serum albumin (Swiss Red Cross, Bern, Switzerland) at 37° C. for 15 days (41). A 0.20 mL aliquot of SWNT-$(DNA_{12}$-$(cDNA_1$-$cRGD)_m$-$(cDNA_2$-$^{225}Ac^*DOTA)_n)_x$ construct is added to 4.0 mL of each of the four media. At each time point, 0.05 mL is removed from the four samples and is mixed with 0.01 mL of 10 mM diethylenetriaminepentaacetic acid (DTPA) (Aldrich Chemical Co., Milwaukee, Wis.) for 15 min. at 37° C. After this 15 min. incubation period, an aliquot is removed and is spotted on instant thin layer chromatography paper impregnated with silica gel (Gelman Science Inc., Ann Abbor, Mich.) and is developed with a 0.01 M EDTA solution (triplicate analysis). Strips were dried and counted four days later with a gas ionization detector (Ambis 4000, Ambis Inc., San Diego, Calif.). The activity component with $R_f$=0 was the SWNT-$(DNA_{12}$-$(cDNA_1$-$cRGD)_m$-$(cDNA_2$-$^{225}Ac^*DOTA)_n)_x$.

Stability in vivo is determined by injecting 10 female nude mice (Taconic, Germantown, N.Y.) via tail vein i.v. route with 300 nCi in 0.1 mL of SWNT-$(DNA_{12}$-$(cDNA_1$-$cRGD)_m$-$(cDNA_2$-$^{225}Ac^*DOTA)_n)_x$ construct (47). The % $^{225}$Ac that was bound to the construct in the mouse serum as a function of time is determined. Results are obtained by HPLC size exclusion chromatography, using a Beckman Coulter System Gold Bioessential HPLC. The stationary phase employs a Tosohass Bioscience TSK-GEL G3000SWXL analytical column. The mobile phase is 0.15 M sodium chloride, 0.02 M sodium acetate, and 0.05% (w/v) sodium azide adjusted to pH 7.0. The column and mobile phase are calibrated with a selection of molecular weight standards. Detection of the peaks is performed using a Beckman Coulter 168 diode array detector. Detection of fluorescent compounds is performed simultaneously using a Jasco FP-2020 fluorescence detector. Eluate fractions are collected manually and counted with a Beckman LS 6000IC beta scintillation counter (Beckman Instruments, Inc., Fullerton, Calif.). Blood samples are drawn from animals over a 5 day period to assess stability.

Cell Internalization Assay

Internalization of the cell surface bound SWNT-(DNA$_{12}$-(cDNA$_1$-cRGD)$_m$-(cDNA$_2$-$^{225}$Ac*DOTA)$_n$)$_x$ construct is determined by incubating 1 mg/mL of SWNT-(DNA$_{12}$-(cDNA$_1$-cRGD)$_m$-(cDNA$_2$-$^{111}$In*DOTA)$_n$)$_x$ construct with 2E5 HUVEC or H5V cells (in duplicate) in a volume of 2.5 mL RPMI media as a function of time at 37° C. (47,51). The construct exposed cells are pelleted by centrifugation at timepoints of approximately 1 min., 2 h, 4 h and 24 h and the pellets are washed twice in RPMI media. The surface-bound In-111 construct is stripped with 1 mL of 50 mM glycine/150 mM NaCl (Aldrich Chemical Co, Inc., Milwaukee, Wis.), pH 2.8, at 24° C. for 10 min. Total cell-associated radioactivity and internalized (acid-resistant) radioactivity were determined by counting the [$^{111}$In]-labeled samples with a Packard Cobra Gamma Counter (Packard Instrument Co., Inc., Meriden, Conn.) with a 15-550 keV energy window. In order to avoid nonspecific and Fc receptor binding by the cells, the assays were performed in the presence of 2% human serum.

Example 19

In Vivo Efficacy of SWNT-(DNA$_{12}$-(cDNA$_1$-Peptide)$_m$-(cDNA$_2$-M*DOTA)$_n$)$_x$ in Vascular Angiogenesis Models Matrigel/Heparin/aFGF Implant Murine Model Female C57/BL mice are injected subcutaneously (s.c.) with 0.5 mL of Matrigel (Becton Dickinson Labware, Bedford Mass.) containing 100 ng/mL of aFGF (R&D, Minneapolis, Minn.) and 70 Units heparin per mL near the abdominal midline with a 25 G needle. The gel should persist for 10-12 days. Since the mass of angiogenic and quiescent vasculature in the gel will be quite small, the amount of radioactivity in the gel can be measured and correlated with the amount of protein (BioRad Total Protein Assay, BioRad, Inc., Hercules, Calif.) and hemoglobin (Drabkin Reagent Kit 525, Sigma, St. Louis, Mo.) in the gel.

On day 3 following the implant of the Matrigel/aFGF/Heparin gel, one group (n=9) of mice will receive approximately 0.5 mL of the SWNT-(DNA$_{12}$-(cDNA$_1$-cRGD)$_m$-(cDNA$_2$-$^{111}$In*DOTA)$_n$)$_x$ construct (0.05 mCi In-111) while another group (n=9) will receive the non-targeting SWNT-(DNA$_{12}$-(cDNA$_1$-cRAD)$_m$-(cDNA$_2$-$^{111}$In*DOTA)$_n$)$_x$ irrelevant control construct via i.v. injection. Three animals from each group are sacrificed at 1, 6, and 24 h post injection. Blood and tissue samples including: heart, kidneys, lung, spleen, liver, stomach, intestine, brain, muscle, bone and gel are harvested, weighed and counted using a Packard Cobra Gamma Counter (Packard Instrument Co., Inc.). The percent of the injected dose per gram of tissue (% ID/g) is determined by measuring the activity in 0.025 mg aliquots of each respective construct injectate. A further control is used to measure the uptake of constructs in a Matrigel-only implant at a 24 h time point in a group of three mice. If no significant uptake is noted, then this control need not be included on a routine basis.

LNCaP Cell/Matrigel Implant Murine Model

Male athymic nude mice (8 weeks old), will be injected s.c. with 6-7E6 LNCaP tumor cells mixed with Matrigel (Becton Dickinson Labware, Bedford Mass.) in the right hind leg in a volume of 0.25 mL. Measureable human Prostate Speciific Antigen (PSA) is detected around day 12 at serum concentrations >1 ng/mL. On day 14 following the xenograft, one group (n=18) of mice receive approximately 0.5 mL of the SWNT-(DNA$_{12}$-(cDNA$_1$-cRGD)$_m$-(cDNA$_2$-$^{111}$In*DOTA)$_n$)$_x$ construct (0.05 mCi In-111) while another group (n=18) receive the non-targeting SWNT-(DNA$_{12}$-(cDNA$_1$-cRAD)$_m$-(cDNA$_2$-$^{111}$In*DOTA)$_n$)$_x$ irrelevant control construct via i.v. injection. Three animals from each group will be sacrificed at 1, 2, 6, 24, 72 and 120 h post injection. Blood and tissue samples are harvested, weighed and counted and the percent of the injected dose per gram of tissue (% ID/g) is determined as with the Matrigel/Heparin/aFGF model.

Tumor growth in vivo was assessed histologically on days 2, 3, 5, 7, and 10 by sacrificing mice and examining the morphology, size, vascularization, and encapsulation of the tumor cells in the leg. On day 2, the tumors were characterized as disorganized cell clusters and nodules each comprised of several thousands of cells. The nodules were not vascularized and not encapsulated. On day 3, the tumors were more organized and were becoming vascularized, but still not encapsulated. By the fifth day, vascularization was more pronounced and on day 7 the tumors were encapsulated.

Targeting of SWNT-(DNA$_{12}$-(cDNA$_1$-cRGD)$_m$-(cDNA$_2$-$^{111}$In*DOTA)$_n$)$_x$, tumor growth and effectiveness of therapy can be monitored via PET imaging. The PET construct SWNT-(DNA$_{12}$-(cDNA$_1$-cRGD)$_m$-(cDNA$_2$-M*DOTA)$_n$)$_x$ is synthesiszed where M is Y-86 ($t_{1/2}$=14.74 h.) or Ga-68 ($t_{1/2}$=68.3 min.) positron emitting radionuclides. The isotope is selected based upon the biodistribution parameters. Generally, approximately 0.10 mCi per animal are administered and image acquisition times of 10-40 min are used. Animals are anesthetized for acquisition using isofluorane gas anesthesia. Dosimetry to targeted vessels and tumor is assessed using the PET data and corresponding biodistribution data so that estimates of the dose delivered from the alpha particle decays to the angiogenic tissue can be calculated.

Therapeutic Efficacy of SWNT-(DNA$_{12}$-(cDNA$_1$-cRGD)$_m$-(cDNA$_2$-$^{225}$Ac*DOTA)$_n$)$_x$ in LNCaP Cell/Matrigel Model Mice (n=50) are treated with a cumulative dose of 200 nCi Ac-225 in 4×50 nCi doses or with non-labeled control by i.v. injections on each of days 3-6, following tumor implant, with one of 1) 50 nCi of SWNT-(DNA$_{12}$-(cDNA$_1$-cRGD)$_m$-(cDNA$_2$-$^{225}$Ac*DOTA)$_n$)$_x$ construct (n=15); 2) 50 nCi of SWNT-(DNA$_{12}$-(cDNA$_1$-cRAD)$_m$-(cDNA$_2$-$^{225}$Ac*DOTA)$_n$)$_x$ construct to control for non-specific radioation effects (n=15); 3) unlabeled SWNT-(DNA$_{12}$-(cDNA$_1$-cRGD)$_m$-(cDNA$_2$-DOTA)$_n$)$_x$ construct to control for inhibitory effects of binding to target (n=10); or 4) untreated growth control receiving only the injection vehicle (n=10).

Animals are monitored every other day for the appearance of a blue-colored lesion beneath the skin at the site of implantation, indicating the growth of a vascularized tumor. PSA levels are assayed on day 14 and then every 21 days thereafter. Animals are retroorbitally bled under anesthesia of xylazine (10 mg/kg) and ketamine*HCl (200 mg/kg) and their PSA levels assayed using the IMX PSA Assay. The median time to death in untreated controls is approximately 6 weeks. Animals are sacrificed when tumor area ≥2.5 cm$^2$) with concurrently escalating serum PSA levels, that is when serum PSA≥100 ng/mL). PSA data is evaluated using an unpaired t-test (2-tailed). The data for median tumor-free survival versus time is evaluated using a log-rank test and plotted as a Kaplan-Meier survival curve.

Murine Neovascualrization in Glial Tumorigenesis Model

Murine neovascularization in glial tumorigenesis (52-54) modeling requires an intracranial (i.c.) injection (0.001 mL) of RCAS retrovirus transfected DF-1 cells into neonatal Ef-luc N-tva double transgenic mice. The model yields a well vascularized tumor. Approximately 80% of animals will succumb to disease by 12 weeks.

On day 28 following the xenograft, one group (n=18) of mice will receive approximately 0.5 mL of the SWNT-$(DNA_{12}\text{-}(cDNA_1\text{-}cRGD)_m\text{-}(cDNA_2\text{-}^{111}In^*DOTA)_n)_x$ construct (0.05 mCi In-111) while another group (n=18) will receive the non-targeting SWNT-$(DNA_{12}\text{-}(cDNA_1\text{-}cRAD)_m\text{-}(cDNA_2\text{-}^{111}In^*DOTA)_n)_x$ irrelevant control construct via i.v. injection. Three animals from each group are sacrificed at 1, 2, 6, 24, 72 and 120 h post injection. Blood and tissue samples are harvested, weighed and counted and the percent of the injected dose per gram of tissue (% ID/g) is determined as with the Matrigel/Heparin/aFGF model.

In addition to monitoring animals for symptoms of tumor development, such as hydrocephalus and lethargy, these animals can also be followed using PET imaging, as described, bioluminescence imaging and dynamic contrast magnetic resonance imaging (DCE-MRI) techniques (55). For bioluminescence imaging is available from. Approximately 0.30 mg D-Luciferin (Firefly) (Xenogen Corp. Alameda, Calif.) is dissolved in 0.20 mL of phosphate-buffered saline (PBS) for i.p. injection per mouse. The D-Luciferin should be thawed immediately prior to use and should be protected from light, to the extent possible, until injection. Mice are imaged 10 min post-injection and no later than 16-20 min post-injection. Animals are anesthetized for imaging as described for PET imaging.

Therapeutic Efficacy of SWNT-$(DNA_{12}\text{-}(cDNA_1\text{-}cRGD)_m\text{-}(cDNA_2\text{-}^{225}Ac^*DOTA)_n)_x$ in Neonatal Ef-luc N-Tva Double Transgenic Mice On day 14 following tumor implant into neonatal Ef-luc N-tva double transgenic mice (n=40), optical imaging using in vivo bioluminescence, as described immediately above, is used to confirm tumor take and the extent of growth. Animals with 100E4 photons per 2 minute count time will be included in the study. These animals are randomly mixed into four groups (n=10) and then treated with intravenously injected labeled construct or labeled control or of unlabeled construct or control, as described for the LNCaP cell/Matrigel model, on days 15-18.

Animals are then monitored every third day for the appearance of hydrocephalus and lethargy, symptoms of tumor development. The median time to death in untreated controls is approximately 12 weeks. Animals will also be imaged on day 28 following tumor injection with 0.30 mg Luciferin per mouse, and then every 28 days following. The data for median tumor-free survival versus time will be evaluated using a log-rank test and plotted as a Kaplan-Meier survival curve.

Histopathological Analysis of Tumor and Vascular Tissue Treated with SWNT-$(DNA_{12}\text{-}(cDNA_1\text{-}cRGD)_m\text{-}(cDNA_2\text{-}^{225}Ac^*DOTA)_n)_x$ Tumor-bearing mice in all three murine vascular angiogenesis models are sacrificed 24, 72, and 144 hours following i.v. injection of the radioimmunotherapeutic construct. Tumors are removed, sectioned and their architecture examined. Blood vessels are identified by staining with vascular endothelial (VE) cell-cadherin-specific antibody (VE cadherin antibody, Santa Cruz Biotechnologies, Santa Cruz, Calif.). Apoptotic cells are identified by staining with terminal deoxynucleotidyl transferase-mediated deoxyuridine triphosphate nick-end label (TUNEL Assay) using the Apotag kit (Oncor, Gaithersburg, Md.). Necrotic cells are identified by staining with hematoxylin and eosin.

Toxicity of SWNT-$(DNA_{12}\text{-}(cDNA_1\text{-}cRGD)_m\text{-}(cDNA_2\text{-}^{225}Ac^*DOTA)_n)_x$ A toxicity study of SWNT-$(DNA_{12}\text{-}(cDNA_1\text{-}cRGD)_m\text{-}(cDNA_2\text{-}^{225}Ac^*DOTA)_n)_x$ construct dose escalation is performed over a 90 day period. Normal animals are monitored for effects due to Ac-225 and SWNT toxicity. Survival, blood chemistries and histopathological changes as a function of Ac-225 activity and SWNT mass are evaluated.

Forty-five 6-8 week old female C57/BL normal mice are separated into 3 groups (n=15 per group). In the first group, three animals are injected i.v. with 0.1 mL of 1000, 500, 250, 125, or 50 nCi of SWNT-$(DNA_{12}\text{-}(cDNA_1\text{-}cRGD)_m\text{-}(cDNA_2\text{-}^{225}Ac^*DOTA)_n)_x$, respectively. In the second group of 15 animals, three mice receive an i.v. injection of 0.20, 0.10, 0.05, 0.025, and 0.005 mg of unlabeled SWNT-$(DNA_{12}\text{-}(cDNA_1\text{-}cRGD)_m\text{-}(cDNA_2\text{-}DOTA)_n)_x$, respectively. The third group receives only injection vehicle and will serve as the controls.

Data include viability, appearance, activity, weight, and white and red blood cell counts recorded at monthly time points. At the end of the 90 days, blood samples are obtained after cardiac puncture and are analyzed for blood urea nitrogen, creatinine, alkaline phosphatase, total and direct bilirubin, albumin, glucose, gamma glutamyl transferase, triglycerides, cholesterol, inorganic phosphate, calcium, magnesium, sodium and chloride using a DAX Clinical Analyzer (Bayer Diagnostics, Tarrytown, N.Y.). Animals are autopsied and histopathology of tissue samples, such as, liver, spleen, intestine, bone, muscle, kidney, lung, and heart, are evaluated.

The following references were cited herein:
1. Shvedova et al., J Toxicol Environ Health A., 2003, 66(20):1909-26.
2. Cui et al., Toxicology Letters, 2005, 155(1):73-81.
3. Bianco et al., J Am Chem Soc., 2005, 127(1):57-59.
4. Pantarotto et al., Chemical Communications, 2004, 7(1):16-7.
5. Shi et al., J Am Chem Soc., 2004, 126(22):6850-6851.
6. Dresselhaus et al., eds. Carbon Nanotubes: Synthesis, Structure, Properties and Applications. 1 ed. Topics in Applied Physics. Vol. 80. 2001, Springer-Verlag: Heidelberg, 447.
7. Guo et al., Advanced Materials, 1998. 10(9):701-703.
8. Georgakilas et al., J. Am. Chem. Soc, 2002. 124(5):760-761.
9. Luet et al., J. Am. Chem. Soc. 2003, 125:10459-10464.
10. Coleman et al., J. Am. Chem. Soc. 2003, 125:8722-8723.
11. Loupy, A., Ed., Wiley-VCH, Microwaves in Organic Synthesis; Weinheim, 2003, Chapter 9, 295-344.
12. Delgado et al. Chem. Commun. 2004, 1734-1735.
13. Stein et al. Arch. Biochem. Biophys. 1973, 155:202.
14. Ellman, G. L. Arch. Biochem. Biophys. 1959, 82:70-77.
15. McDevitt et al. The PET and Cancer Symposium, Groningen, The Netherlands, 1996.
16. Finn et al. The 15th International Conference on the Application of Accelerators in Research and Industry, Denton Tex., 1998.
17. Chiu et al., M. R. Nat Cell Biol, 2002, 4:343-350.
18. Herskovits et al., J Cell Biol, 1993, 122:565-578.
19. Vieira et al., J Cell Biol, 2001, 155:19-25.
20. Ren et al., Proc Natl Acad Sci USA, 1998, 95:6187-6192.
21. Bivona et al., J Cell Biol, 2004, 164:461-470.
22. White, K. D., and Capra, J. D., *J Exp Med,* 2002, 196:551-555.
23. LaTulippe et al., Cancer Res., 2002 Aug. 1, 62(15):4499-506.
24. Pantarotto et al., Journal of the American Chemical Society, 2003, 125(20):6160-6164.
25. Erlanger et al., J. Am. Chem. Soc. 2001, 1(9): 465-467.
26. Chen et al., PNAS, 2003, 100(9):4984-4989.

27. Wei et al., Cancer Immunol Immunother, 1996, 42(6): 362-368.
28. Gleave et al., Cancer Res,
29. Conway et al., J Immunol Methods, 2000, 233(1-2):57-65.
30. Yang et al., Proc Natl Acad Sci USA, 2000, 97(3): 1206-1211.
31. Bouvet et al. Cancer Res, 2002, 62(5): 1534-1540.
32. Hirsch, A., Angew. Chem. Int. Ed., 2002, 41:1853-1859.
33. Ma et al. Leukemia, 2002, 16:60-66.
34. Latouche, J-B. and Sadelain, M., Nature Biotech, 2000, 18:405-409.
35. Riviere, K. B. and Mulligan, R. C., PNAS, 1995, 92:6733-6737.
36. McDevitt et al., Science 2001, 294:1537-1540.
37. Ghertie et al., Int. J. Cancer, 1990, 45:481-485.
38. Terwey et al., Blood, 2005, 106:3322-3330.
39. McDevitt et al. Applied Rad Isot. 2002, 57:841-847.
40. Hjelstuen et al., J. Labelled Compounds and Radiopharmaceuticals, 1999, 42:737-760.
41. Florent et al., Journal of Medicinal Chemistry, 1998. 41:3572-3581.
42. Nagy et al., The Journal of Biological Chemistry, 2003, 278(22): 20286-20292.
43. Wright J. E., Bioorganic & Medicinal Chemistry, 2002, 10:493-500.
44. Kim D. H., Current Topics in Medicinal Chemistry, 2004, 4:1217-1226.
45. Porgador et al., Immunity, 1997, 6:715-726.
46. Oka et al., J. Immuno., 2000, 1873-1880.
47. Gaiger et al., Blood. 2000, 96:1480-1489.
48. Falk, K. and O. Rotzschke, Semin. Immunil., 1996, 5:81.
49. Ruegg et al., Nat. Med. 1998, 4(4):408-414.
50. Nikula et al., *J Nucl Med,* 1999; 40:166-176.
51. McDevitt et al., Cancer Res., 2000, 60:6095-6102.
52. Uhrbom et al., Nat Med., 2004, 10(11):1257-1260.
53. Shih et al., Cancer Res., 2004, 64(14):4783-4789.
54. Holland, E C and H E Varmus, Proc Natl Acad Sci USA., 1998, 95(3):1218-1223.
55. Anderson et al., Blood. 2005, 105(1):420-425.
56. Sarin et al., Anal Biochem. 1981, 17:147-157.
57. McDevitt et al., Science, 2001, 294:1537-1540.
58. Nikula et al., Nucl Med Biol, 1995, 22:387-390.
. Dadachova et al., Nucl Med Biol. 1999, 26:977-982.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of treating a cancer in a subject, comprising: administering a soluble single wall carbon nanotube (SWNT) construct having the structure SWNT-(DNA$_{1,2}$-(cDNA$_1$-peptide)$_m$-(cDNA$_2$-M*tetraazacyclododecane-1,4,7,10-tetra acetic acid (DOTA))$_n$)$_x$, such that cDNA$_1$ is linked to the peptide, cDNA$_2$ is linked to DOTA and DNA$_{1,2}$ is linked to the SWNT; and, wherein cDNA$_1$ and cDNA$_2$ independently are non-identical oligomers and DNA$_{1,2}$ is an oligomer with a sequence complementary to cDNA$_1$ and cDNA$_2$; and, wherein said DNA$_{1,2}$ is the sequence shown in SEQ ID NO: 1, said cDNA$_1$ is the sequence shown in SEQ ID NO: 2 and said cDNA$_2$ is the sequence shown in SEQ ID NO: 3; and, wherein said peptide is a targeting antibody or a targeting cyclic RGD or an NGR peptide ligand, M* is a radionuclide, x is 1 to 300; and m and n are independently 1 to 300; wherein, upon targeting cancer-associated cells with the peptide, said radionuclide M* has an anticancer effect against said cells thereby treating the cancer in the subject.

2. The method of claim 1, wherein the targeting antibody is a therapeutic antibody.

3. The method of claim 2, wherein the therapeutic antibody is rituximab, trastuzumab, or antinucleolin.

4. The method of claim 1, wherein M* is actinium-225, astatine-211, technetium-99, lutetium-177, gallium-68, holmium-166, bismuth-212, bismuth-213, yttrium-90, copper-64, copper-67, samarium-117, samarium-153, iodine-123, iodine-124, iodine-125, or iodine-131.

5. The method of claim 1, wherein said cancer associated cells are cancer cells or endothelial cells of the vasculature associated with the cancer.

* * * * *

SEQUENCE LISTING

```
<160> NUMBER OF SEQ ID NOS: 35

<210> SEQ ID NO 1
<211> LENGTH: 42
<212> TYPE: DNA
<213> ORGANISM: Artificial Sequence
<220> FEATURE:
<223> OTHER INFORMATION: SWNT DNA platform sequence

<400> SEQUENCE: 1
tagtgttgac gaagggacta tgggtcatcg tacgaccccc cc                           42

<210> SEQ ID NO 2
<211> LENGTH: 24
<212> TYPE: DNA
<213> ORGANISM: Artificial Sequence
<220> FEATURE:
<223> OTHER INFORMATION: SWNT DNA platform sequence

<400> SEQUENCE: 2
gtcccttcgt caacactacc cccc                                              24

<210> SEQ ID NO 3
<211> LENGTH: 21
<212> TYPE: DNA
<213> ORGANISM: Artificial Sequence
<220> FEATURE:
<223> OTHER INFORMATION: SWNT DNA platform sequence

<400> SEQUENCE: 3
atacccagta gcatgctgcc c                                                 21

<210> SEQ ID NO 4
<211> LENGTH: 9
<212> TYPE: PRT
<213> ORGANISM: Artificial Sequence
```

```
<220> FEATURE:
<223> OTHER INFORMATION: Minimal CD8 epitope

<400> SEQUENCE: 4

Cys Ser Ile Ile Asn Phe Glu Lys Leu
                5

<210> SEQ ID NO 5
<211> LENGTH: 8
<212> TYPE: PRT
<213> ORGANISM: Artificial Sequence
<220> FEATURE:
<223> OTHER INFORMATION: Minimal CD8 epitope

<400> SEQUENCE: 5

Ser Ile Ile Asn Phe Glu Lys Leu
                5

<210> SEQ ID NO 6
<211> LENGTH: 18
<212> TYPE: PRT
<213> ORGANISM: Artificial Sequence
<220> FEATURE:
<223> OTHER INFORMATION: CD8 epitope plus flanking amino acids

<400> SEQUENCE: 6

Cys Glu Val Ser Gly Leu Glu Gln Leu Glu Ser Ile Ile Asn Phe
                5                   10                  15

Glu Lys Leu

<210> SEQ ID NO 10
<211> LENGTH: 31
<212> TYPE: PRT
<213> ORGANISM: Artificial Sequence
<220> FEATURE:
<223> OTHER INFORMATION: CD4 epitope plus CD8 epitope flanking
      amino acids

<400> SEQUENCE: 10

Cys Ile Ser Gln Ala Val His Ala Ala His Ala Glu Ile Asn Glu
                 5                  10                  15

Ala Gly Arg Glu Ser Ile Ile Asn Phe Glu Lys Leu Thr Glu Trp
             20                  25                  30

Thr

<210> SEQ ID NO 11
<211> LENGTH: 30
<212> TYPE: PRT
<213> ORGANISM: Artificial Sequence
<220> FEATURE:
<223> OTHER INFORMATION: CD4 epitope plus CD8 epitope flanking
      amino acids

<400> SEQUENCE: 11

Ile Ser Gln Ala Val His Ala Ala His Ala Glu Ile Asn Glu Ala
                 5                  10                  15

Gly Arg Glu Ser Ile Ile Asn Phe Glu Lys Leu Thr Glu Trp Thr
             20                  25                  30

<210> SEQ ID NO 12
<211> LENGTH: 33
<212> TYPE: PRT
<213> ORGANISM: Artificial Sequence
<220> FEATURE:
<223> OTHER INFORMATION: CD8 epitope plus CD4 epitope flanking
      amino acids

<400> SEQUENCE: 12

Cys Glu Gln Leu Glu Ser Ile Ile Asn Phe Glu Lys Leu Thr Glu
                 5                  10                  15

Lys Ile Ser Gln Ala Val His Ala Ala His Ala Glu Ile Asn Glu
             20                  25                  30

Ala Gly Arg

<210> SEQ ID NO 13
<211> LENGTH: 33
<212> TYPE: PRT
<213> ORGANISM: Artificial Sequence
<220> FEATURE:
<223> OTHER INFORMATION: CD8 epitope plus CD4 epitope flanking
      amino acids

<400> SEQUENCE: 13

Glu Gln Leu Glu Ser Ile Ile Asn Phe Glu Lys Leu Thr Glu Lys
                 5                  10                  15

Ile Ser Gln Ala Val His Ala Ala His Ala Glu Ile Asn Glu Ala
             20                  25                  30

Gly Arg Cys

<210> SEQ ID NO 14
<211> LENGTH: 15
<212> TYPE: PRT
<213> ORGANISM: Artificial Sequence
<220> FEATURE:
<223> OTHER INFORMATION: Human HLA-DR+ peptide

```
<400> SEQUENCE: 14

Leu Val Arg His His Asn Met His Gln Arg Asn Met Thr Lys Leu
                5                   10                  15

<210> SEQ ID NO 15
<211> LENGTH: 9
<212> TYPE: PRT
<213> ORGANISM: Artificial Sequence
<220> FEATURE:
<223> OTHER INFORMATION: Heteroclitic WT1-10 epitope

<400> SEQUENCE: 15

Ala Leu Leu Pro Ala Val Ser Ser Leu
                5

<210> SEQ ID NO 16
<211> LENGTH: 9
<212> TYPE: PRT
<213> ORGANISM: Artificial Sequence
<220> FEATURE:
<223> OTHER INFORMATION: Heteroclitic WT1-10A epitope

<400> SEQUENCE: 16

Ala Tyr Leu Pro Ala Val Ser Ser Leu
                5

<210> SEQ ID NO 17
<211> LENGTH: 9
<212> TYPE: PRT
<213> ORGANISM: Artificial Sequence
<220> FEATURE:
<223> OTHER INFORMATION: Heteroclitic WT1-126 epitope

<400> SEQUENCE: 17

Arg Met Phe Pro Asn Ala Pro Tyr Leu
                5

<210> SEQ ID NO 18
<211> LENGTH: 9
<212> TYPE: PRT
<213> ORGANISM: Artificial Sequence
<220> FEATURE:
<223> OTHER INFORMATION: Heteroclitic WT1-126A epitope

<400> SEQUENCE: 18

Arg Tyr Phe Pro Asn Ala Pro Tyr Leu
                5

<210> SEQ ID NO 19
<211> LENGTH: 9
<212> TYPE: PRT
<213> ORGANISM: Artificial Sequence
<220> FEATURE:
<223> OTHER INFORMATION: Heteroclitic WT1-136 epitope

<400> SEQUENCE: 19

Ser Cys Leu Glu Ser Gln Pro Thr Ile
                5

<210> SEQ ID NO 20
<211> LENGTH: 9
<212> TYPE: PRT
<213> ORGANISM: Artificial Sequence
<220> FEATURE:
<223> OTHER INFORMATION: Heteroclitic WT1-136A epitope

<400> SEQUENCE: 20
```

Ser Tyr Leu Glu Ser Gln Pro Thr Ile
            5

<210> SEQ ID NO 21
<211> LENGTH: 9
<212> TYPE: PRT
<213> ORGANISM: Artificial Sequence
<220> FEATURE:
<223> OTHER INFORMATION: Heteroclitic WT1-239 epitope

<400> SEQUENCE: 21

Asn Gln Met Asn Leu Gly Ala Thr Leu
            5

<210> SEQ ID NO 22
<211> LENGTH: 9
<212> TYPE: PRT
<213> ORGANISM: Artificial Sequence
<220> FEATURE:
<223> OTHER INFORMATION: Heteroclitic WT1-239A epitope

<400> SEQUENCE: 22

Asn Tyr Met Asn Leu Gly Ala Thr Leu
            5

<210> SEQ ID NO 23
<211> LENGTH: 9
<212> TYPE: PRT
<213> ORGANISM: Artificial Sequence
<220> FEATURE:
<223> OTHER INFORMATION: Heteroclitic WT1-285 epitope

<400> SEQUENCE: 23

Gln Tyr Arg Ile His Thr His Gly Val
            5

<210> SEQ ID NO 24
<211> LENGTH: 9
<212> TYPE: PRT
<213> ORGANISM: Artificial Sequence
<220> FEATURE:
<223> OTHER INFORMATION: Heteroclitic WT1-285A epitope

<400> SEQUENCE: 24

Gln Tyr Arg Ile His Thr His Gly Leu
            5

<210> SEQ ID NO 25
<211> LENGTH: 9
<212> TYPE: PRT
<213> ORGANISM: Artificial Sequence
<220> FEATURE:
<223> OTHER INFORMATION: Heteroclitic WT1-424 epitope

<400> SEQUENCE: 25

Lys Phe Ala Arg Ser Asp Glu Leu Val
            5

<210> SEQ ID NO 26
<211> LENGTH: 9
<212> TYPE: PRT
<213> ORGANISM: Artificial Sequence
<220> FEATURE:
<223> OTHER INFORMATION: Heteroclitic WT1-424A epitope

<400> SEQUENCE: 26

Lys Phe Ala Arg Ser Asp Glu Leu Ile
            5

<210> SEQ ID NO 27
<211> LENGTH: 9
<212> TYPE: PRT
<213> ORGANISM: Artificial Sequence
<220> FEATURE:
<223> OTHER INFORMATION: Heteroclitic WT1-126 epitope

<400> SEQUENCE: 27

Arg Met Phe Pro Asn Ala Pro Tyr Leu
            5

<210> SEQ ID NO 28
<211> LENGTH: 9
<212> TYPE: PRT
<213> ORGANISM: Artificial Sequence
<220> FEATURE:
<223> OTHER INFORMATION: Heteroclitic WT1-126B epitope

<400> SEQUENCE: 28

Arg Met Phe Pro Asn Ala Pro Tyr Met
            5

<210> SEQ ID NO 29
<211> LENGTH: 9
<212> TYPE: PRT
<213> ORGANISM: Artificial Sequence
<220> FEATURE:
<223> OTHER INFORMATION: Heteroclitic WT1-221 epitope

<400> SEQUENCE: 29

Tyr Ser Ser Asp Asn Leu Tyr Gln Met
            5

<210> SEQ ID NO 30
<211> LENGTH: 9
<212> TYPE: PRT
<213> ORGANISM: Artificial Sequence
<220> FEATURE:
<223> OTHER INFORMATION: Heteroclitic WT1-221A epitope

<400> SEQUENCE: 30

Tyr Met Ser Asp Asn Leu Tyr Gln Met
            5

<210> SEQ ID NO 31
<211> LENGTH: 9
<212> TYPE: PRT
<213> ORGANISM: Artificial Sequence
<220> FEATURE:
<223> OTHER INFORMATION: Heteroclitic WT1-228 epitope

<400> SEQUENCE: 31

Gln Met Thr Ser Gln Leu Glu Cys Met
            5

<210> SEQ ID NO 32
<211> LENGTH: 9
<212> TYPE: PRT
<213> ORGANISM: Artificial Sequence
<220> FEATURE:
<223> OTHER INFORMATION: Heteroclitic WT1-228A epitope

<400> SEQUENCE: 32

Gln Met Thr Ser Asn Leu Glu Cys Met

```
<210> SEQ ID NO 33
<211> LENGTH: 9
<212> TYPE: PRT
<213> ORGANISM: Artificial Sequence
<220> FEATURE:
<223> OTHER INFORMATION: Heteroclitic WT1-235 epitope

<400> SEQUENCE: 33

Cys Met Thr Trp Asn Gln Met Asn Leu
                  5

<210> SEQ ID NO 34
<211> LENGTH: 9
<212> TYPE: PRT
<213> ORGANISM: Artificial Sequence
<220> FEATURE:
<223> OTHER INFORMATION: Heteroclitic WT1-235A epitope

<400> SEQUENCE: 34

Cys Met Thr Trp Asn Gln Met Asn Met
                  5

<210> SEQ ID NO 35
<211> LENGTH: 9
<212> TYPE: PRT
<213> ORGANISM: Artificial Sequence
<220> FEATURE:
<223> OTHER INFORMATION: Heteroclitic WT1-126 epitope

<400> SEQUENCE: 35

Arg Met Phe Pro Asn Ala Pro Tyr Leu
                  5
```